US006436109B1

(12) United States Patent
Kontos

(10) Patent No.: US 6,436,109 B1
(45) Date of Patent: *Aug. 20, 2002

(54) DEVICE AND METHOD FOR SUTURING BLOOD VESSELS AND THE LIKE

(75) Inventor: Stavros Kontos, Woodcliff Lake, NJ (US)

(73) Assignee: X-site, L.L.C., Totowa, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/340,422

(22) Filed: Jun. 28, 1999

Related U.S. Application Data

(63) Continuation-in-part of application No. 09/126,316, filed on Jul. 30, 1998, now Pat. No. 6,024,747, which is a continuation-in-part of application No. 08/661,884, filed on Jun. 11, 1996, now Pat. No. 6,000,792.

(51) Int. Cl.[7] ............................................... A61B 17/04
(52) U.S. Cl. ..................................................... 606/148
(58) Field of Search ................................ 606/144, 148, 606/145, 138, 139, 149, 224, 225, 228, 233; 347/89

(56) References Cited

U.S. PATENT DOCUMENTS

| | | |
|---|---|---|
| 3,807,407 A | 4/1974 | Schweizer |
| 4,107,953 A | 8/1978 | Casillo |
| 4,493,323 A | 1/1985 | Albright et al. |
| 4,553,543 A | 11/1985 | Amarasinghe |
| 4,757,827 A | 7/1988 | Buchbinder et al. |
| 4,799,495 A | 1/1989 | Hawkins et al. |
| 4,841,888 A | 6/1989 | Mills et al. |
| 4,890,612 A | 1/1990 | Kensey |
| 4,890,615 A | 1/1990 | Caspari et al. |
| 5,037,433 A | 8/1991 | Wilk et al. |

(List continued on next page.)

FOREIGN PATENT DOCUMENTS

| | | |
|---|---|---|
| EP | 0 637 431 | 2/1995 |
| WO | 95/13021 | 5/1995 |

*Primary Examiner*—Eduardo C. Robert
(74) *Attorney, Agent, or Firm*—Kenyon & Kenyon

(57) ABSTRACT

A device for sealing a puncture in an anatomical structure includes a proximal portion having a first needle lumen extending to a first needle opening, a distal portion including a second needle opening facing the first needle opening across a tissue receiving gap and opening into a second needle lumen and a connecting portion coupled between the proximal and distal portions and offset from the proximal and distal portions whereby, when the connecting portion is received within a puncture in an anatomical structure, a portion of the anatomical structure received within the tissue receiving gap is located on one side of a plane including a central axis of the puncture.

A method for sealing a puncture in an anatomical structure comprises the steps of inserting into the puncture a device including a needle exit opening and a needle entry opening separated by a tissue receiving gap, positioning the device so that the needle exit opening is located on a proximal side of the anatomical structure and the needle entry opening is located on a distal side of the anatomical structure with a first portion of the anatomical structure received within the tissue receiving gap and inserting a first needle coupled to a first portion of suture distally through the device to penetrate the anatomical structure and re-enter the device via the needle entry lumen. The device is then rotated so that a second portion of the anatomical structure is located within the tissue receiving gap between the needle exit and needle entry lumens and second needle is inserted distally through the device to penetrate the second portion of the anatomical structure and re-enter the device via the needle entry lumen. The device is withdrawn from the patient and the suture is tightened to seal the puncture.

19 Claims, 53 Drawing Sheets

U.S. PATENT DOCUMENTS

| | | | |
|---|---|---|---|
| 5,080,663 A | | 1/1992 | Mills et al. |
| 5,108,421 A | | 4/1992 | Fowler |
| 5,292,327 A | * | 3/1994 | Dodd et al. .................. 606/148 |
| 5,304,184 A | | 4/1994 | Hathaway et al. |
| 5,312,360 A | | 5/1994 | Behl |
| 5,312,423 A | | 5/1994 | Rosenbluth et al. |
| 5,320,632 A | | 6/1994 | Heidmueller |
| 5,324,306 A | | 6/1994 | Makower |
| 5,336,229 A | * | 8/1994 | Noda ......................... 606/144 |
| 5,336,231 A | | 8/1994 | Adair |
| 5,350,385 A | * | 9/1994 | Christy ....................... 606/139 |
| 5,364,408 A | | 11/1994 | Gordon |
| 5,368,601 A | | 11/1994 | Sauer et al. |
| 5,374,275 A | | 12/1994 | Bradley et al. |
| 5,383,896 A | | 1/1995 | Gershony et al. |
| 5,387,221 A | | 2/1995 | Bisgaard |
| 5,391,182 A | | 2/1995 | Chin |
| 5,391,183 A | | 2/1995 | Janzen et al. |
| 5,403,329 A | | 4/1995 | Hinchcliffe |
| 5,417,699 A | | 5/1995 | Klein et al. |
| 5,431,666 A | | 7/1995 | Sauer et al. |
| 5,437,631 A | | 8/1995 | Janzen |
| 5,447,502 A | | 9/1995 | Haaga |
| 5,458,609 A | | 10/1995 | Gordon et al. |
| 5,462,561 A | * | 10/1995 | Voda ........................... 606/144 |
| 5,474,543 A | | 12/1995 | McKay |
| 5,476,469 A | | 12/1995 | Hathaway et al. |
| 5,527,322 A | | 6/1996 | Klein |
| 5,578,044 A | | 11/1996 | Gordon et al. |
| 5,613,974 A | | 3/1997 | Andreas |
| 5,676,689 A | | 10/1997 | Kensey |
| 5,700,273 A | | 12/1997 | Buelna et al. |
| 5,713,910 A | | 2/1998 | Gordon et al. |
| 5,720,757 A | | 2/1998 | Hathaway et al. |
| 5,728,133 A | | 3/1998 | Kontos |
| 5,779,719 A | | 7/1998 | Klein et al. |
| 5,792,152 A | | 8/1998 | Klein et al. |
| 5,810,849 A | * | 9/1998 | Kontos ....................... 606/148 |
| 5,810,850 A | | 9/1998 | Hathaway et al. |
| 5,814,065 A | | 9/1998 | Diaz |
| 5,820,631 A | | 10/1998 | Nobles |
| 5,830,125 A | | 11/1998 | Scribner et al. |
| 5,843,098 A | | 12/1998 | Allen et al. |
| 5,846,253 A | | 12/1998 | Buelna et al. |
| 5,855,585 A | * | 1/1999 | Kontos ....................... 606/148 |
| 5,860,990 A | | 1/1999 | Nobles et al. |
| 5,868,762 A | | 2/1999 | Cragg et al. |
| 5,876,411 A | * | 3/1999 | Kontos ....................... 606/148 |
| 5,902,311 A | | 5/1999 | Andreas et al. |
| 5,910,155 A | | 6/1999 | Ratcliff et al. |
| 5,921,994 A | | 7/1999 | Andreas et al. |
| 5,928,266 A | | 7/1999 | Kontos |
| 5,972,005 A | * | 10/1999 | Stalker et al. ............... 606/144 |
| 5,997,555 A | * | 12/1999 | Kontos ....................... 606/199 |
| 6,036,699 A | | 3/2000 | Andreas et al. |

* cited by examiner

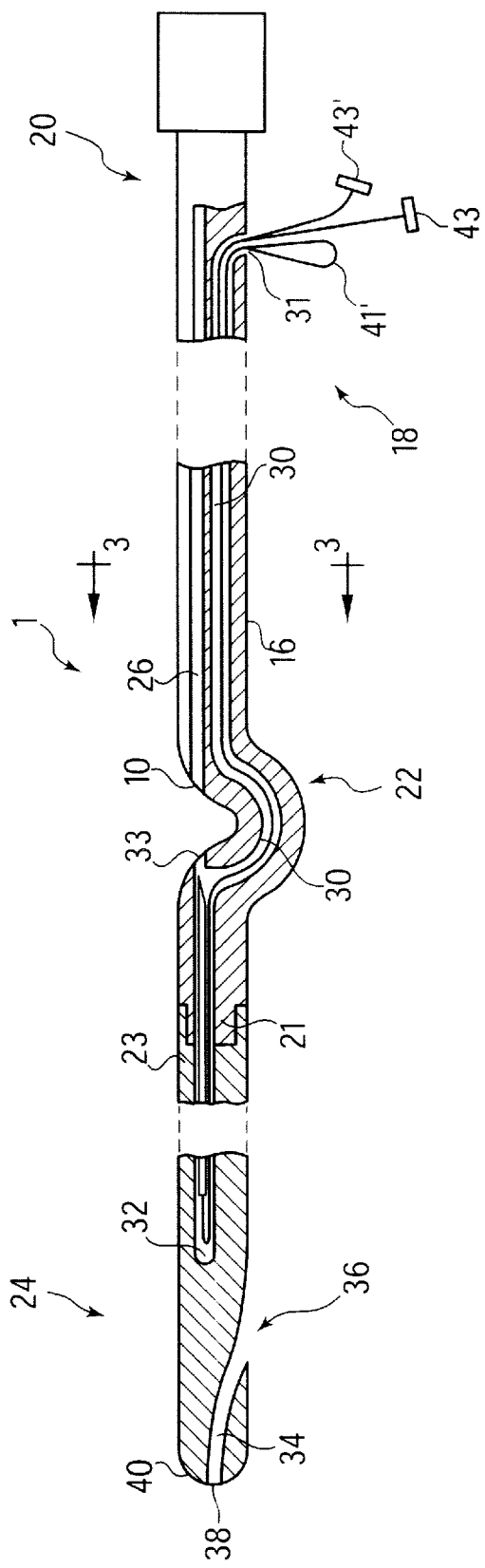
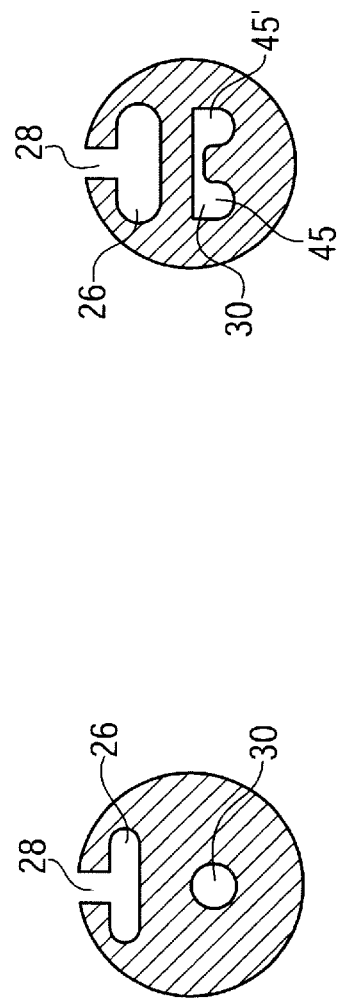
FIG. 1
FIG. 3A
FIG. 3B

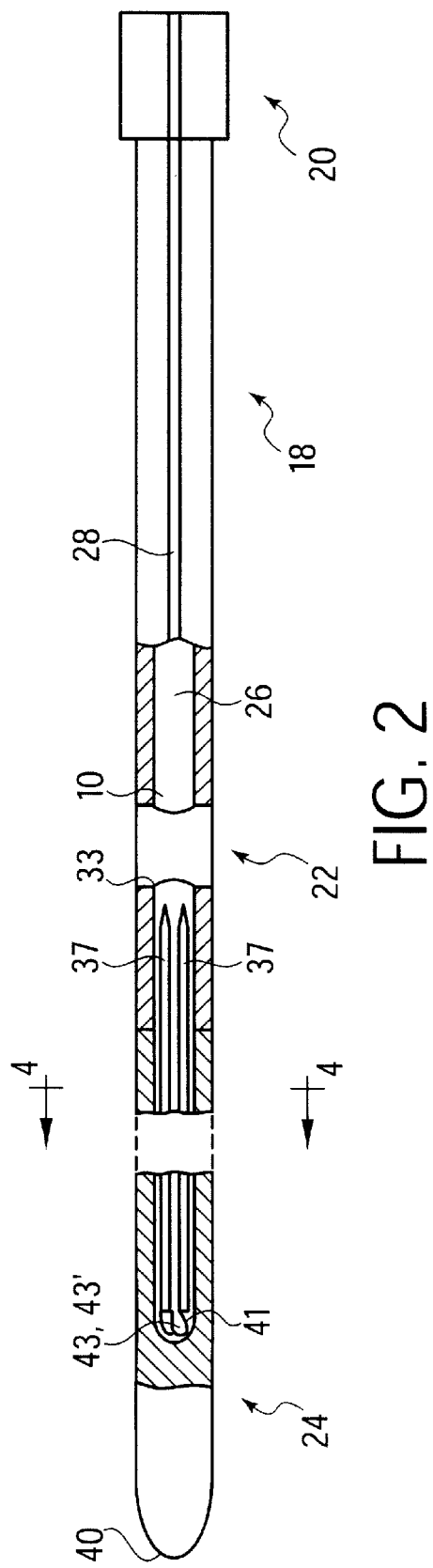
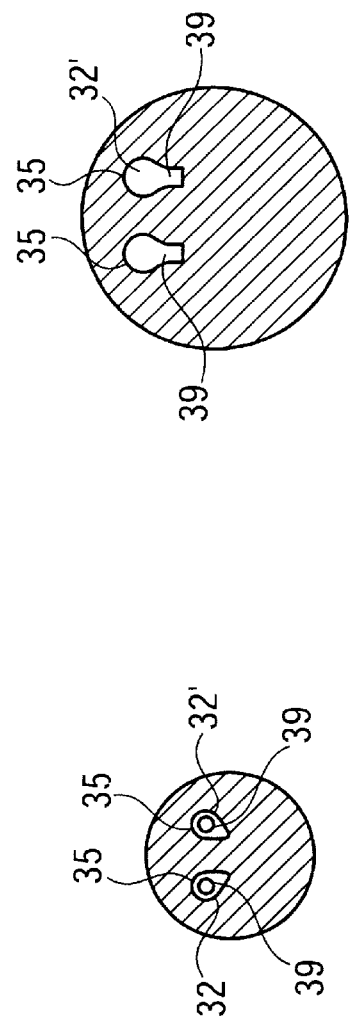
FIG. 2
FIG. 4A
FIG. 4B

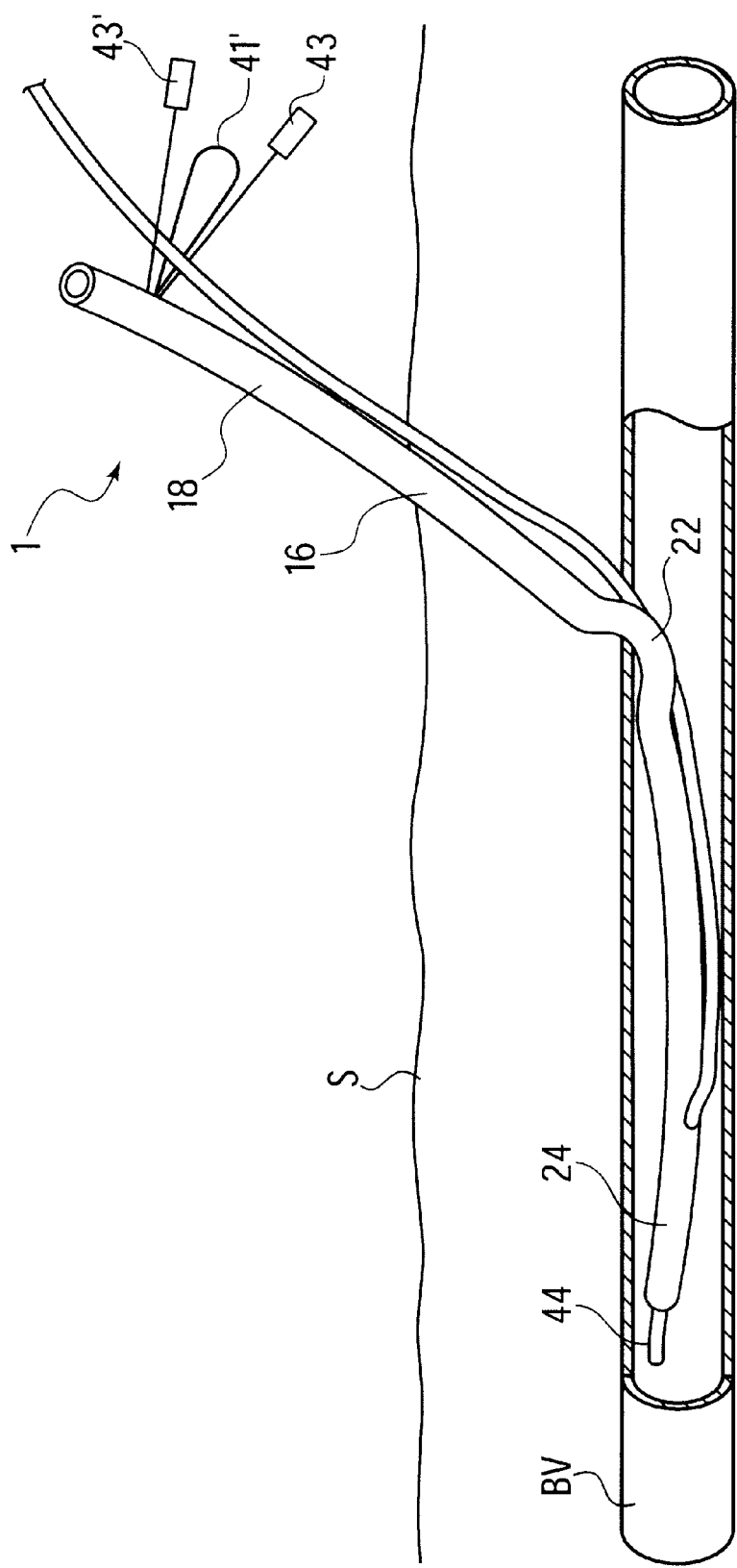

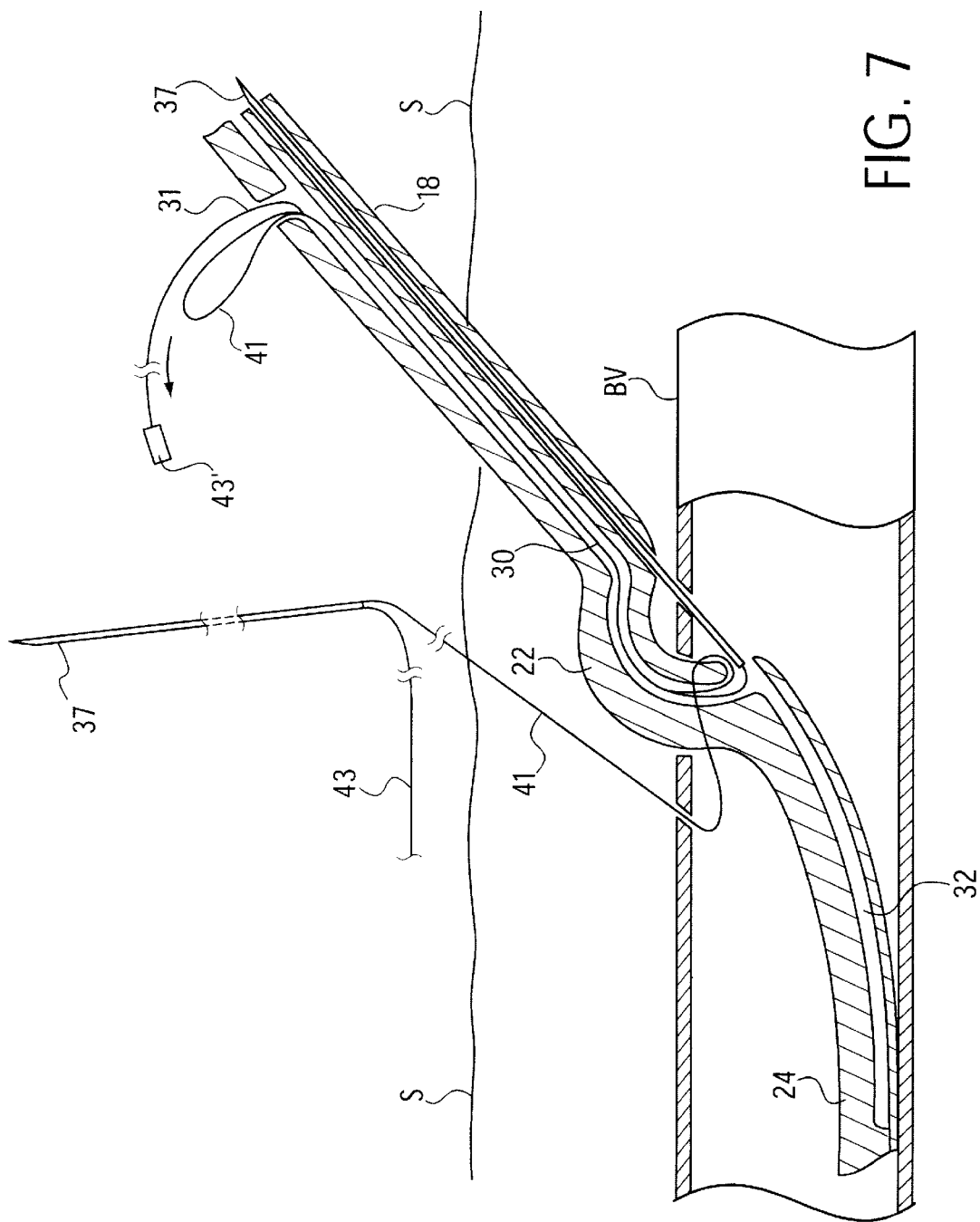

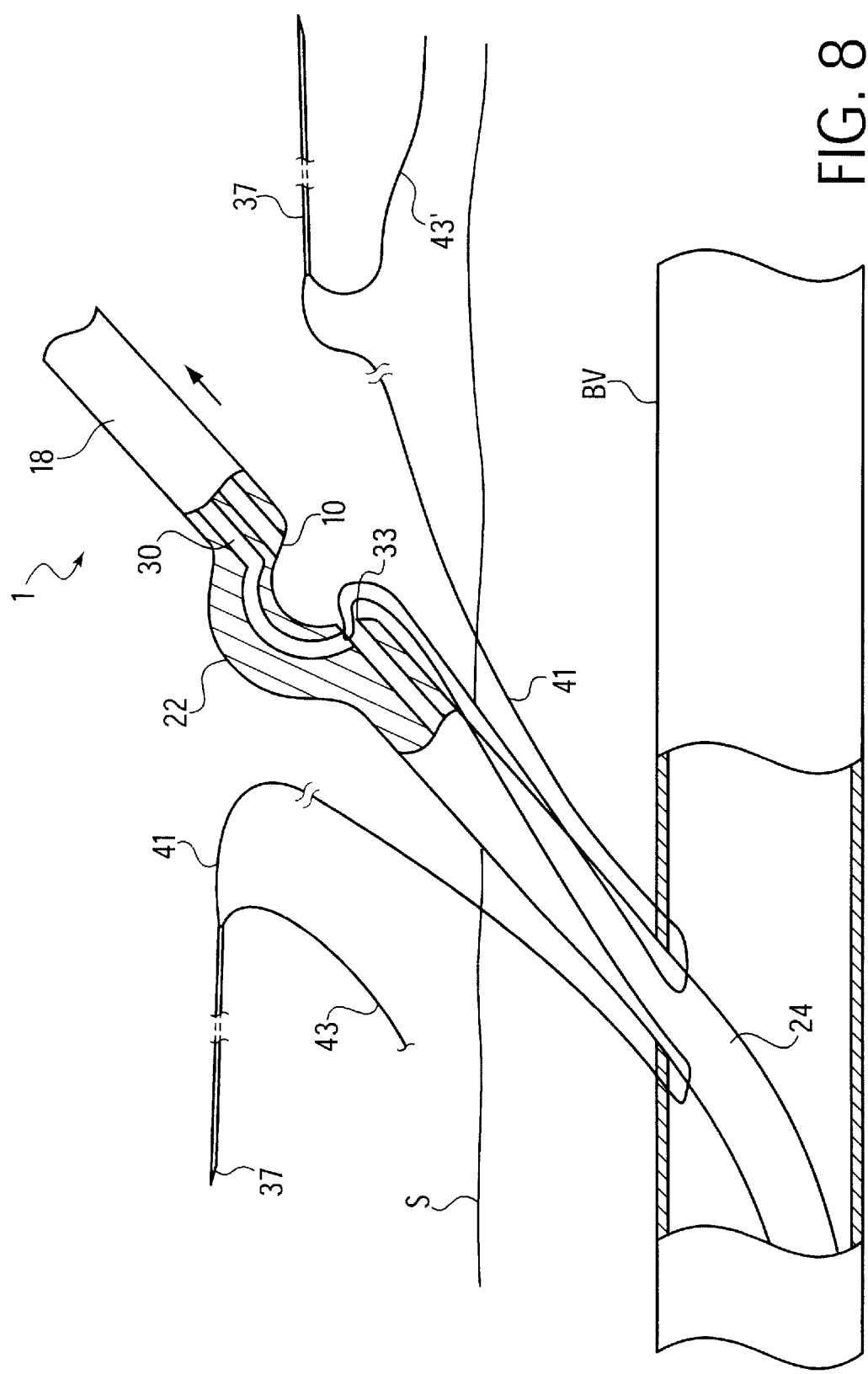

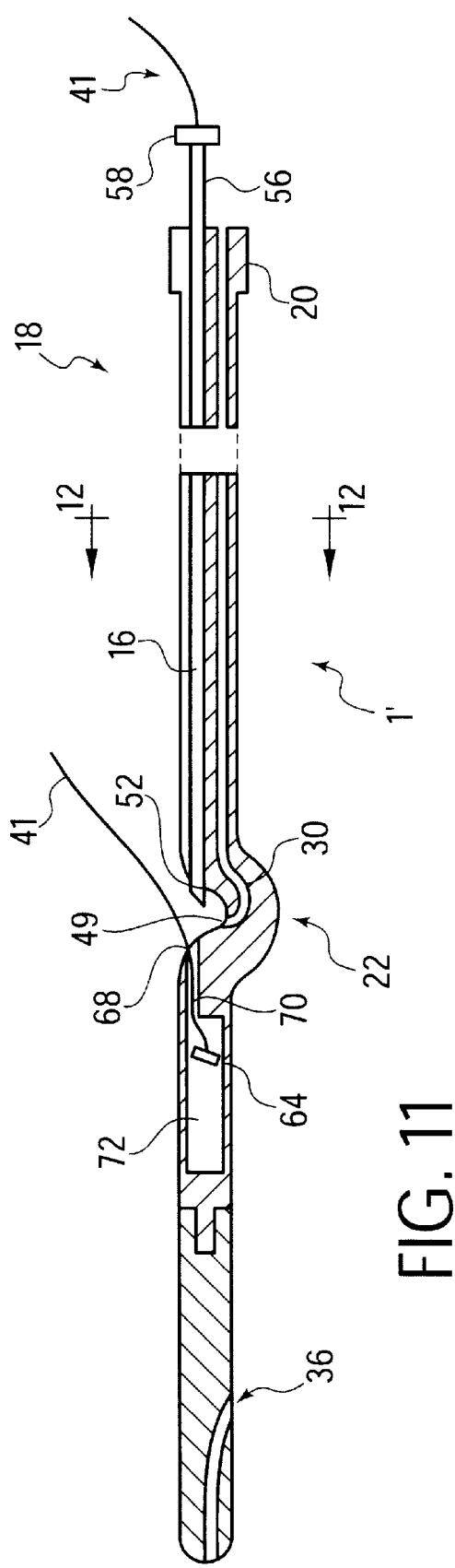
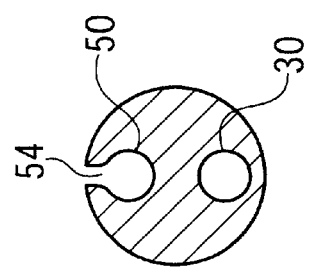
FIG. 11
FIG. 12

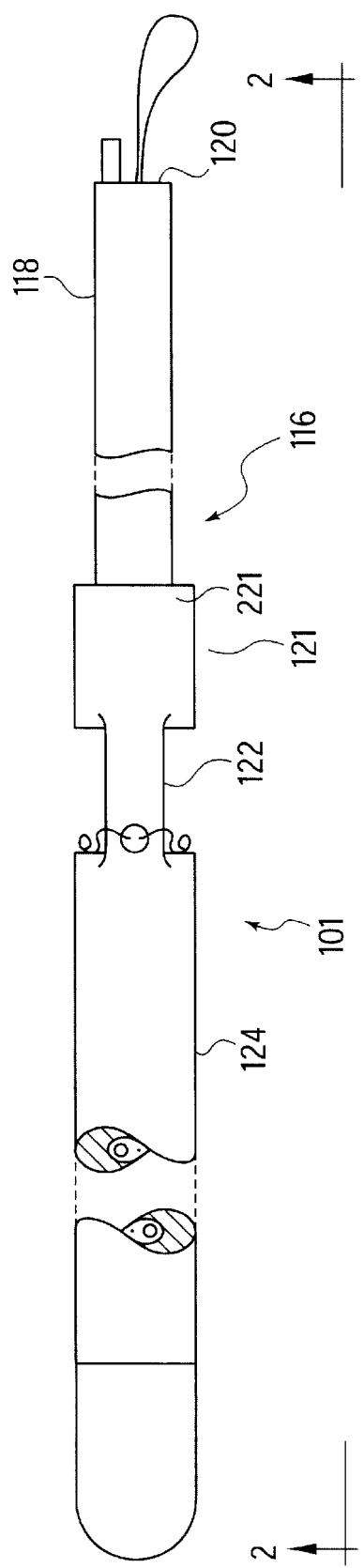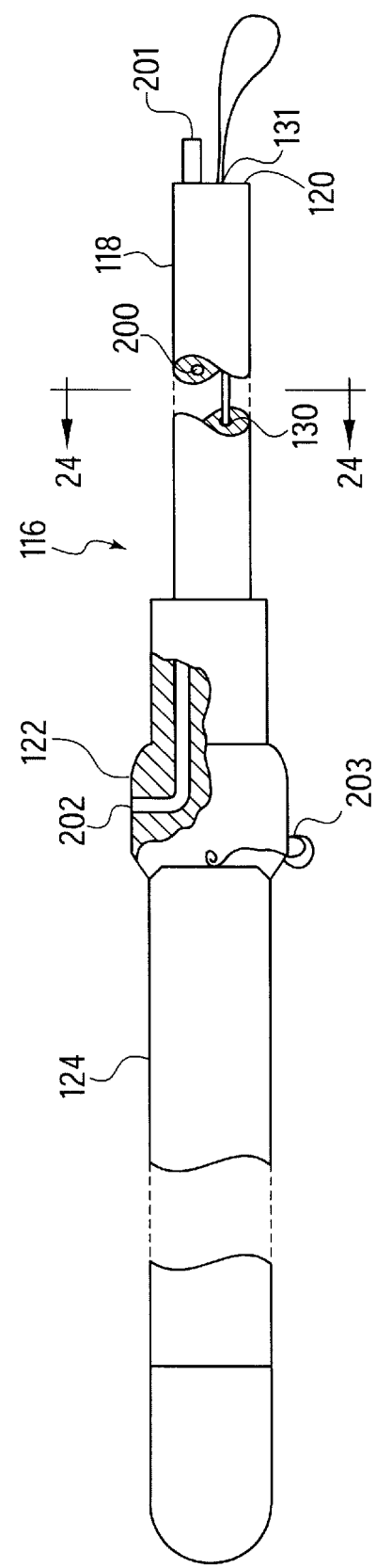

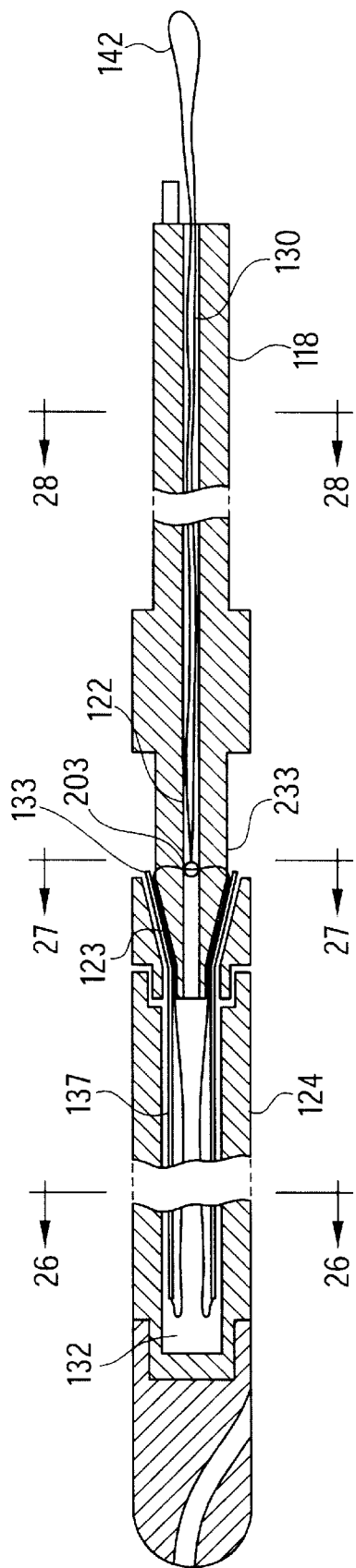
FIG. 25
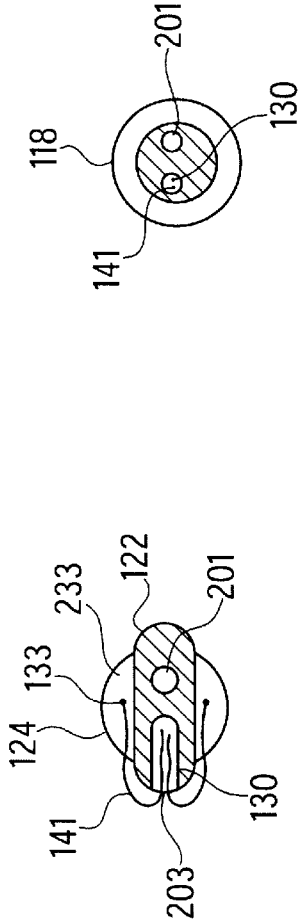
FIG. 28
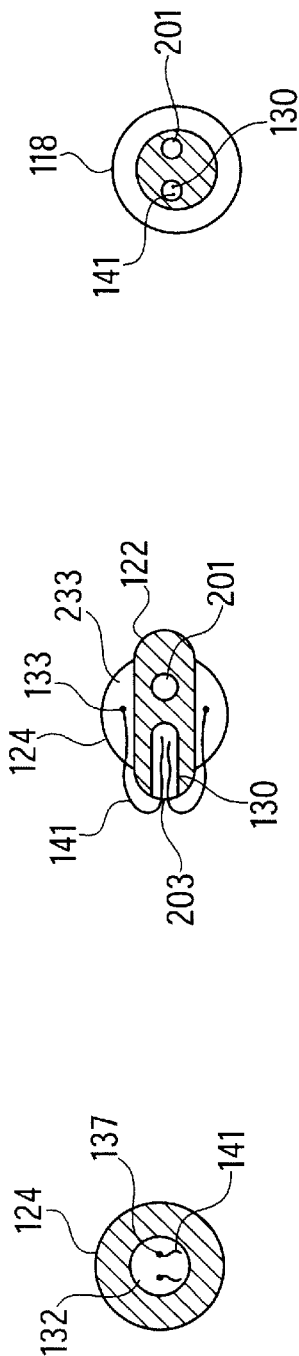
FIG. 27
FIG. 26

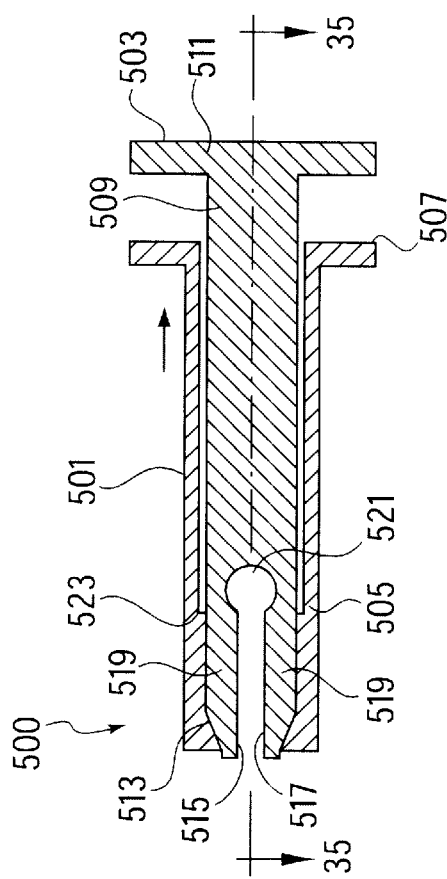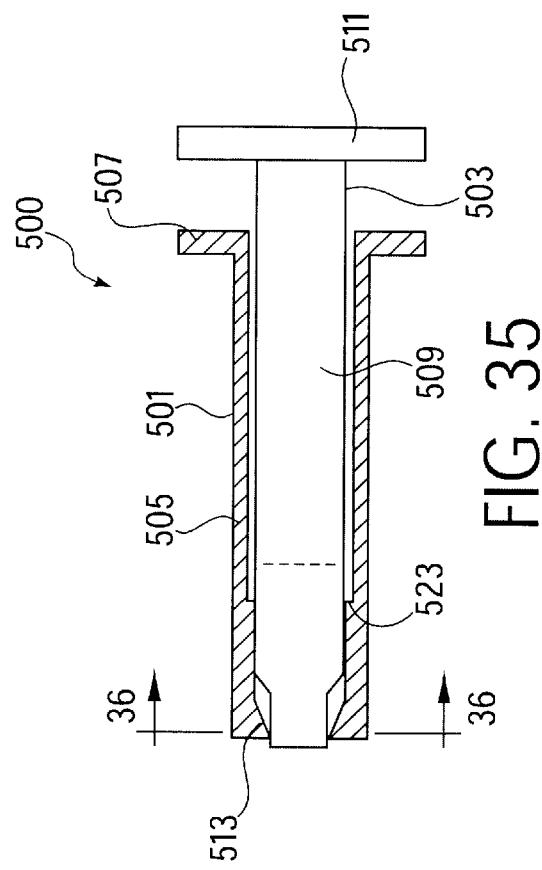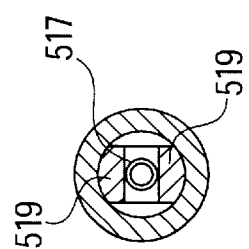

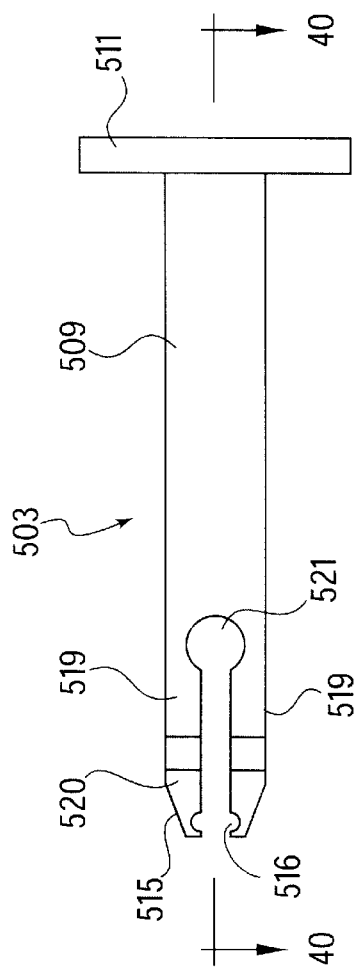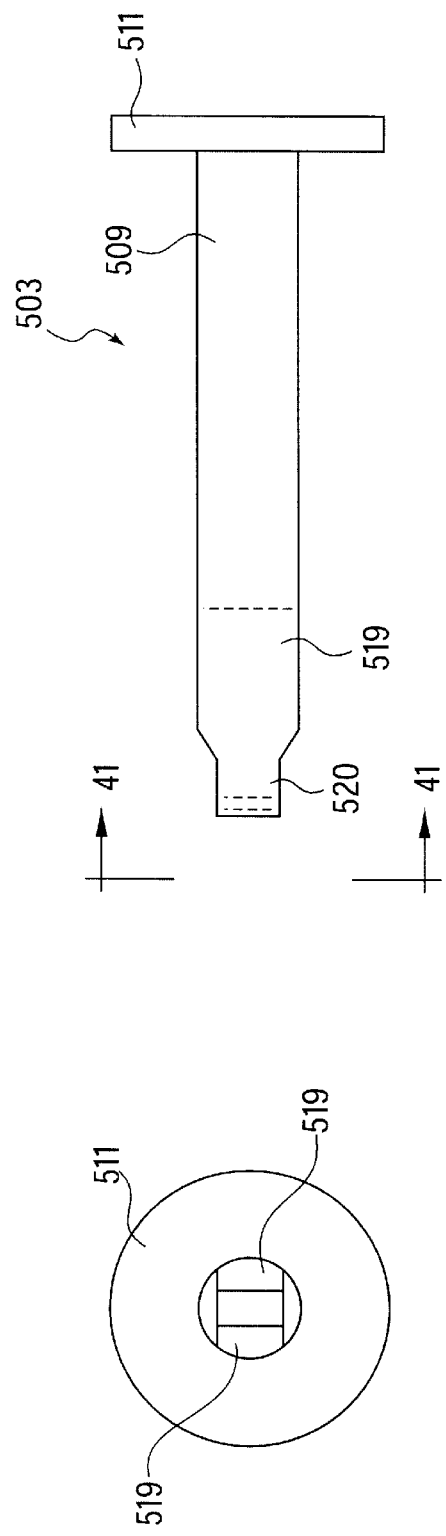
FIG. 39
FIG. 40
FIG. 41

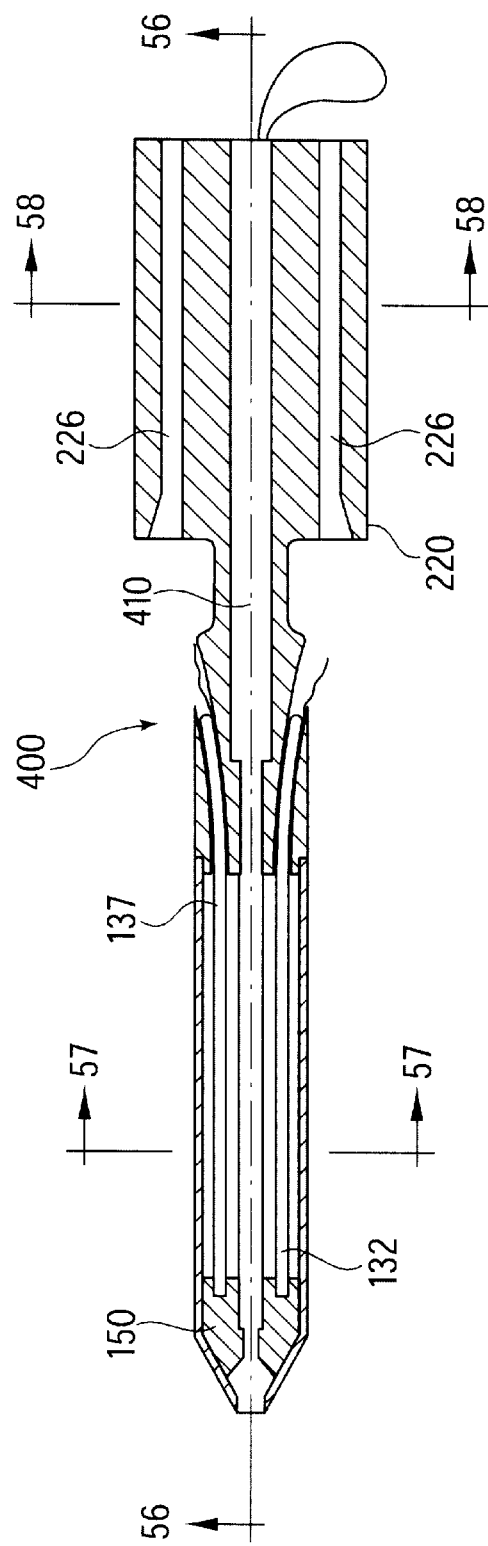
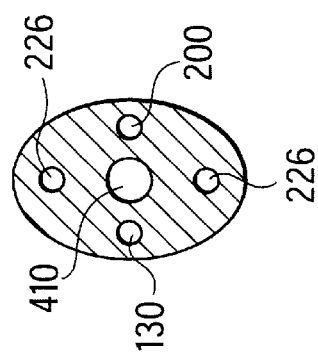
FIG. 55
FIG. 58

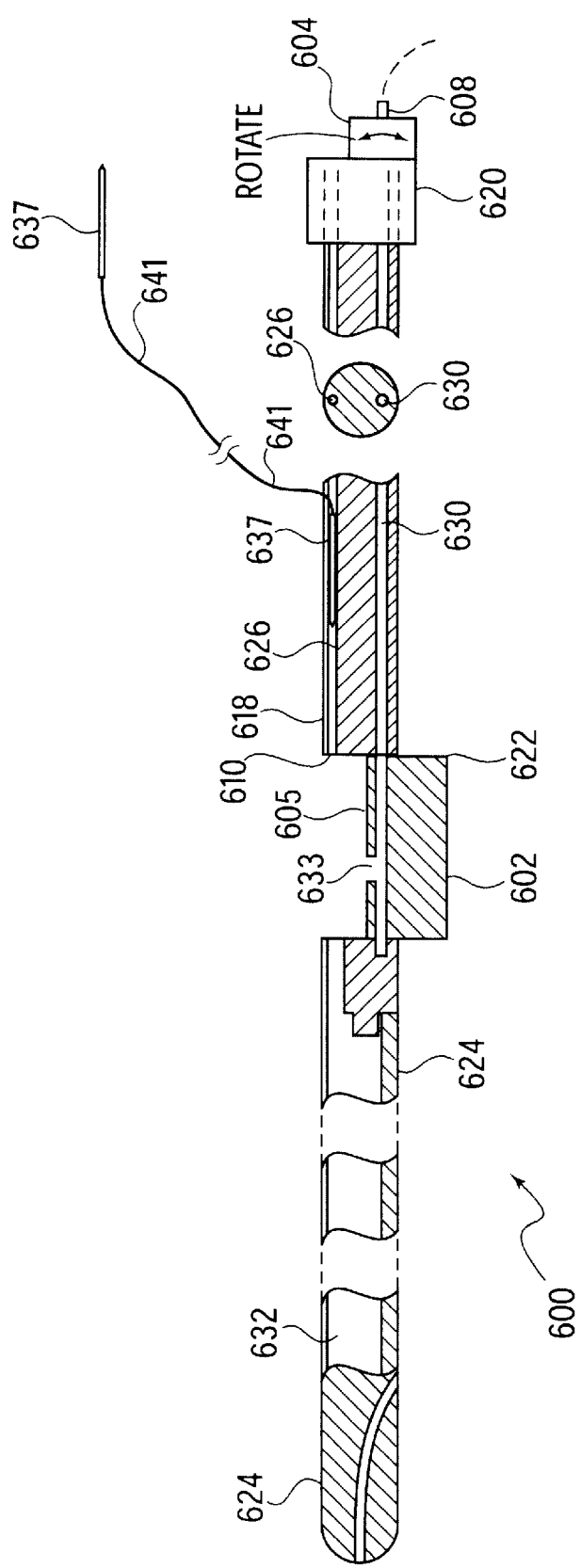
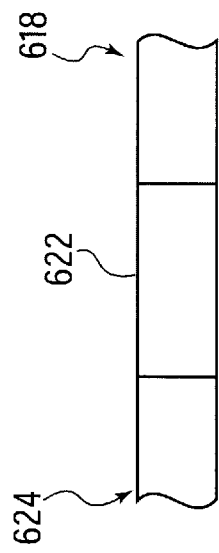
FIG. 71
FIG. 72

DEVICE AND METHOD FOR SUTURING BLOOD VESSELS AND THE LIKE

This application is a CIP of Ser. No. 09/126,316 filed Jul. 30, 1990, now U.S. Pat. No. 6,024,747 which is a CIP of application Ser. No. 08/661,884 filed Jun. 11, 1996 now U.S. Pat. No. 6,000,792.

FIELD OF THE INVENTION

The present invention relates generally to surgical instruments, and more specifically to devices for the suturing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument such as a catheter into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the opening in the wall of the blood vessel must be sealed to prevent bleeding while facilitating healing of the wound. This sealing has commonly been accomplished by the application of direct pressure over the puncture site by a physician or other trained medical professional. However, this technique is time consuming and may lead to complications such as thrombosis, which may be dangerous to the patient.

Other sealing techniques include the application of a sealing member or plug of material (most often biogenic sealing material) over the opening in the blood vessel to seal the wound. However, proper placement of sealing members and plugs is difficult to achieve and materials left inside the body may pose serious health risks to the patient if, for example, the material enters the blood stream.

SUMMERY OF THE INVENTION

The present invention is directed to a device for sealing a puncture in an anatomical structure comprising a proximal portion having a first needle lumen extending therethrough to a first needle opening, a distal portion including a second needle opening facing the first needle opening across a tissue receiving gap and opening into a second needle lumen and a connecting portion coupled between the proximal and distal portions and offset from the proximal and distal portions to create the tissue receiving gap whereby, when the connecting portion is received within a puncture in an anatomical structure, a portion of the anatomical structure received within the tissue receiving gap is located on one side of a plane including a central axis of the puncture.

In addition, the present invention is directed to a method for sealing an opening in an anatomical structure comprising the steps of inserting into the opening a device including a needle exit opening and a needle entry opening separated by a tissue receiving gap and positioning the device so that the needle exit opening is located on a proximal side of the anatomical structure and the needle entry opening is located on a distal side of the anatomical structure with a first portion of the anatomical structure received within the tissue receiving gap. A first needle coupled to a first portion of suture is inserted distally through the device to exit the device via the needle exit opening, penetrate the first portion of the anatomical structure and reenter the device via the needle entry lumen and the device is rotated so that a second portion of the anatomical structure is located within the tissue receiving gap between the needle exit and needle entry lumens. Then a second needle coupled to a second portion of suture is inserted distally through the device to exit the device via the needle exit opening, penetrate the second portion of the anatomical structure and re-enter the device via the needle entry lumen. the device is withdrawn from the anatomical structure and the first and second portions of suture are tightened to draw the sides of the opening together.

BRIEF DESCRIPTION OF THE DRAWINGS

FIG. 1 shows a side view of a cross-section of a suturing device according to a first embodiment of the invention;

FIG. 2 shows a top view of a cross-section of a suturing device according to the first embodiment of the invention;

FIG. 3A shows a cross-section of a device according to the first embodiment of the invention taken along line 3—3 of FIG. 1;

FIG. 3B shows an alternative cross-section of a device according to the first embodiment of the invention taken along line 3—3 of FIG. 1;

FIG. 4A shows a cross-section of a device according to the first embodiment of the invention taken along line 4—4 of FIG. 2;

FIG. 4B shows an alternative cross-section of a device according to the first embodiment of the invention taken along line 4—4 of FIG. 2;

FIG. 6A shows a partially cross-sectional view of the blood vessel with a device according to the first embodiment of the present invention received on the guide wire in a first desired position;

FIG. 7 shows a partially cross-sectional view of the blood vessel with a device according to the first embodiment of the present invention in a second desired position;

FIG. 8 shows a partially cross-sectional view of the blood vessel with a device according to the first embodiment of the present invention partially removed from the blood vessel;

FIG. 11 shows a side view of a cross-section of a suturing device according to a second embodiment of the invention;

FIG. 12 shows a cross-section of a device according to the second embodiment of the invention taken along line 12—12 of FIG. 11;

FIG. 22 shows a side view of a fifth embodiment of the suture device according to the present invention;

FIG. 23 shows a side view of the suture device of FIG. 22, with the device rotated 90° from the position shown in FIG. 22;

FIG. 25 shows a side view of the suture device of FIG. 22;

FIG. 26 shows a cross-sectional view of the suture device of FIG. 25 taken along the line 26—26;

FIG. 27 shows a cross-sectional view of the suture device of FIG. 25 taken along the line 27—27;

FIG. 28 shows a cross-sectional view of the suture device of FIG. 25 taken along the line 28—28;

FIG. 34 shows a cross-sectional view of a suture crimping device according to the present invention;

FIG. 35 shows a cross-sectional view of the suture crimping device of FIG. 34 taken along line 35—35 of FIG. 34;

FIG. 36 shows a cross-sectional view of the suture crimping device of FIG. 34 taken along line 36—36 of FIG. 35;

FIG. 39 shows a side view of a piston according to the present invention;

FIG. 40 shows a side view of the piston of FIG. 39 taken along line 40—40 of FIG. 39;

FIG. 41 shows a front view of the piston of FIG. 39 taken along line 41—41 of FIG. 40;

FIG. 55 shows a cross-sectional view of a further exemplary embodiment of a suture device according to the present invention;

FIG. 58 shows a cross-sectional view of the suture device of FIG. 55 taken along line 58—58 of FIG. 55;

FIG. 71 shows a side view of a cross-section of a suturing device according to an additional embodiment of the invention;

FIG. 72 shows the suturing device of FIG. 71 before entering the blood vessel;

DETAILED DESCRIPTION OF THE INVENTION

Figure 5:
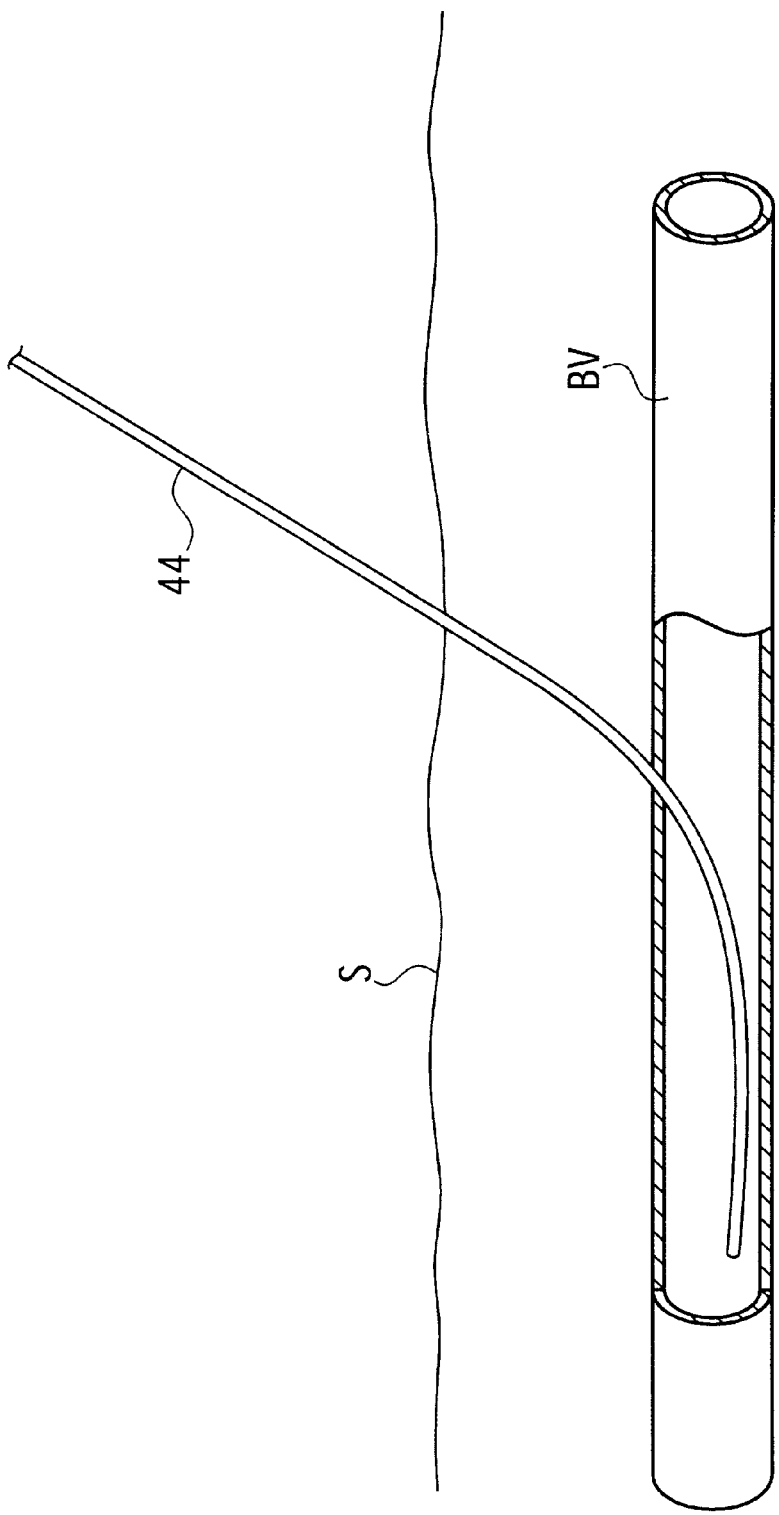
FIG. 5 shows a partially cross-sectional view of a blood vessel within a body with a guide wire inserted therein.

Referring now to the drawings, in which like reference numerals identify similar or identical elements, FIGS. 1–8 show a device 1 according to a first embodiment of the invention for suturing punctures in blood vessels, internal organs and the like. The device 1 includes flexible tube 16 of substantially circular cross-section, which has a proximal part 18 and a distal part 24. The proximal part 18 extends from a first end 20 through a central arcuate portion 22 to a second end 21 which mates with a proximal end 23 of the distal part 24. The central arcuate portion may preferably be substantially circular with a radius of from 0.100" to 0.600". The flexible tube 16 is preferably constructed of a thermoplastic such as polyurethane, polyethylene, or the like, in two or three parts bonded together. The various parts of the flexible tube 16 may preferably be either extruded or molded. Those skilled in the art will recognize that it will be more economical to extrude the parts including one or two lumens, while the more complex, and curved sections of the flexible tube 16 may be molded. The length of the flexible tube may be selected to fit the requirements of a particular situation and is preferably between 1" and 16" in length.

The flexible tube 16 includes a large interior needle withdrawal lumen 26 which extends through the proximal part 18 from the first end 20 to an opening 10 at a proximal end of the central arcuate portion 22. As seen in FIGS. 3A and 3B, the needle withdrawal lumen 26 may preferably be oval in cross-section and may include an optional slot 28 opening to the outside of the flexible tube 16.

In addition, a flash back lumen 30 extends from an opening 31 formed in the proximal part 18 through the central arcuate portion 22 to open into two needle retention bores 32 and 32' formed side-by-side in the distal part 24. As seen in FIG. 3A, the flash back lumen 30 may be circular in cross-section and is sized to simultaneously accommodate two strands of the suture 41 and the two pull cords 43 and 43'. However, as shown in FIG. 3B, the cross-section of the flash back lumen 30 may preferably include side-by-side hemispherical channels 45 and 45' for receiving the loop 41' of the suture 41 and the two pull cords 43 and 43'. This helps to ensure that the second needle 37 is not accidentally drawn out of the needle retention bore 32' when the first 37 is being pulled out. The needle retention bores 32 and 32' extend from distal ends to openings 33 and 33', respectively, formed at a position in the distal end of the central arcuate portion 22 opposite the opening 10. In addition, a substantially straight stiffening member may be inserted into the flash back lumen 30 in order to straighten the central arcuate portion 22 during insertion of the device 1 into the body. Alternatively, the device 1 may be made straight and, after insertion into the body, a curved stiffening member may be inserted to bend the device 1 thereby creating the central arcuate portion 22.

As seen in FIGS. 4A and 4B, the retention bores 32 and 32' have cross-sectional shapes including first portions 35, each shaped to receive a needle 37 and second portions 39, each shaped to receive a suture 41 and pull cord 43 or 43'. The first portions 35 are shaped to correspond to the cross-section of the needles 37 which in the preferred embodiment is substantially circular. The second portions 39, which are of reduced size so that the needles 37 are unable to enter, may be either rectangular or triangular projections extending from the first portions 35 and are sufficiently large to simultaneously accommodate the suture 41 and one of the pull cords 43 and 43'. The suture 41, which will preferably be in the range of 0.004" to 0.010" in diameter and from 15" to 35" in length, may be formed of either "reabsorbable" or "non-reabsorbable" material, as is well known in the art. The pull cords 43 and 43' will preferably be formed of non-reabsorbable material and will be of similar diameter to the suture 41. Those skilled in the art will recognize that the function of the pull cords 43 and 43' may be filled by a loop 41' of the suture 41 coupled between the distal ends of the needles 37 extended through the flash back lumen 30 so that, when the loop 41' of the suture 41 is extended proximally, the needles 37 are urged proximally through the needle retention bores 32 and 32'.

As the device 1 according to the first embodiment includes a single pair of needles, this device should preferably be used to close punctures of 9.0 French size and smaller (each French size representing 0.13" in diameter). The flexible tube 16 will, therefore, preferably be 6.0 or 8.0 French size. As described below in reference to further embodiments of the invention, devices employing two or more pairs of needles 37 may be employed to close punctures larger than 9.0 French size. Each of the needles 37 may preferably be constructed of stainless steel, be between 2" and 8" in length and have a diameter between 0.010" and 0.030".

When the device 1 is in an operative configuration, the suture 41 extends between the distal ends of two needles 37 received in the needle retention bores 32 and 32'. In the first embodiment of the invention, optional pull cords 43, 43' extend from the distal end of each of the needles 37 through the second portions 39 of the needle retention bores 32 and 32', via the flash back lumen 30, to the opening 31. However, the suture 41 may, alternatively, extend from the distal ends of the needles 37 through the second portions 39 of the needle retention bores 32 and 32', via the flash back lumen 30, to the opening 31 so that a portion of the suture loop 41' which extends out from the opening 31 may provide the function of the pull cords 43 and 43', as described below.

Finally, a guide wire lumen 34 extends through the distal part 24 of the device 1 from a proximal opening 36 to a distal opening 38 formed in a second end 40 of the device 1.

In operation, as shown in FIGS. 5–10, when an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 44 is inserted through the puncture to a target area within the blood vessel and a catheter is inserted through the introducer sheath, along the guide wire 44, to a target area within the blood vessel. After the procedure is complete, the catheter and the introducer sheath are withdrawn and the guide wire 44 is left in place. A proximal end of the guide wire 44 is then inserted through the guide wire lumen 34 and the device 1 is inserted into the body and moved along the guide wire 44 through the puncture until the central arcuate portion 22 straddles a portion of the blood vessel wall adjacent to the puncture.

By observing the flash back lumen 30 and the needle withdrawal lumen 26, the doctor may determine when the device 1 is in the desired position. Specifically, when the device 1 is inserted far enough into the blood vessel, blood will be observed in the flash back lumen 30. However, if blood is observed in the needle withdrawal lumen 26, the doctor knows that the device 1 has been inserted too far into the blood vessel.

As the device 1 is inserted into the blood vessel, the flexible tube 16 bends so that the device 1 is received within, and extends in the direction of the blood vessel without straining the vessel. In this position, the openings 33 and 33' are on the distal side of the puncture facing the opening 10 which is located on the proximal side of the puncture.

Figure 6B:
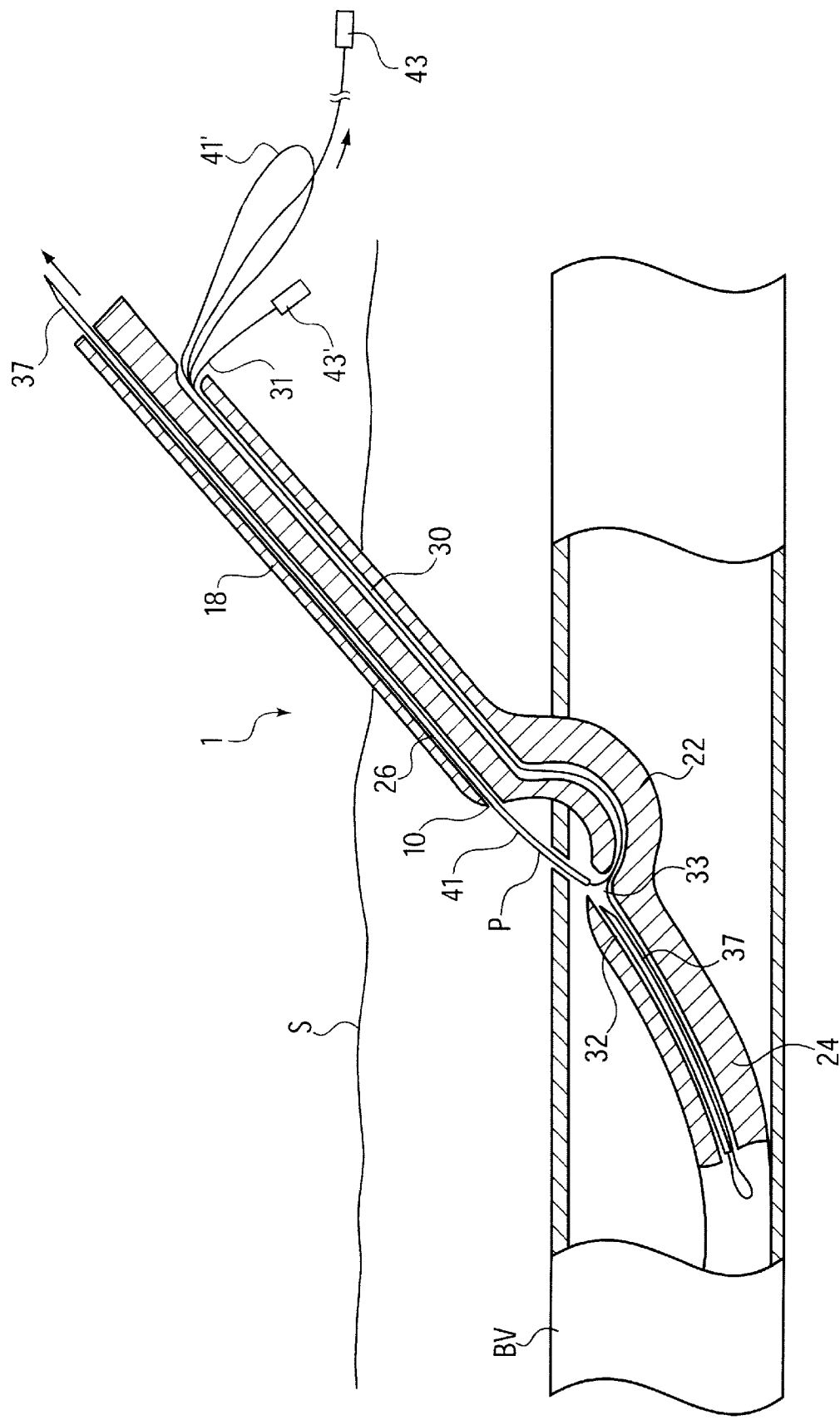
FIG. 6B shows a partially cross-sectional view of the blood vessel with the device as shown in FIG. 6A wherein a needle has been drawn through the body tissue received in the central gap.

As shown in FIG. 6B, the doctor then rotates the device 1 into a desired orientation and draws the pull cord 43 out of the opening 31, thus drawing one of the needles 37 forward through the needle retention bore 32 so that a pointed, proximal end of the needle 37 is drawn through the wall of the blood vessel, enters the opening 10 and extends into the needle withdrawal lumen 26. The needle 37 is then withdrawn through the needle withdrawal lumen 26, drawing a first end of the suture 41 through the wall of the blood vessel and into the needle withdrawal lumen 26. The needle 37 is drawn forward by means of the pull cord 43 until a proximal end of the needle 37 protrudes from the proximal end of the needle withdrawal lumen 26. The proximal end of the needle 37 is then grasped by the doctor and withdrawn from the needle withdrawal lumen 26. In order to ensure that the needles 37 will extend through the needle withdrawal lumen 26, the needles 37 will preferably be at least 4" in length.

Thereafter, the doctor rotates the device 1, as shown in FIG. 7, until the central arcuate portion 22 straddles the blood vessel wall in a desired position relative to the point at which the first end of the suture 41 penetrated the blood vessel wall. Those skilled in the art will understand that this "desired position" will usually be on the opposite side of the puncture, so that the device 1 will be rotated approximately 180° after the first needle 37 is withdrawn. When the device 1 is in the second desired orientation, the doctor draws the pull cord 43' out of the opening 31 thereby urging the second needle 37 forward through the needle retention bore 32' so that the pointed, proximal end of the second needle 37 is drawn through the wall of the blood vessel, enters the opening and extends into the needle withdrawal lumen 26. The second needle 37 is withdrawn through the needle withdrawal lumen 26, drawing the second end of the suture 41 through the wall of the blood vessel and into the needle withdrawal lumen 26 as described above.

Figure 9:
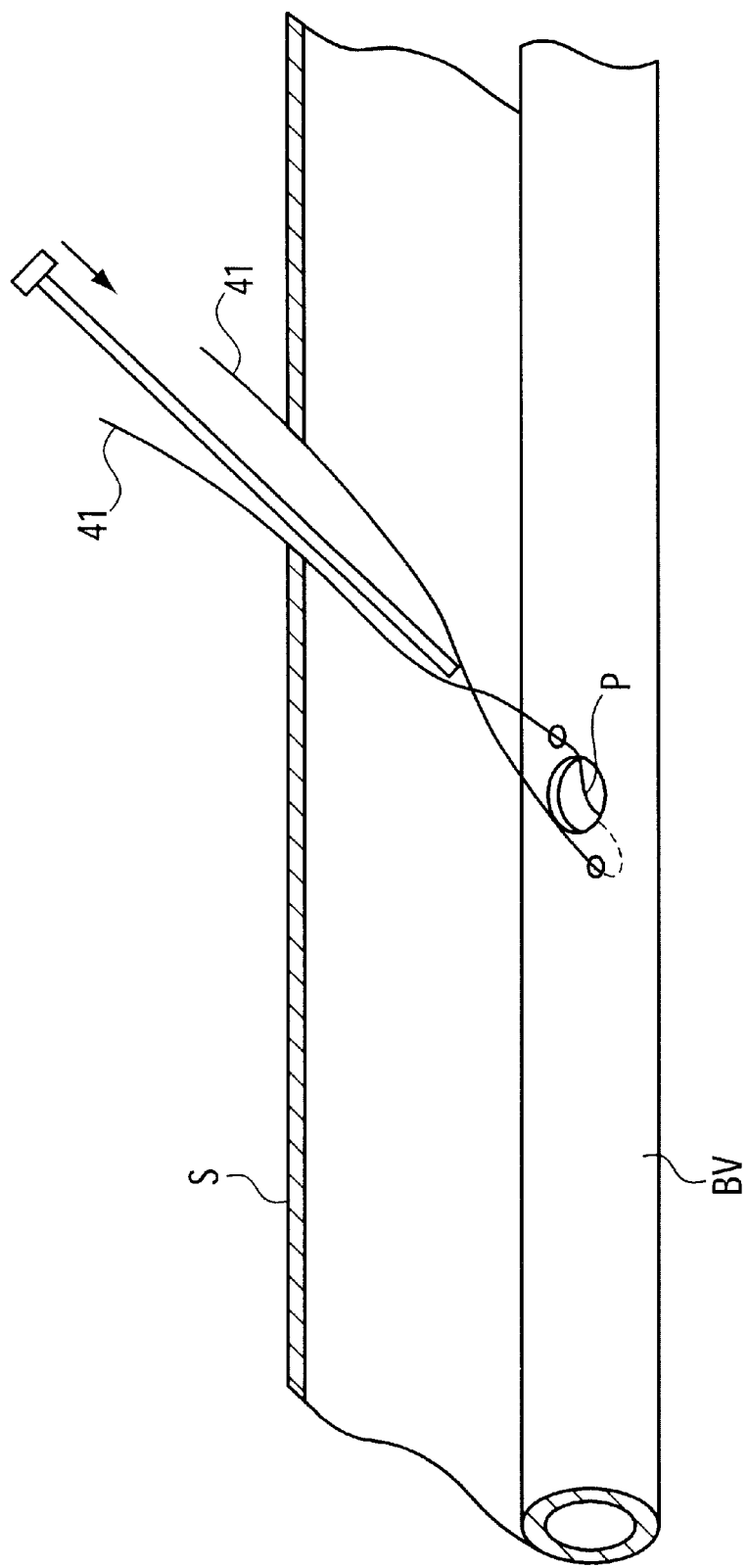
FIG. 9 shows a slip knot tied in a suture loop extending through the wall of the blood vessel being urged toward the blood vessel.
Figure 10:
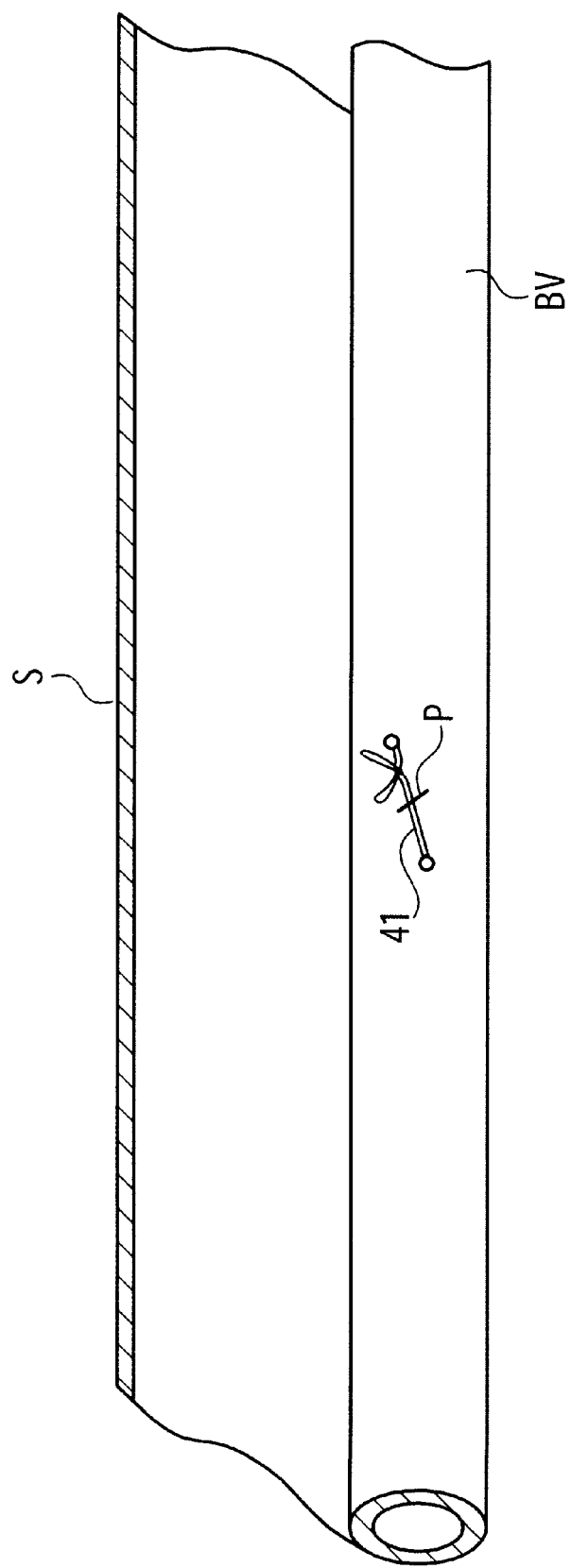
FIG. 10 shows a suture sealing the puncture.
Figure 13:
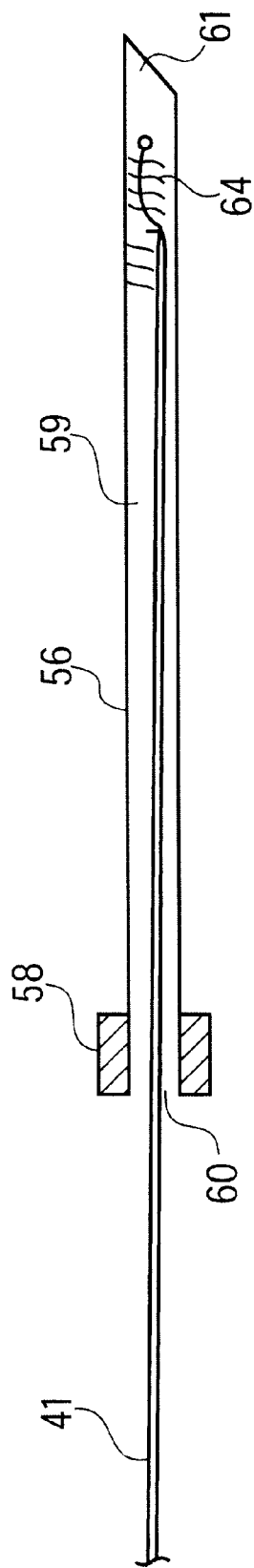
FIG. 13 shows a cross-sectional view of a puncture needle according to the second embodiment of the present invention.
Figure 14:
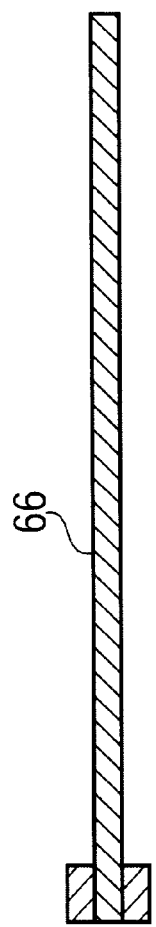
FIG. 14 shows a side view of a plunger according to the second embodiment of the present invention.
Figure 15:
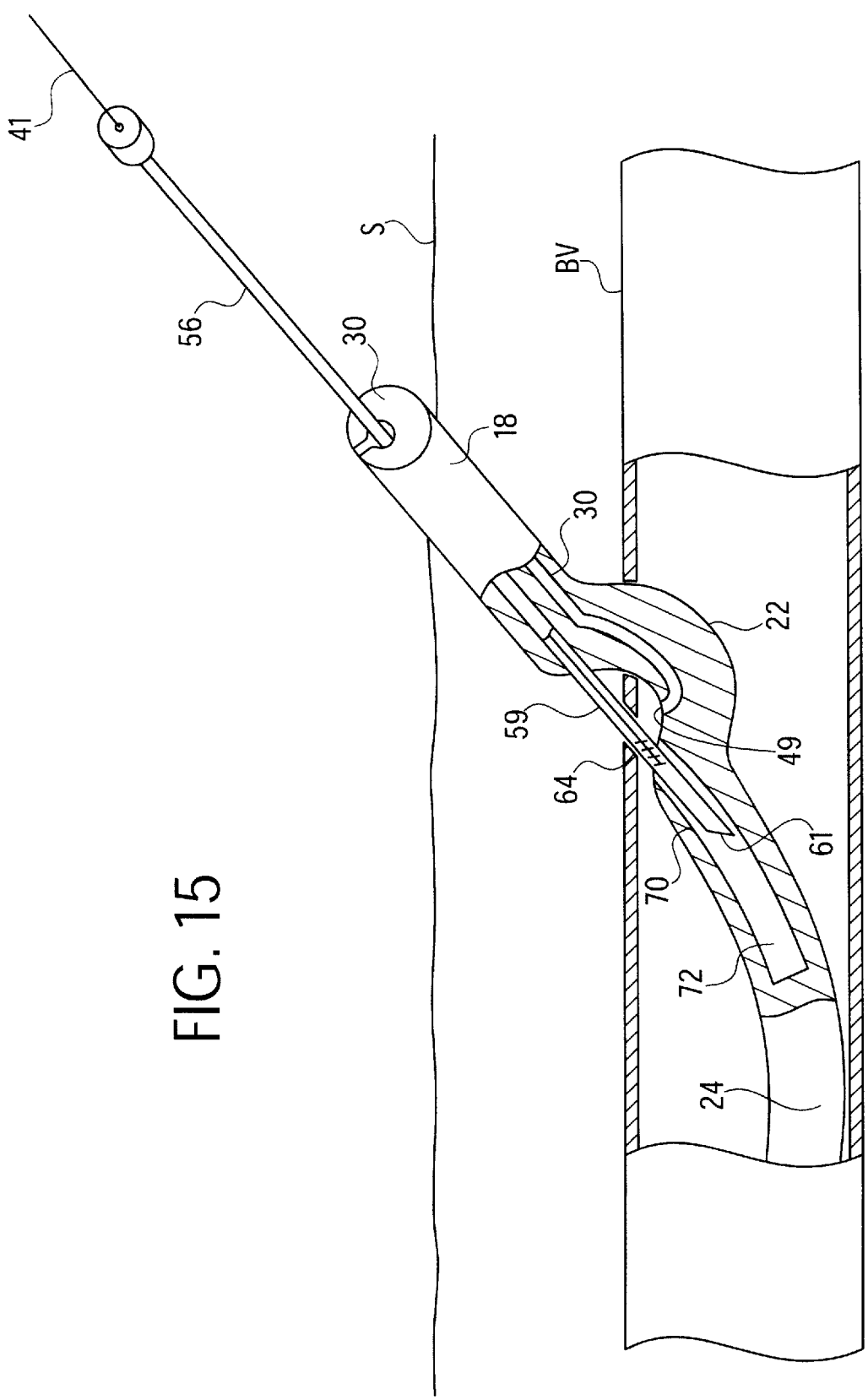
FIG. 15 shows a partially cross-sectional view of the blood vessel with a device according to the second embodiment of the present invention in a first desired position.
Figure 16:
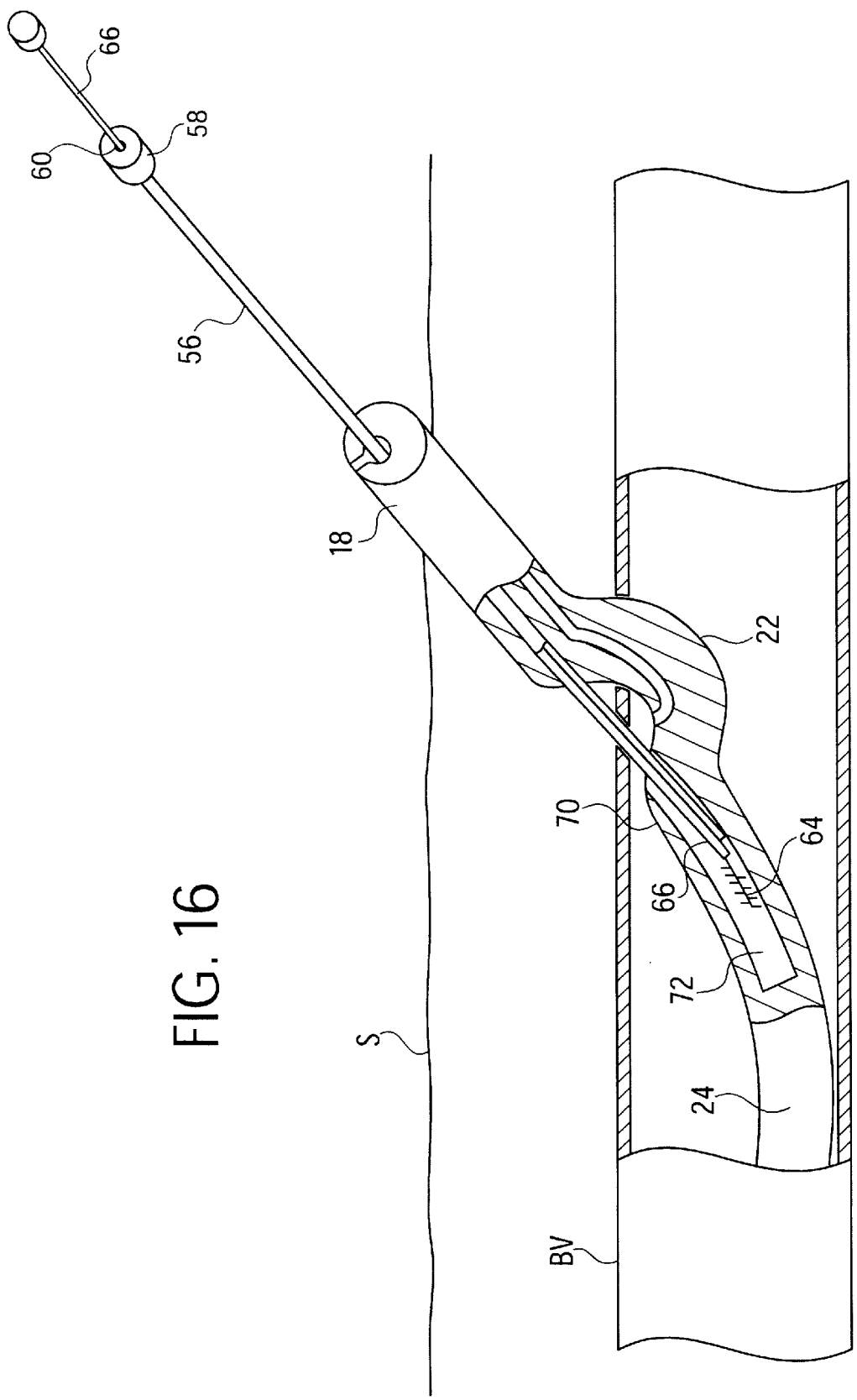
FIG. 16 shows a partially cross-sectional view of the blood vessel with a device according to the second embodiment of the present invention in the first desired position where a suture has been passed through the wall of the blood vessel and introduced into a suture retention chamber.

As shown in FIGS. 8–10, the doctor withdraws the device 1 from the body and detaches the suture 41 from the ends of the needles 37 and ties the two ends together in a slip knot which is urged inward toward the blood vessel and drawn tight in order to seal the puncture. Of course, those skilled in the art will appreciate that, once the two ends of the suture 41 have been drawn through the blood vessel wall, various other methods of fastening the two ends together may be employed.

FIGS. 11–19 show a suturing device according to a second embodiment of the present invention. The flexible tube 16 of the device 1' according to the second embodiment is preferably similar in size and flexibility to the device 1 of the first embodiment and differs only as described below. In addition, those skilled in the art will recognize that, except where specifically stated, each of the variations described above in reference to the first embodiment may also be applied to all other embodiments.

As seen in FIG. 12, the cross-section of the proximal part 18 of the device 1' shows a flash back lumen 30 of circular cross-section. The flash back lumen 30 of this embodiment extends from the first end 20, through the proximal part 18 to an opening 49 formed adjacent to the opening 68.

In addition, instead of the needle withdrawal lumen 26 of the first embodiment, the proximal part 18 of the device 1' includes a substantially circular puncture needle channel 50 extending from the first end 20 of the device 1' to an opening 52 at a proximal end of the central arcuate portion 22. This puncture needle channel 50 is also shown including an optional slot 54 extending through the surface of the flexible tube 16 along the length of the puncture needle channel 50.

A puncture needle 56, having an increased diameter gripping surface 58 at a proximal end, is slidably received in the puncture needle channel 50. The puncture needle 56 includes a central channel 59 extending from an opening 60 formed in the gripping surface 58 to an opening 61 formed in a distal end 62 of the puncture needle 50. One suture 41, integrally formed with or coupled to a respective anchor member 64, is received within the central channel 59. The anchor member 64 may be constructed as a coiled stainless steel spring.

Those skilled in the art will recognize that, if the puncture needle 56 is provided with a slot extending from a proximal end to a distal end thereof, a suture loop 41' may be formed with a single suture 41 having anchor members 64 at both ends. That is, after a first end of the suture has been inserted into the suture retention chamber 72, a first length of this suture 41 may be drawn out through the slot and a second anchor member 64 attached to a second end of the suture 41 may be inserted into the suture retention chamber 72 through a second portion of the blood vessel wall as described above. Thereafter, the device 1' is withdrawn from the body and the two ends of the suture loop 41' are tied together and, using known techniques, the knot is maneuvered so that it ends up on the outside of the blood vessel.

A plunger 66 is slidably received within the central channel 59 so that the anchor member 64 is located between the opening 61 and a distal end of the plunger 66 so that, when the plunger 66 is urged distally into the central channel 59, the anchor member 64 is moved toward the opening 61.

An opening 68 opposite the opening 52 at a distal end of the central arcuate portion 22, extends through a needle reception slot 70 to a suture retention chamber 72 which has an increased diameter relative to the needle reception slot 70. Those skilled in the art will recognize that many variations may be made to the structure of the anchor member 64 so long as sufficient stiffness is maintained and the anchor member is dimensioned so as to prevent the suture 41 from being withdrawn from the suture retention chamber 72 during withdrawal of the device 1' from the body.

In operation as shown in FIGS. 15–19, the device 1' is positioned with the central arcuate portion 22 straddling the blood vessel wall with the openings 52 and 68 on opposite sides of the wall (proximal and distal, respectively) and rotated to a desired position as described above in regard to the device 1 of the first embodiment.

As described above in regard to the device 1, the flash back lumen 30 may be used to determine whether or not the device 1' is in the desired position. Specifically, when the device 1' is in the desired position, blood should be observed only in the flash back lumen 30, not in the needle channel 50. Blood in the needle channel 50 indicates that the device 1' has been advanced too far into the blood vessel. That is, blood in the needle channel 50 indicates that the opening 52 is improperly positioned within the blood vessel. When the device 1' is properly positioned, the doctor presses upon the gripping surface 58 to urge the a sharp, distal end of the puncture needle 56 distally out of the opening 52, through the wall of the blood vessel and into the opening 56.

When the puncture needle 56 has been inserted into the suture retention chamber 72, the doctor pushes the plunger 66 distally within the central channel 59 to release the anchor member 64 into the suture retention chamber 72. The puncture needle 56 is then withdrawn from the suture retention chamber 72 and the plunger 66 is completely withdrawn from the central channel 59.

Where the device 1' includes the optional slot 54, the suture 41 may then be withdrawn from the puncture needle channel 50 through the slot 54. This allows the diameter of the puncture needle channel 50 to be minimized while providing sufficient room for the puncture needle 56 to pass therethrough. Then a second anchor member 64 and a second suture 41 are inserted into the central channel 59.

Figure 17:
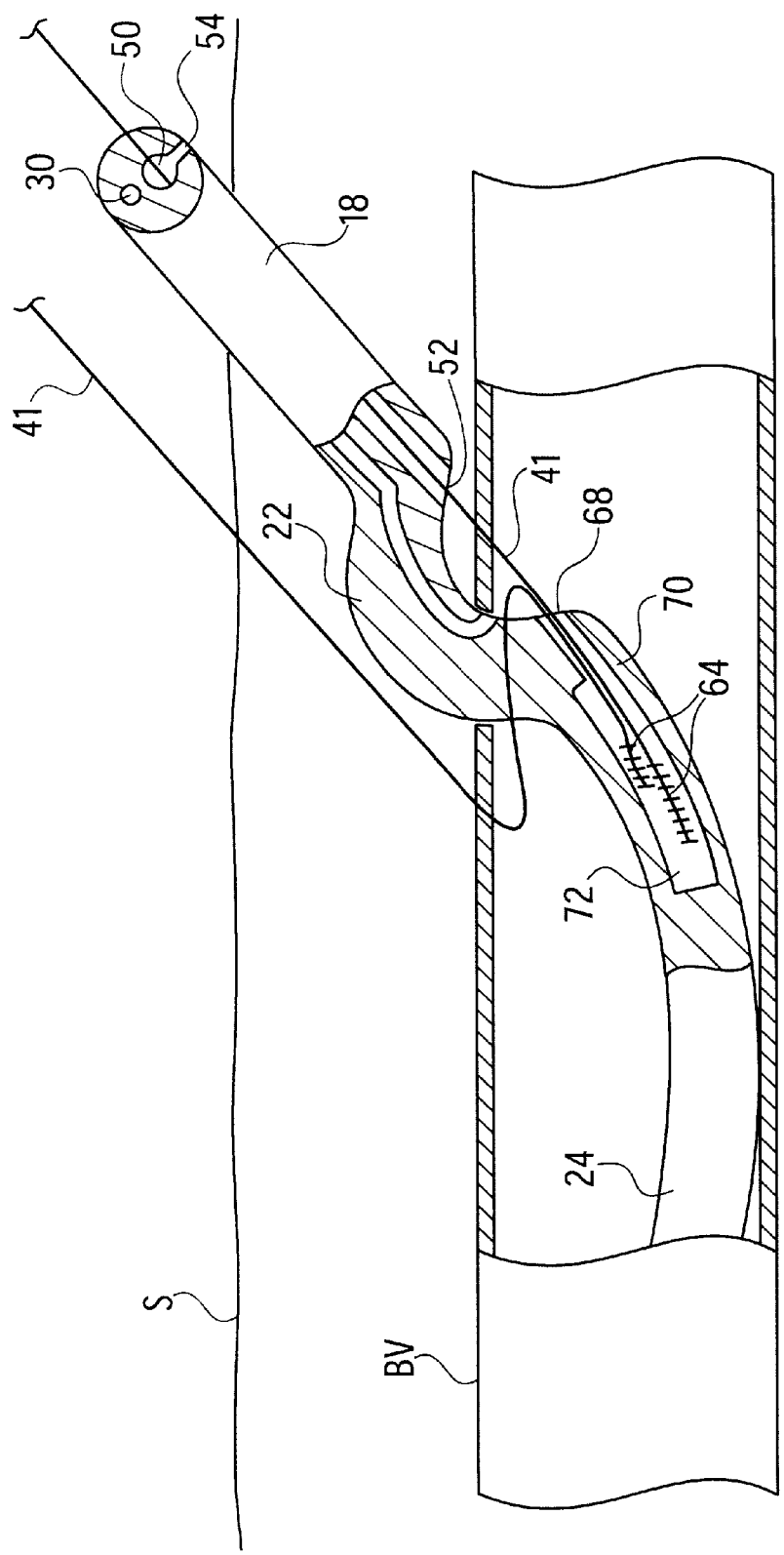
FIG. 17 shows a partially cross-sectional view of the blood vessel with a device according to the second embodiment of the present invention in a second desired position.
Figure 18:
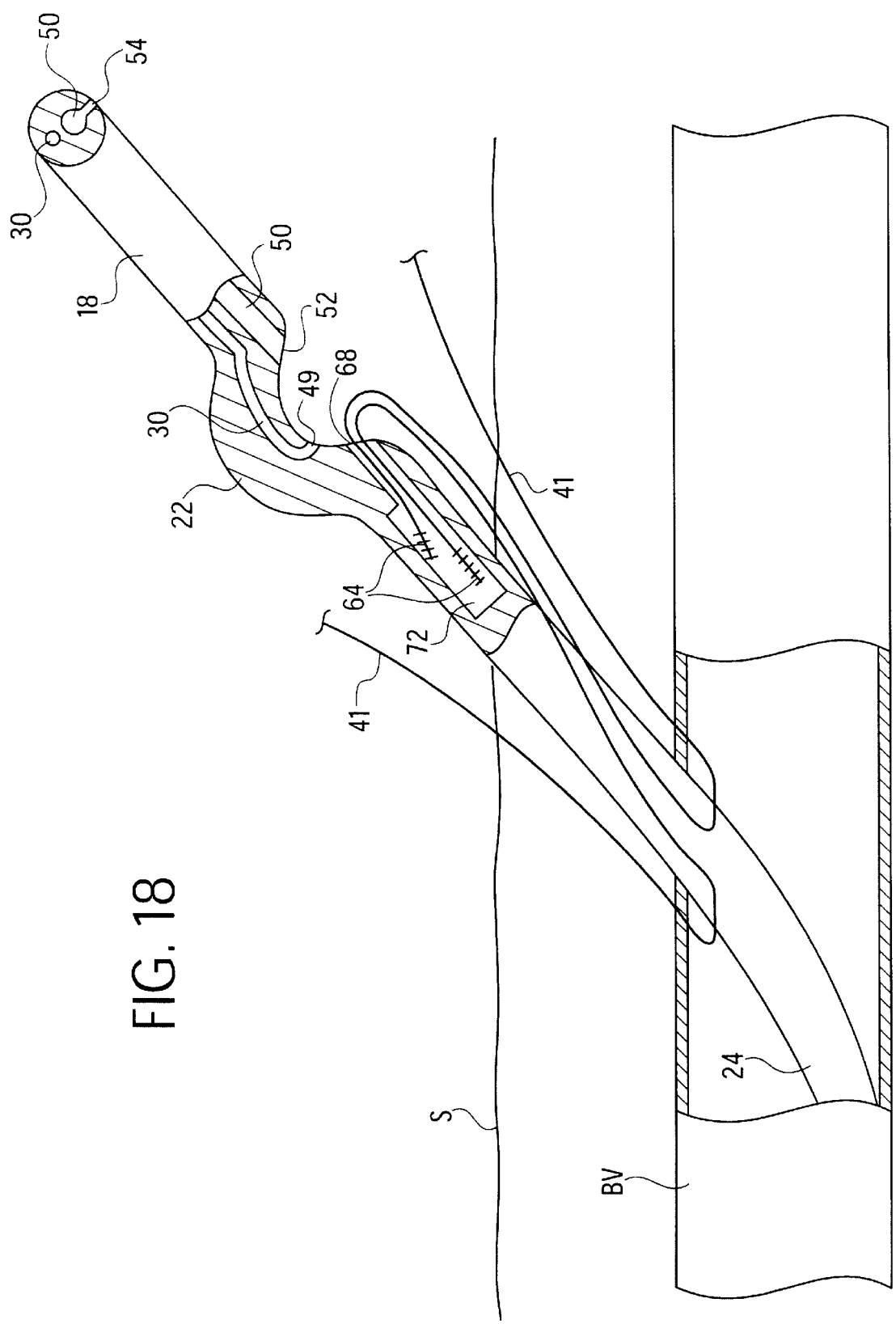
FIG. 18 shows a partially cross-sectional view of the blood vessel wherein the device according to the second embodiment has been partially withdrawn from the blood vessel.
Figure 19:
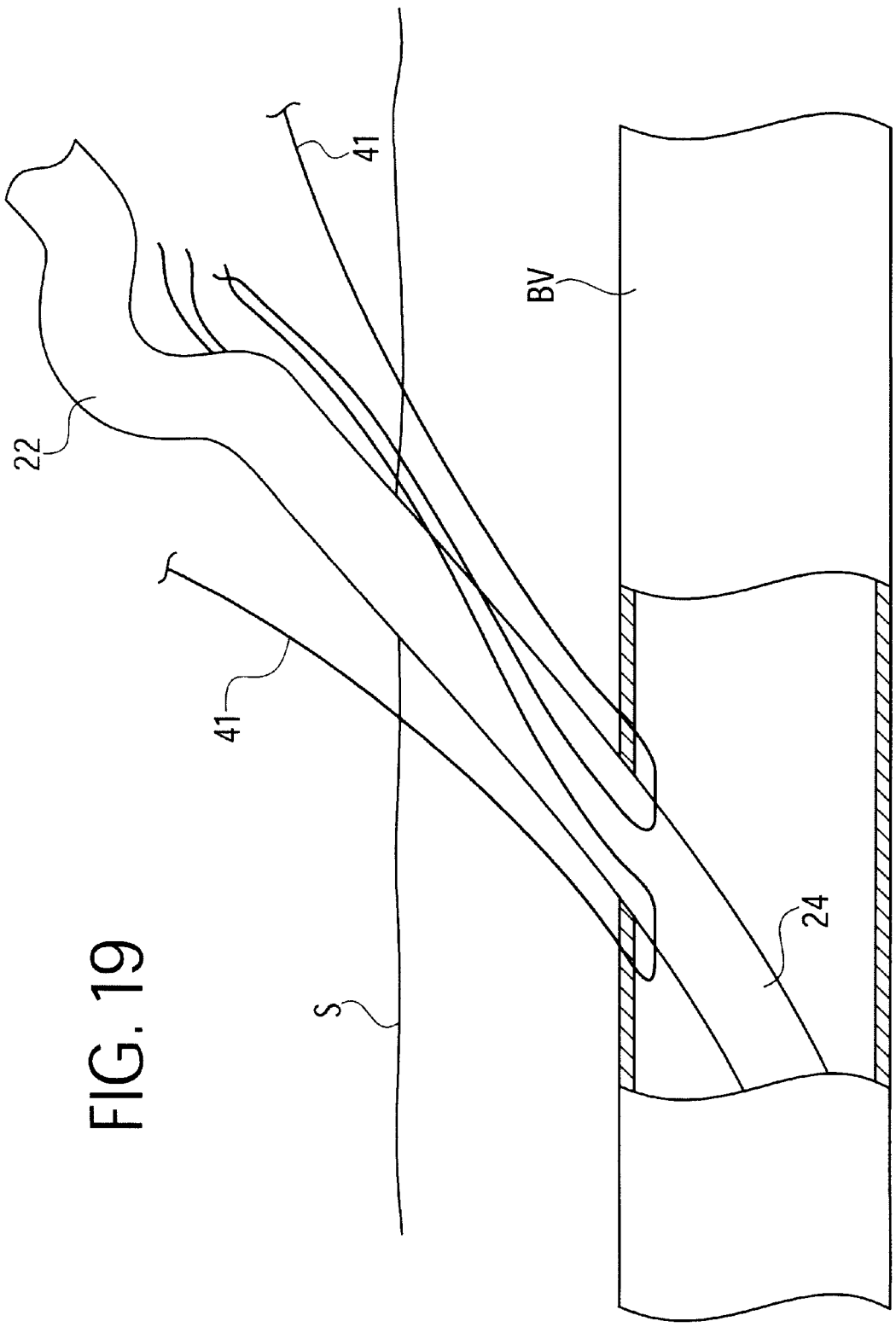
FIG. 19 shows a partially cross-sectional view of the blood vessel wherein the sutures have been severed from the anchor members and tied together.
Figure 20:
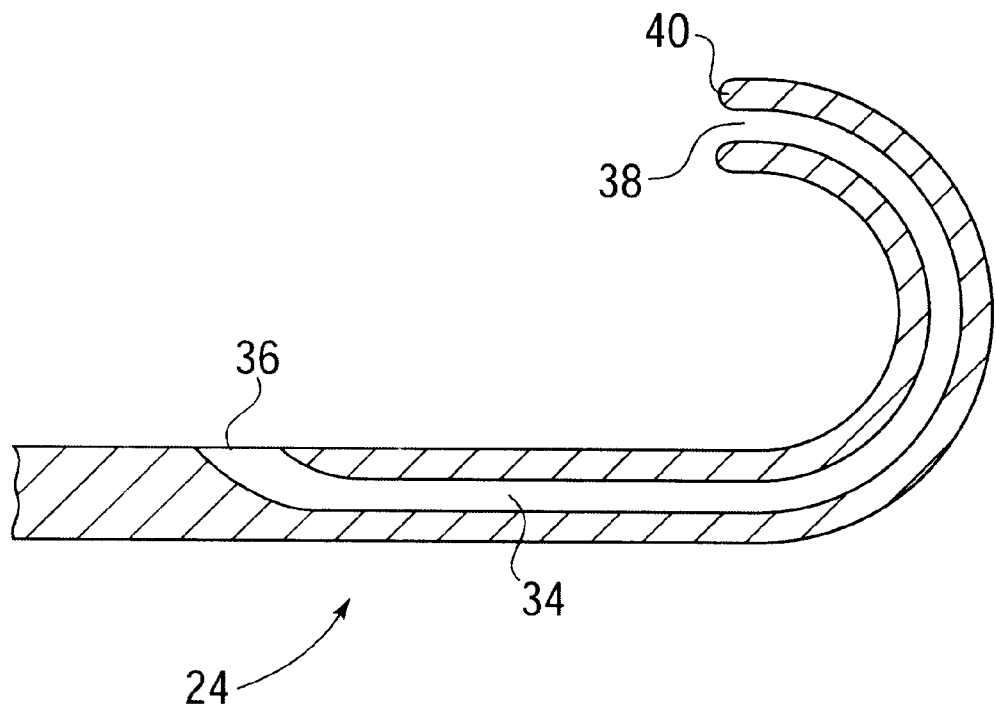
FIG. 20 shows a side view of a cross-section of a distal portion of a suturing device according to a third embodiment of the present invention.

As shown in FIG. 17, the doctor then reorients the device 1' into the second desired position, as described above in regard to the first embodiment, the doctor presses upon gripping the surface 58 to urge the sharp, distal end of the puncture needle 56 distally out of the opening 52, through the wall of the blood vessel and into the opening 56 so that the opening 61 is within the suture retention chamber 72. Thereafter, the doctor inserts the plunger 66 into the central channel 59 and pushes it forward to release the anchor member 64 and the second suture 41 into the suture retention chamber 72. Those skilled in the art will understand that, instead of inserting a second suture 41 at this point, a gripping device may be introduced through the central channel 59 into the suture retention chamber 72 to grab and retrieve the anchor member 64 and draw it out through the central channel 59. This allows for the formation of a suture loop 41' without the need to knot two separate strands of suture 41 together.

Figure 24:
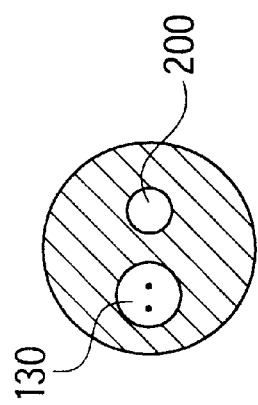
FIG. 24 shows a cross-sectional view of the suture device of FIG. 23 taken along the line 24—24.

The doctor then withdraws the device 1' from the body, as shown in FIG. 22, so that the ends of the sutures 41 extending from the opening 68 may be cut to release the sutures from the anchor members 64. Then, as shown in FIGS. 23 and 24, these ends of the sutures 41 are tied together and the other ends are knotted together and tightened to seal the puncture.

Those skilled in the art will understand that, for larger punctures, the device 1" may be used to insert as many sutures 41 as are required to seal the puncture. Specifically, in order to close punctures larger than size 9.0 French, a single suture 41 may not be sufficient. Therefore, instead of using the device 1" as described above to insert two sutures 41 approximately 180° apart, a doctor may, for example, insert four sutures 41 at 90° intervals using the technique described above. Then, when the device 1" has been withdrawn from the body, the doctor must knot together a first pair of sutures 41 which are separated by approximately 180° and then knot the second pair. The two pairs of sutures 41 may be distinguished by color coding or any similar technique.

A device 1" according to a third embodiment of the present invention is shown in FIGS. 25 and 26. Aside from a modified distal part 24 as described below, the construction and operation of the device 1" may be identical to either of the first and second embodiments.

Specifically, the distal part 24 of the device 1" is constructed so that it has enhanced flexibility relative to the proximal part 18. In addition, the distal part 24 is biased so that, when in an unstressed state, it is "J" shaped—that is, the distal part 24 is curved so that the distal opening 38 formed in the second end 40 faces proximally. This facilitates insertion of the device 1" so that it contacts an inner wall of the blood vessel without damaging it. Specifically, the flexibility and "J" shape of the second end 40 allows the second end 40 to deflect away from the blood vessel's lining without penetrating or damaging the lining thereof. Of course, when received on the guide wire 44, the "J" shape of the distal part 24 will be less pronounced. However, the bias will maintain a slight curvature of the second end 40 deflecting the impact of the device 1" from the inside lining of the blood vessel.

Figure 21:
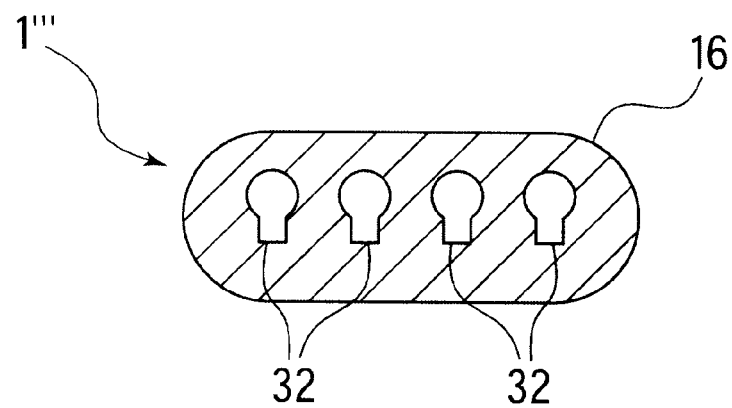
FIG. 21 shows a cross-section of a distal portion of a device according to the fourth embodiment of the invention.

As described above, in order to close punctures larger than size 9.0 French, a single suture 41 may not be sufficient. Thus, as shown in FIG. 21, a device 1''' according to a fourth embodiment of the invention may receive four needles 37 arranged side-by-side in four needle retention bores 32 formed in a flexible tube 16 of substantially oval cross-section. Other than the oval cross-section and the provision of four needles, the construction and operation of the device 1''' is similar to that of the device 1 according to the first embodiment.

The oval cross section increases the stiffness of the device 1''' in the plane in which the four needles lie side-by-side, while retaining flexibility to bend perpendicularly to that plane. The four needles 37 of the device 1''' are coupled together in pairs and each pair of needles will be positioned so that the needles 37 of each pair penetrate the wall of the blood vessel on opposite sides of the puncture (approximately 180° apart). When the device 1''' has been removed from the body, each pair is then knotted together and the two knots are tightened to seal the puncture.

Of course, those skilled in the art will understand that each of the variations of the device 1 according to the first embodiment may also be applied to the device 1'''. Similarly, those skilled in the art will recognize that four needles 37 may be received in a device 1 having two needle retention bores 32, each being of a length sufficient to hold two needles 37 arranged in series end-to-end.

FIG. 22 shows a further embodiment of a suture device 101 according to the present invention. In this embodiment, the needles 137 are deployed simultaneously, eliminating the need to rotate the device 101 within the opening in the anatomical structure. This is achieved with a device 101 formed as an elongated member 116 having a rigid proximal portion 118 and a flexible distal portion 124 connected by a central portion 122. The proximal portion 118 and the distal portion 124 are both, for example, substantially circular in cross section. A distal end 121 of the proximal portion 118 has, for example, a slightly larger diameter than the rest of the proximal portion 118, forming a stop 221. The central portion 122 is, for example, oval or oblong in cross section. Moreover, unlike the central arcuate portion 22 of the other embodiments of the device (1, 1", etc.) of the present invention, the central portion 122 may be substantially straight.

As can be seen from FIG. 23, the proximal portion 116 has, for example, a pair of axially-running lumens extending therethrough: a position indication lumen 200 and a suture lumen 130. The position indication lumen 200 extends from a proximal position opening 201 in a proximal end 120 of the proximal portion 118 to a central position opening 202 in the central portion 122. In the central portion 122, the position indication lumen 200 turns, for example, 90° outward, so that the position indication lumen 200 runs radially outward until it terminates at the central position opening 202.

The suture lumen 130 extends from a proximal suture opening 131 in the proximal end 120 of the proximal portion 118 to a needle chamber 132 disposed in the distal portion 124. The suture lumen 130 is also connected to a central suture opening 203 in the central portion 122. The central suture opening 203 extends radially outward from the suture lumen 130. However, the central suture opening 203 runs, for example, in an opposite direction from the position indication lumen 200, so that the central suture opening 203 and the central position opening 202 are on radially opposite sides of the central portion 122.

As shown in FIG. 24, the suture lumen 130 is, for example, substantially oval or oblong in cross section while the position indication lumen 200 is, for example, substantially circular in cross section.

Further details of the elongated member 116 are shown in FIG. 25. The distal portion 124 includes, for example, a single, axially-running needle chamber 132 holding, for example, a pair of needles 137. The needles 137 are not fully contained in the needle chamber 132. Instead, part of each needle 137 extends through a needle channel 123.

Each needle channel 123 runs substantially axially from the needle chamber 132 to a needle channel opening 133. However, as can be seen from FIG. 25, each needle channel 123 also runs, for example, slightly radially outwardly as it extends from the needle chamber 132 to the respective needle channel opening 133. The needle channel openings 133 appear on a proximal face 233 of the distal portion 124, and are located, for example, on radially opposite sides of the proximal face 233 of the distal portion 124. Thus as the needles 137 exit the needle channels 123, the needles 137 move substantially in the proximal direction (towards the right as seen in FIG. 25), but also slightly outwardly in opposite radial directions from one another.

In addition to being radially opposite from each other, the needle channel openings 133 are each, for example, radially offset 900 from the central position opening 202 and the central suture opening 203. The needle channel openings 133 are, for example, radially aligned with the minor axis of the oval central portion 122, while the central position opening 202 and the central suture opening 203 are located, for example, on the major axis of the central portion 122.

For example, two segments of a length of suture 141 are contained within the elongated member 116. The length of suture 141 is doubled over itself so that a suture loop 142 extends outside the proximal suture opening 131. Two segments of the length of suture 141 enter the suture lumen 130 via the suture opening 131 and exit the suture lumen 130 via the central suture opening 203. Each of the two segments then enters a respective needle channel 123 and travels ultimately to the needle chamber 132. The end of each segment of the length of suture 141 is connected to the distal end of a respective one of the needles 137 within the needle chamber 132.

As can also be seen from FIG. 25, the device 101 according to this embodiment may be manufactured in three sections: a first section including the proximal portion 118, the central portion 122, and the proximal end of the distal portion 124 containing the needle channels 123; a second section including only that part of the distal portion 124 containing the needle chamber 132; and a third section including only a soft tip 140 at the distal end of the distal portion 124. These various sections may preferably be formed separately, for example by extrusion or molding, and then fixed together.

FIGS. 26, 27 and 28 show cross-sectional views of the device 101 taken along lines 26—26, 27—27, and 28—28 of FIG. 25, respectively. FIG. 26 shows the distal portion 124 with the needle chamber 132 therein. The needle chamber 132 contains, for example, two needles 137, each needle 137 connected to an end of a length of suture 141. FIG. 27 shows the central portion 122 and the proximal face 233 of the distal portion 124. The suture 141 passes from the suture lumen 130 and central suture opening 202 into the needle channel openings 133. FIG. 28 shows the proximal portion 118 with the position indication lumen 201 and the suture lumen 130 therein. The suture lumen 130 contains two segments of a length of suture 141.

Figure 30:
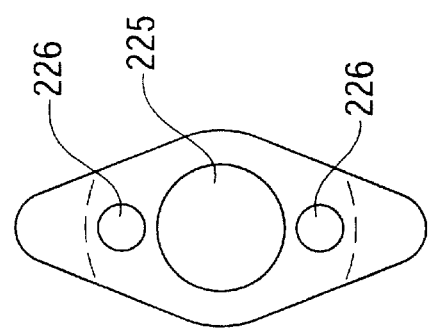
FIG. 30 shows a cross-sectional view of the needle receiving body of FIG. 29 taken along line 30—30.
Figure 29:
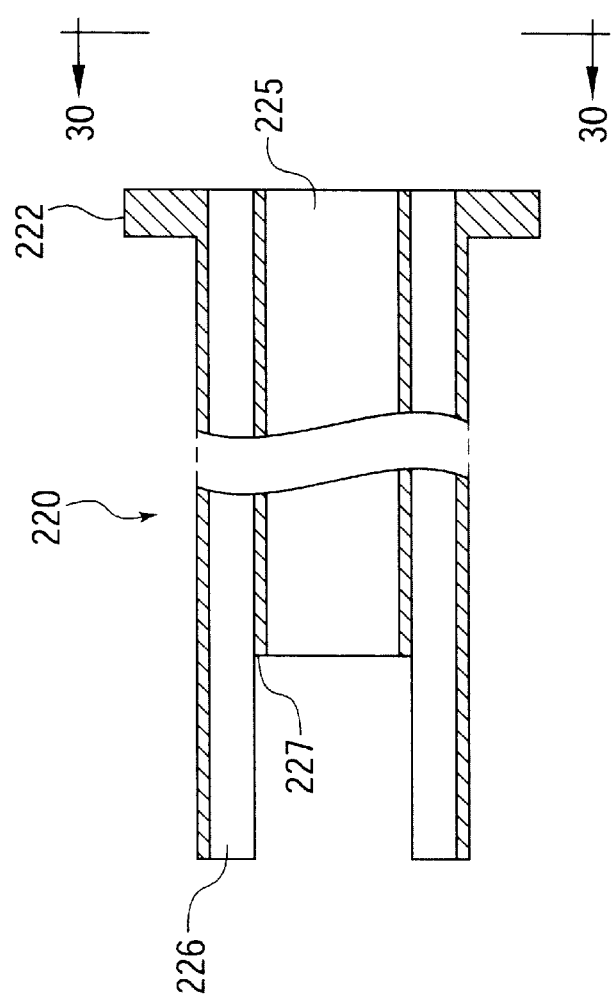
FIG. 29 shows a side view of a needle receiving body according to the present invention.

A needle receiving body 220 of the device 101 is shown, for example, in FIGS. 29 and 30. The needle receiving body 220 as shown is an elongated member having a generally annular cross section for most of its length. Two protrusions 222 extend, for example, radially outward from a proximal end 221 of the needle receiving body 220. The protrusions 222 assist in handling the needle receiving body 220.

The needle receiving body 220 has a device lumen 225 extending axially therethrough. The device lumen 225 shares, for example, the same axis as the needle receiving body 220 as a whole (i.e. the device lumen 225 is radially centered within the needle receiving body 220). The device lumen 225 has a first inner diameter substantially the same diameter as, or slightly larger than, the outer diameter of the proximal portion 118 and a second inner diameter slightly larger than the first inner diameter so that an abutment 227 is formed at the intersection of the portion having the first inner diameter and the portion having the second inner diameter.

On opposite side of the device lumen 225 extend, for example, a pair of axially-running needle receiving channels 226.

The inner diameter of the needle receiving body 220 allows in to be slidably placed upon the elongated member 116. The needle receiving body 220 travels down the proximal portion 118, and slides distally until the abutment 227 of the needle receiving body 220 contacts the stop 221 on the elongated member 116. At this point the needle receiving body 220 may be fixedly or rotatably joined to the elongated member (for example, as part of the manufacturing process), or may remain slidably and/or frictionally coupled with the elongated member 116. The latter allows the use of a device 101 without a needle receiving body if so desired, for example when closing skin wounds or during certain laparoscopic procedures.

Figure 31:
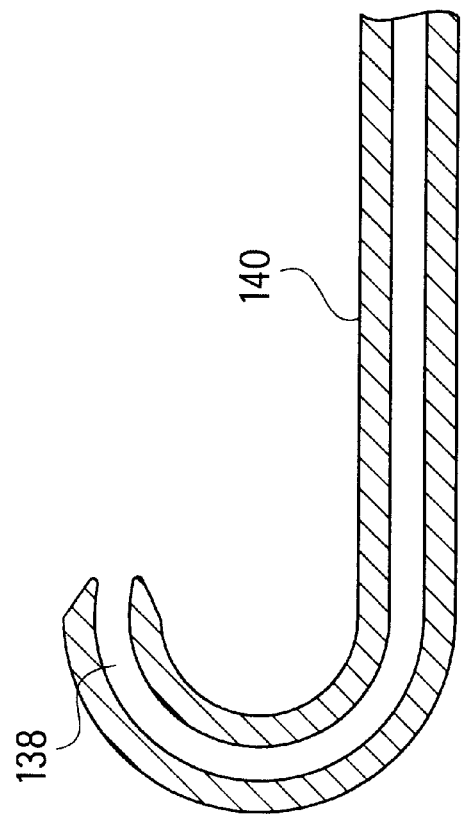
FIG. 31 shows a side view of a distal end of another embodiment of the suture device according to the present invention.

FIG. 31 shows the tip 140 which is disposed at the distal end of distal portion 124. As seen from the Figure, the tip 140 may be a J-shaped, elongated member. The tip 140 may also, however, be formed as a straight member or any other shape, as dictated by the shape of the anatomical structure and surrounding tissues. The tip 140 includes, for example, an axially-running guide wire lumen 138 extending therethrough. The tip 140 may be formed of, for example, a soft or flexible material. The shape of the tip 140 and its material allow the tip 140 to be easily inserted into the anatomical structure.

Figures 32, 33:
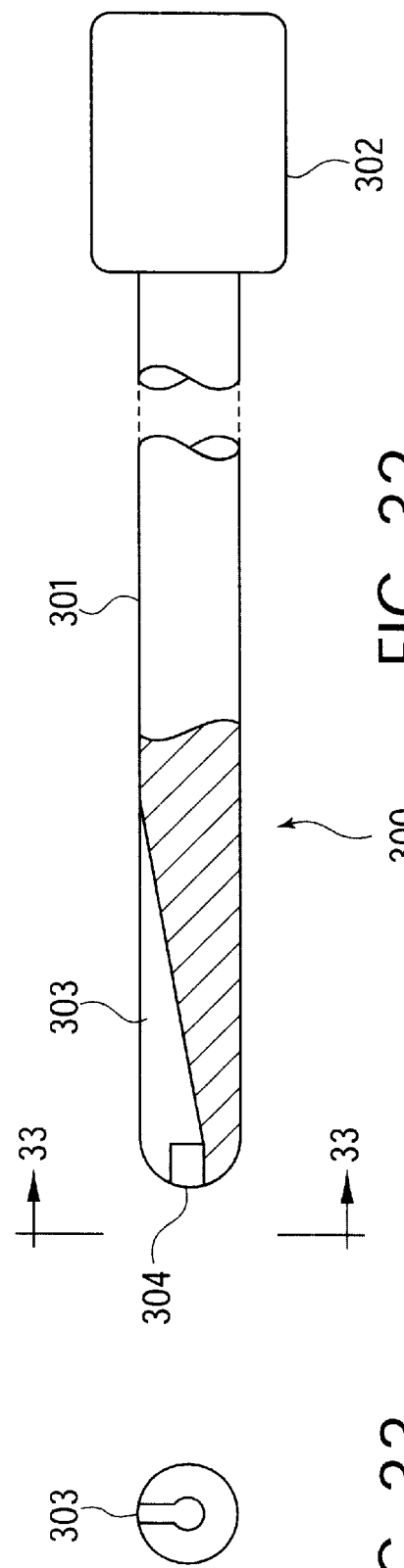
FIG. 32 shows a side view of a knot pusher according to the present invention.
FIG. 33 shows a cross-sectional view of the knot pusher of FIG. 32 taken along line 33—33.
Figure 38:
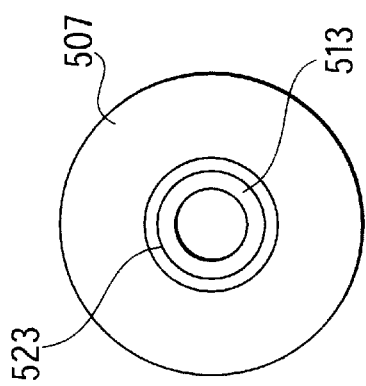
FIG. 38 shows a back view of the barrel of FIG. 37 taken along line 38—38 of FIG. 37.

The device 101 according to this embodiment of the present invention may also include a knot pusher 300, as shown in FIGS. 32 and 33. The knot pusher 300 includes a longitudinal member 301 having, for example, a circular cross section. A knob 302 is disposed at a proximal end of the longitudinal member 301. The distal end of the longitudinal member 301 is, for example, rounded.

The distal end of the longitudinal member has an axially-extending slit 303 formed therein. The slit 303 has, for example, a constant width appropriately sized to accommodate two or more segments of a length of suture 141, but small enough so that a knot cannot enter the slit 303. The depth of the slit 303, however, decreases as the slit extends proximally from the distal end of the longitudinal member 301. The slit 303 has an initial depth, for example, slightly greater than the radius of the longitudinal member 301, and the depth decreases to zero, for example linearly, as the slit extends proximally.

The distal end of the longitudinal member 301 also has, for example, a circular recess 304 formed therein. The recess 304 intersects the slit 303, forming a continuous path through the elongated member 301. The recess 304 preferably has a radius greater than the width of the slit 303, and should generally be sized to accommodate a knot in the length of suture 141. Thus a knot in a length of suture 141 may be inserted into the recess 304 and the ends of the length of suture 141 pulled through the slit 303 to tighten the knot.

FIGS. 34 to 44 illustrate a second exemplary device and method for stabilizing the suture 141. These Figures show a suture crimping device 500, which clamps the free ends of suture 141 with a grommet 517. Generally, crimping device 500 includes a barrel 501 and a piston 503. Barrel 501 includes a shaft 505, preferably cylindrical in shape, and may also include a barrel hub 507 if desired. Similarly, piston 503 includes a preferably cylindrical shaft 509 and may include a piston hub 511. Piston 503 and barrel 501 are sized so that piston 503 may be inserted into barrel 501.

The distal ends of barrel 501 and piston 503 are constructed so that the distal end of piston 503 is compressed as it is inserted into barrel 501. In particular, barrel 501 includes an inner camming surface 513, and piston 503 includes an outer camming surface 515. The distal end of piston 503 is also constructed to receive a grommet 517. Grommet 517 is crimped as piston 503 is compressed, thereby clamping a suture 141 which may be threaded through the grommet 517.

The distal end of piston 503 preferably includes a pair of arms 519, which are flexible and easily compressible as piston 503 is advanced into barrel 501. To increase flexibility further, piston 503 may also include a relief hole 521 formed at the base of arms 519. To hold grommet 517, arms 519 are preferably provided with a recess 516, best illustrated in FIG. 39, although any retention mechanism may be utilized for this purpose. In addition, as illustrated in FIGS. 39 and 40, arms 519 are preferably laterally compressed near ends 520 to allow full advancement of piston 503 into barrel 501.

Grommet 517 is preferably circular, for example toroid, in shape, and may be formed of any suitable materials, for example metal, plastic, or biological material. Grommet 517 is preferably at least partially reabsorbable, but permanent materials may be used if desired. In a particularly advantageous construction, grommet 517 includes a plurality of layers. For example, grommet 517 may include an inner layer of adhesive such as cyonacrylate or fibrin, surrounded by an outer layer of permanent or resorbable material. Alternatively, grommet 517 may include an inner layer of permanent or resorbable material surrounded by an outer layer of, for example, collagen or adhesive.

Figure 42:
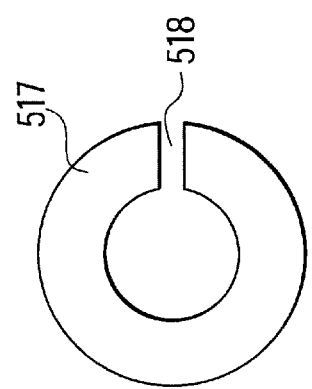
FIG. 42 shows an exemplary grommet according to the present invention.
Figure 37:
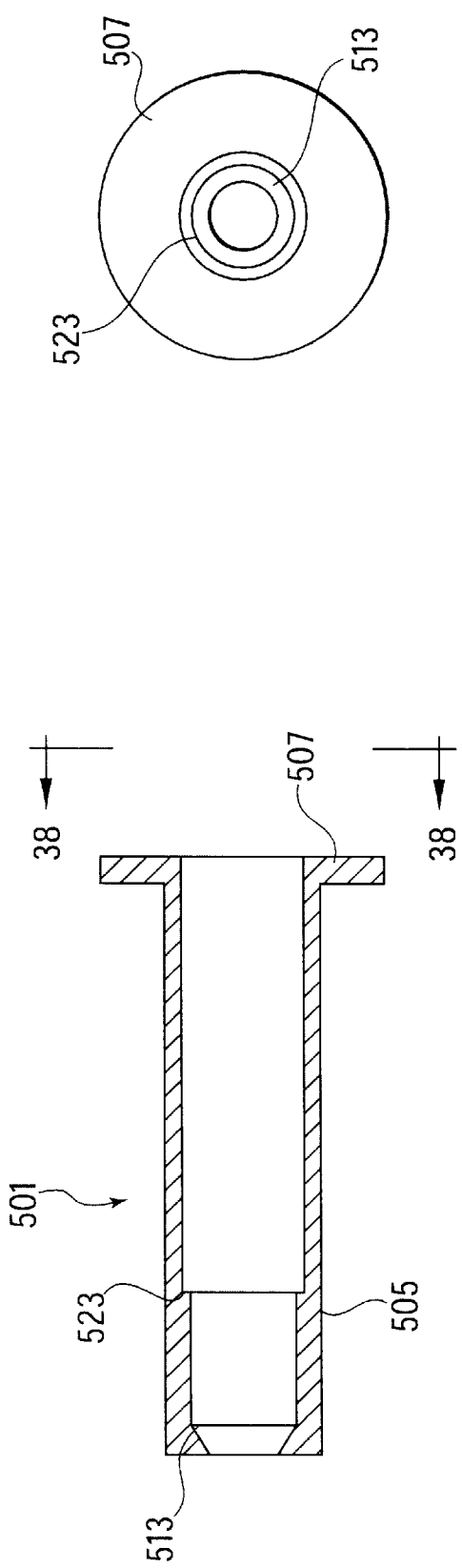
FIG. 37 shows a cross-sectional view of a barrel according to the present invention.
Figure 43:
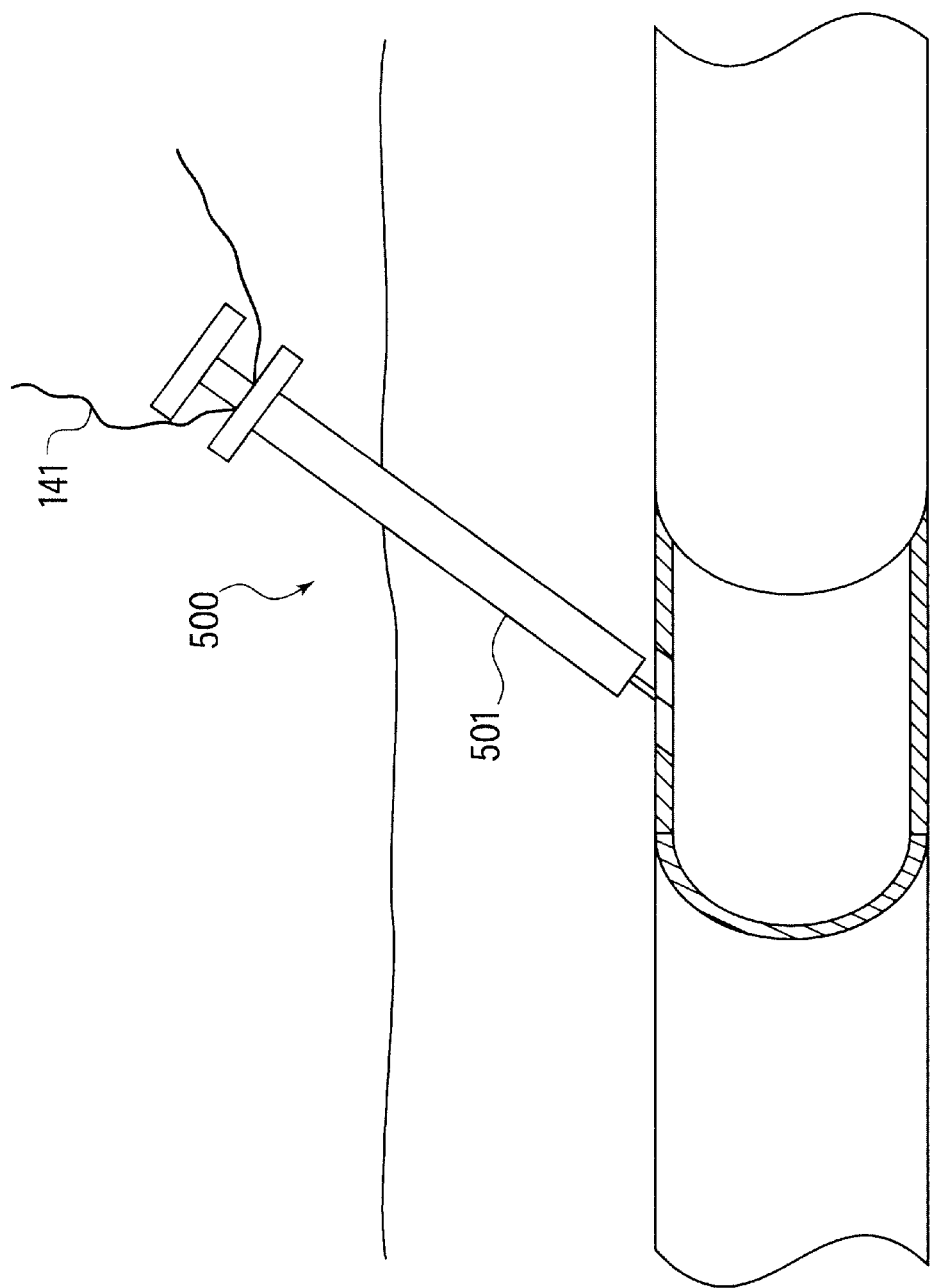
FIG. 43 shows a side view of the suture crimping device of FIG. 34 with a suture drawn therethrough.
Figure 44:
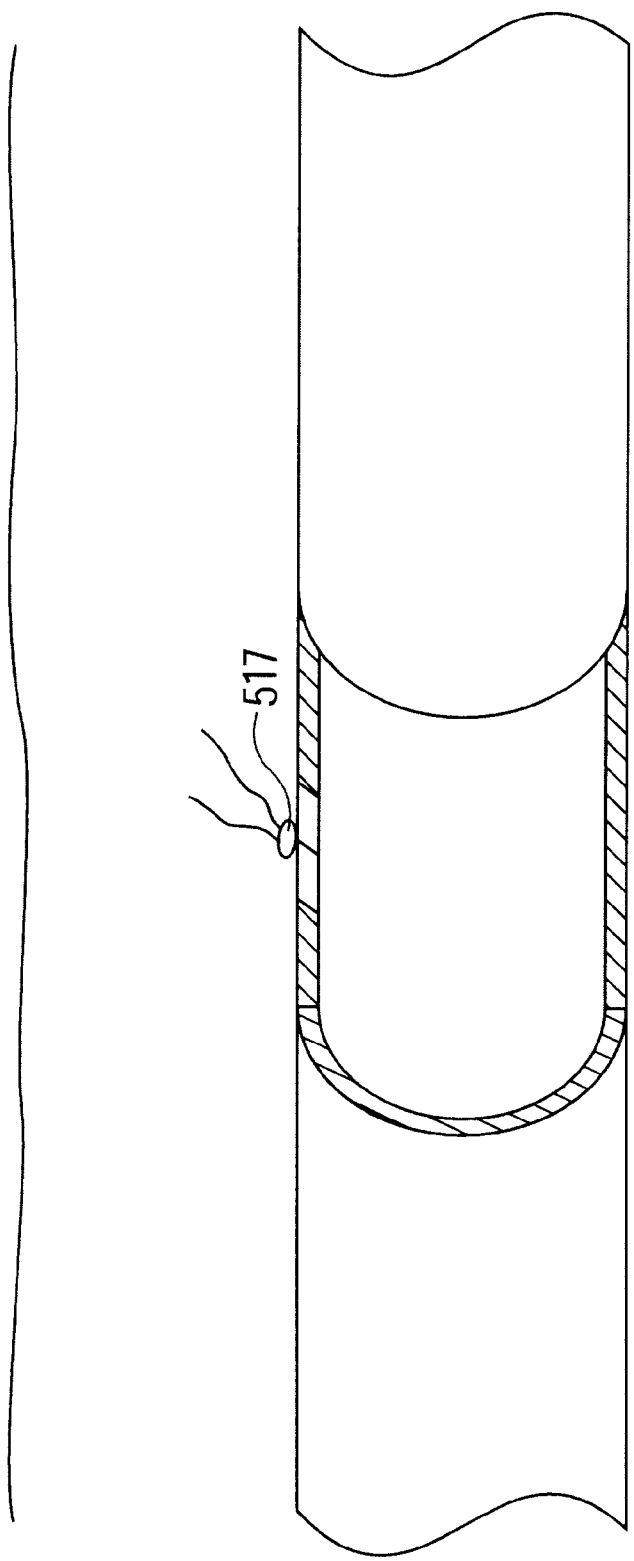
FIG. 44 shows an exemplary grommet according to the present invention clamping a suture.

As illustrated in FIGS. 43 and 44, a suture 141 may be threaded through barrel 501 so that the distal end of barrel 501 is oriented towards the blood vessel. Suture 141 may then be threaded through grommet 517. For this purpose, grommet 517 may include a transverse slit 518, as shown in FIG. 42. While tightening tension is applied to suture 141, piston 503 may be inserted into barrel 501 until camming surfaces 513 and 515 compress arms 519. This compression crimps grommet 517, clamping grommet 517 over suture 141. In this manner, suture 141 is quickly stabilized, sealing the puncture, without the need for tying a knot.

Barrel 501 preferably includes a stop 523. Stop 523 is formed at the abutment of two sections of barrel 501 having different interior diameters. Specifically, the distal end of barrel 501 may have a diameter slightly smaller than the diameter of a proximal section of barrel 501. The diameter of the distal end of the barrel 501 is preferably chosen to closely correspond to an outer diameter of the piston 503. Thus, as piston 503 is advanced into barrel 501, portions of the suture 141 received between the outer diameter of the piston 503 and the inner surface of the barrel 501 will be severed as relief hole 521 advances beyond stop 523. In this manner, the long ends of suture 141 are automatically removed from the crimped section of suture 141.

Figure 44A:
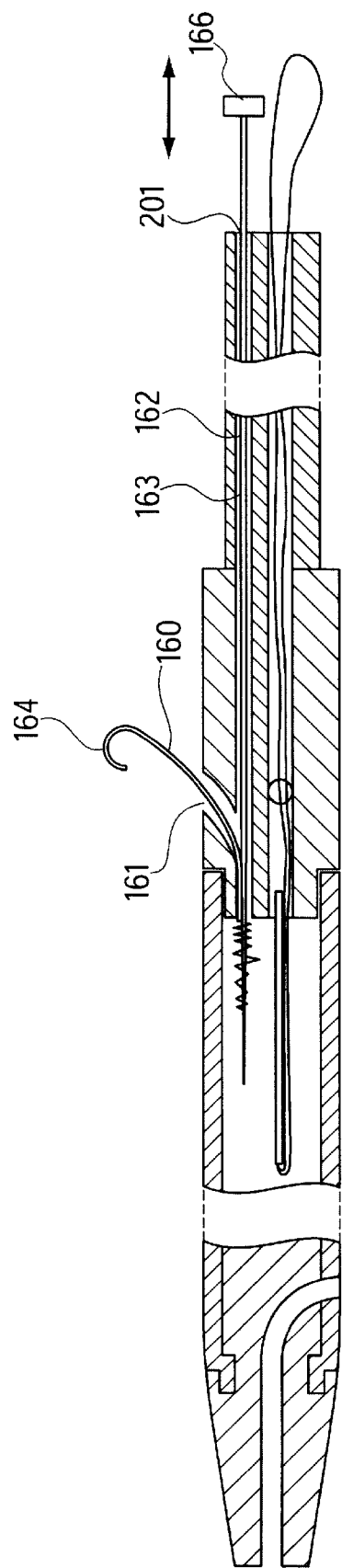
FIG. 44A shows an further exemplary embodiment of a suture device according to the present invention.
Figure 45:
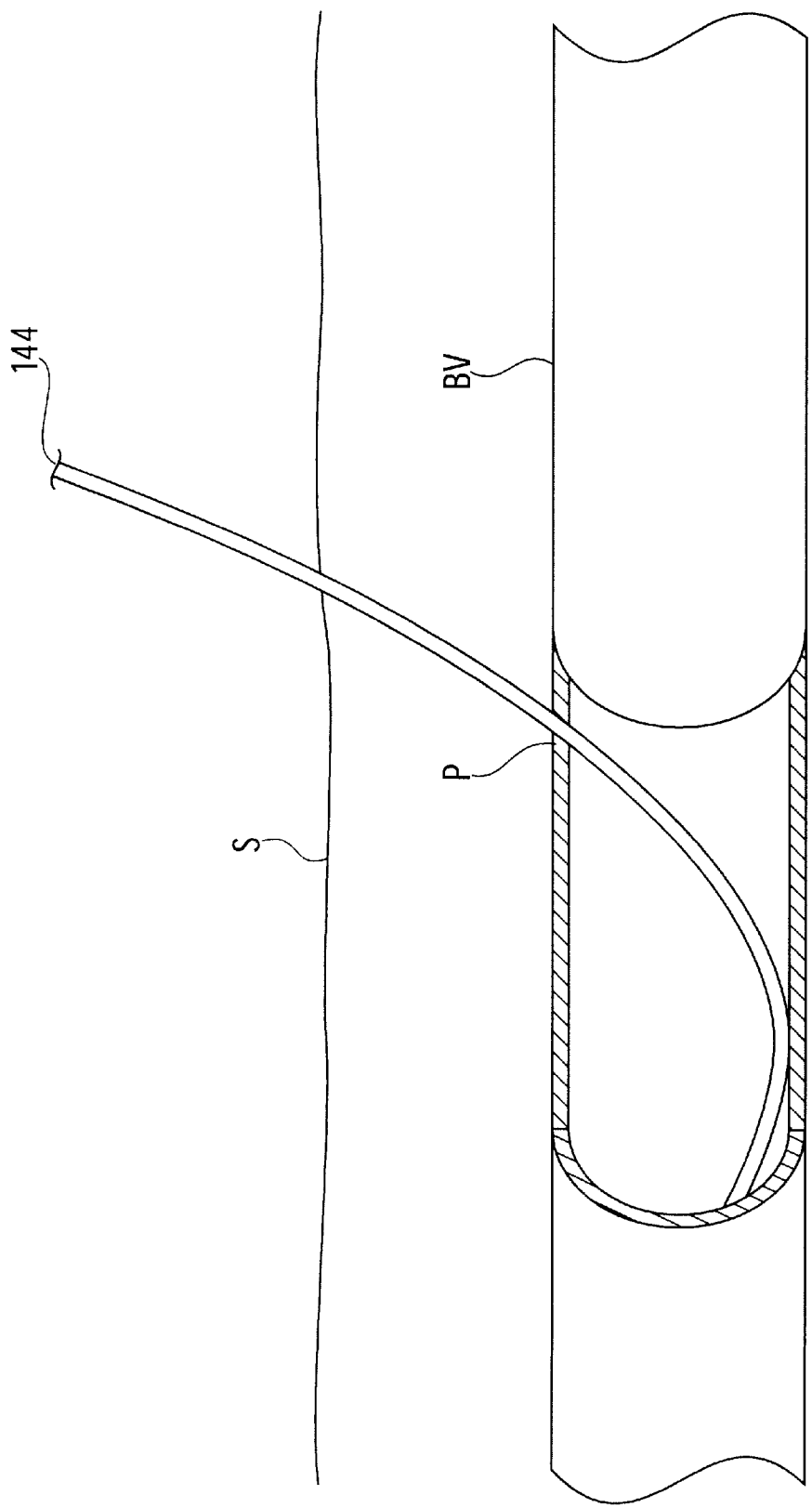
FIG. 45 shows a perspective view of a guide wire inserted into an anatomical structure, specifically a blood vessel.
Figure 46:
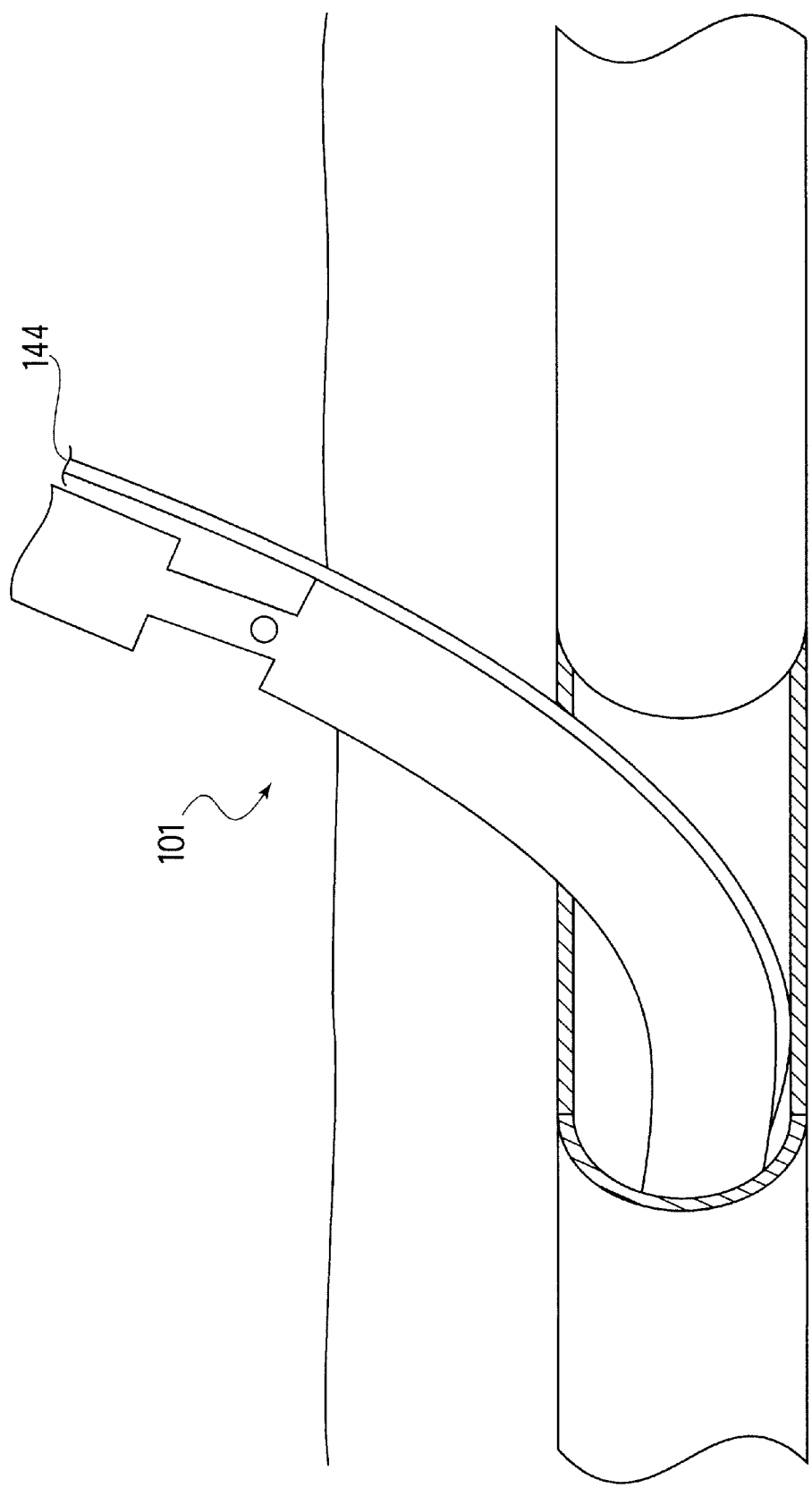
FIG. 46 shows a perspective view of a suture device according to the present invention partially inserted into an anatomical structure.
Figure 47:
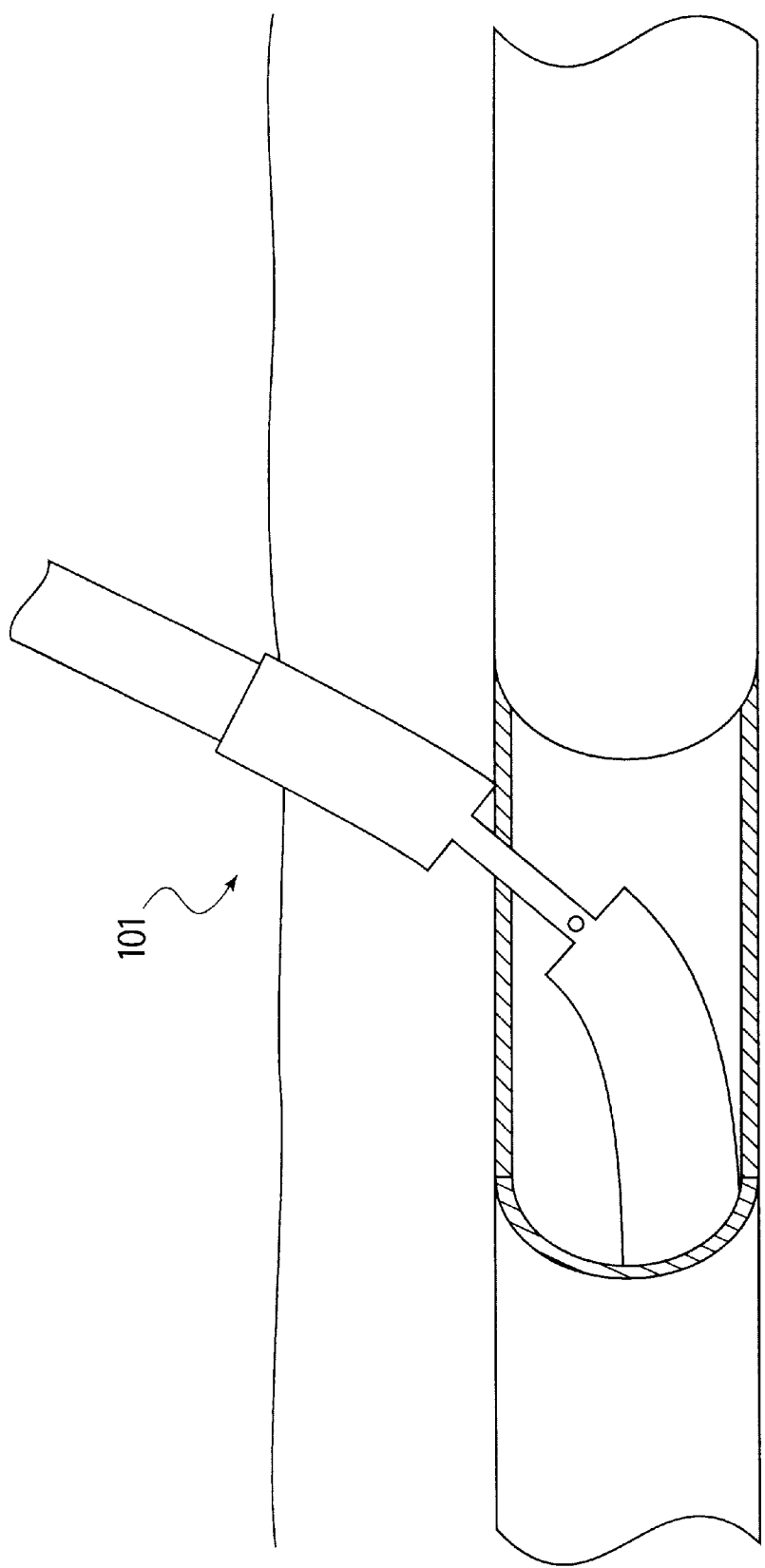
FIG. 47 shows a perspective view of the suture device of FIG. 46 inserted to a desired position in an anatomical structure.
Figure 48:
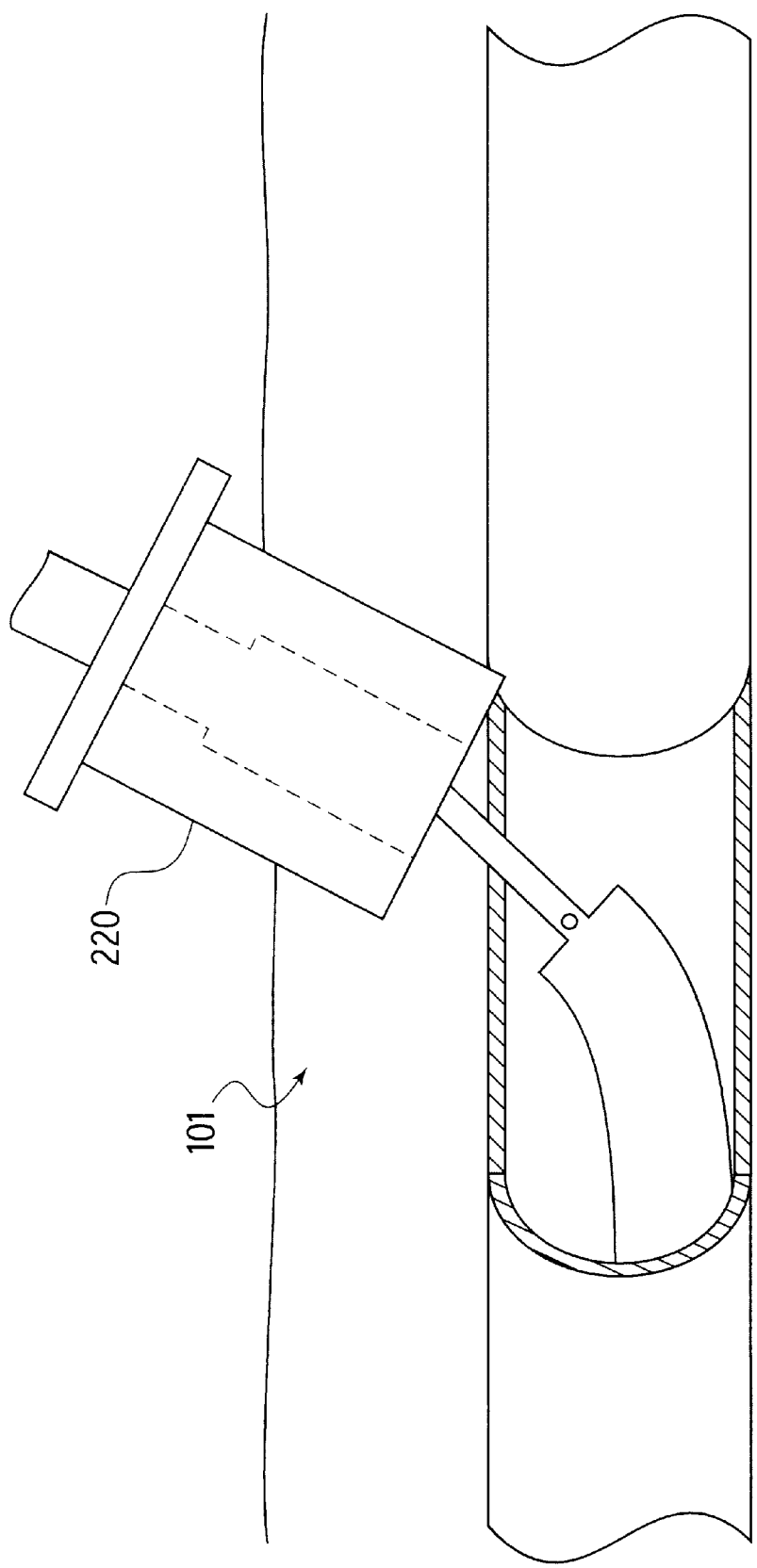
FIG. 48 shows a perspective view of the suture device of FIG. 26 with a needle receiving body according to the present invention.
Figure 49:
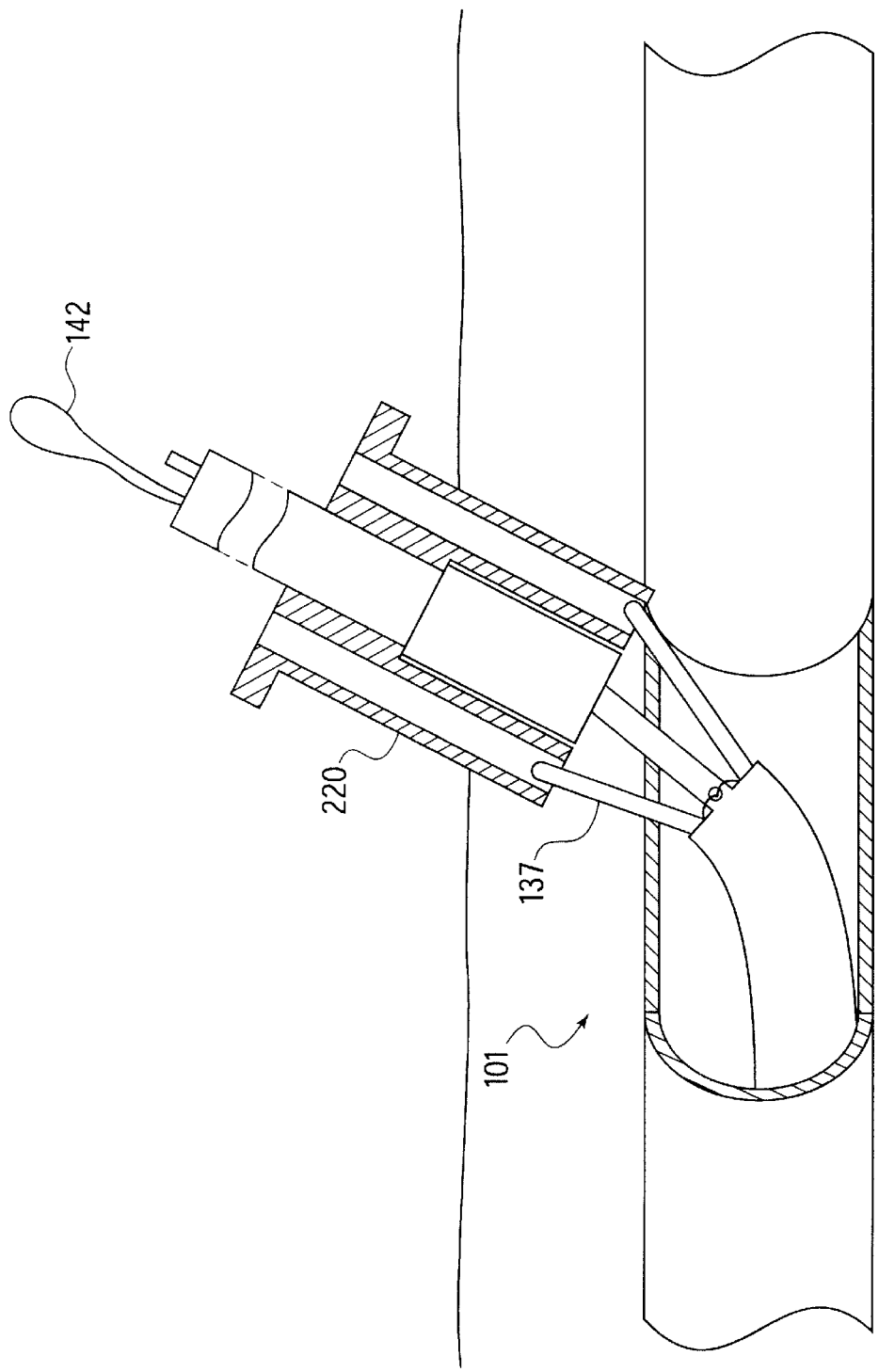
FIG. 49 shows a perspective view of the suture device of FIG. 48 with a pair of puncture needles partially deployed.

FIG. 44A illustrates a further exemplary embodiment of the present invention. In this embodiment, the control arm lumen 163 is shaped, for example, to house a retractable anchor 160 and an anchor control arm 162. In particular, the portion of the control arm lumen 163 extending radially outward may, for example, be slanted backward (i.e. proximally) toward the control arm opening 161.

Control arm 162 extends, for example, through the axial portion of control arm lumen 163, as shown in FIG. 44A, exiting the proximal position opening 201. Anchor 160 may be attached to the control arm 162 near a distal end of the control arm 162. Anchor 160 may be at least partially retained, for example, in the backward-slanting section of control arm lumen 163.

In an exemplary embodiment, anchor 160 is a flexible member. In an unbiased configuration, the end of the anchor 160 may form a curved anchor hook 164. This unbiased configuration may be obtained, for example, when the anchor hook 164 is outside the position indication lumen control arm lumen 163 as shown in FIG. 44A. When the anchor hook 164 is within the control arm lumen 163, the interior wall of the position indication lumen biases the anchor hook 164 to a substantially straight configuration.

It will be understood by one of skill in the art that the control arm 162, and the anchor 160 are capable of movement between retraced and extended positions. In the retracted position, the control arm 162 projects distally into the control arm lumen 163 so that anchor 160, including anchor hook 164, are retracted into the control arm lumen 163. Several features may be employed to limit the distal movement of the control arm 162, if desired. For example, a control arm stop 166 may be attached to the portion of control arm outside the suture device 101. The control arm stop 166 will contact the distal end of the suture device 101 when the control arm 160 reaches a distal-most position. Similarly, the distal end of control arm 162 may contact a distal end face of the control arm lumen 163, preventing further distal movement of the control arm 162. Alternatively, the diameter of the control arm 162 may increase moving away from the distal end, so that the wider-diameter section of the control arm 162 is prevented from entering a distal portion of the control arm lumen 163 having a smaller diameter. Other configurations are possible, and any suitable arrangement may be employed if desired.

When the control arm 162 is drawn to the extended position, the anchor 160 extends outside the control arm opening 161, and the anchor hook returns to a curved, unbiased configuration.

In practice, the anchor 160 may work in conjunction with, or as an alternative to, a position indication lumen 200 as described above. The suture device 101 may be inserted into the body with the control arm 162 and anchor 160 in, for example, the retracted position. As the device 101 approaches the desired position, the control arm 162 and anchor 160 may be moved to the extended position, so that the anchor hook 164 contacts the inside of the blood vessel and retains the suture device 101 in the desired position. Once the blood vessel has been suture as described above, the anchor 160 may be retracted and the suture device 101 removed from the body.

The operation of the device 101 according to this embodiment is shown in FIGS. 45—52. When an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 144 is inserted through the puncture to a target area within the blood vessel and a catheter is inserted through the introducer sheath, along the guide wire 144, to a target area within the blood vessel.

After the procedure is complete, the catheter and the introducer sheath are withdrawn and the guide wire 144 is left in place. A proximal end of the guide wire 144 is then inserted through the guide wire lumen 138 and the device 101 is inserted into the body and moved along the guide wire 144 through the puncture until the central portion 122 is located within the puncture (i.e. the walls of the blood vessel on opposite sides of the puncture surround the central portion 122). The major axis of the central portion 122 should be aligned with the length of the puncture so that the wall around the puncture is stretched as little as possible.

By observing the position indication lumen 201, the doctor may determine when the device 101 is in the desired position. Specifically, when the device 101 is inserted far enough into the blood vessel, blood will begin to be observed in the position identification lumen. Alternatively, an anchor 160, if provided, may also be used to position device 101.

As the device 101 is inserted into the blood vessel, the flexible tip 140 bends so that the device 101 is received within, and extends in the direction of the blood vessel without straining the vessel. In this position, the needle channels 123 are inside the blood vessel with the pointed tissue piercing ends of the needles facing proximally, that is, toward the proximal portion 118.

If desired, the needle receiving body 220 may then be introduced around the proximal portion 118 and slid down the proximal portion 118 until it reaches the stop 221. The needle receiving body may also be rotated, if necessary, to align the needle receiving lumens 226 with the needle channel openings 133 (assuming that the needle receiving body 220 is not fixedly attached to the elongated member 116).

With all the components of the device 101 in place, the operator may pull on the loop 142 in the length of suture 141. As the suture is withdrawn through the elongated member 116, it pulls the needles 137 out of the needle chamber 132 and the needle channels 123. The needles 137 penetrate the wall of the blood vessel on opposite sides of the puncture and enter the needle receiving lumens 226, if present. The needles 137 should be of sufficient length so that the proximal ends of the needles 137 exit the proximal end of the needle receiving body 220, if present.

Figure 50:
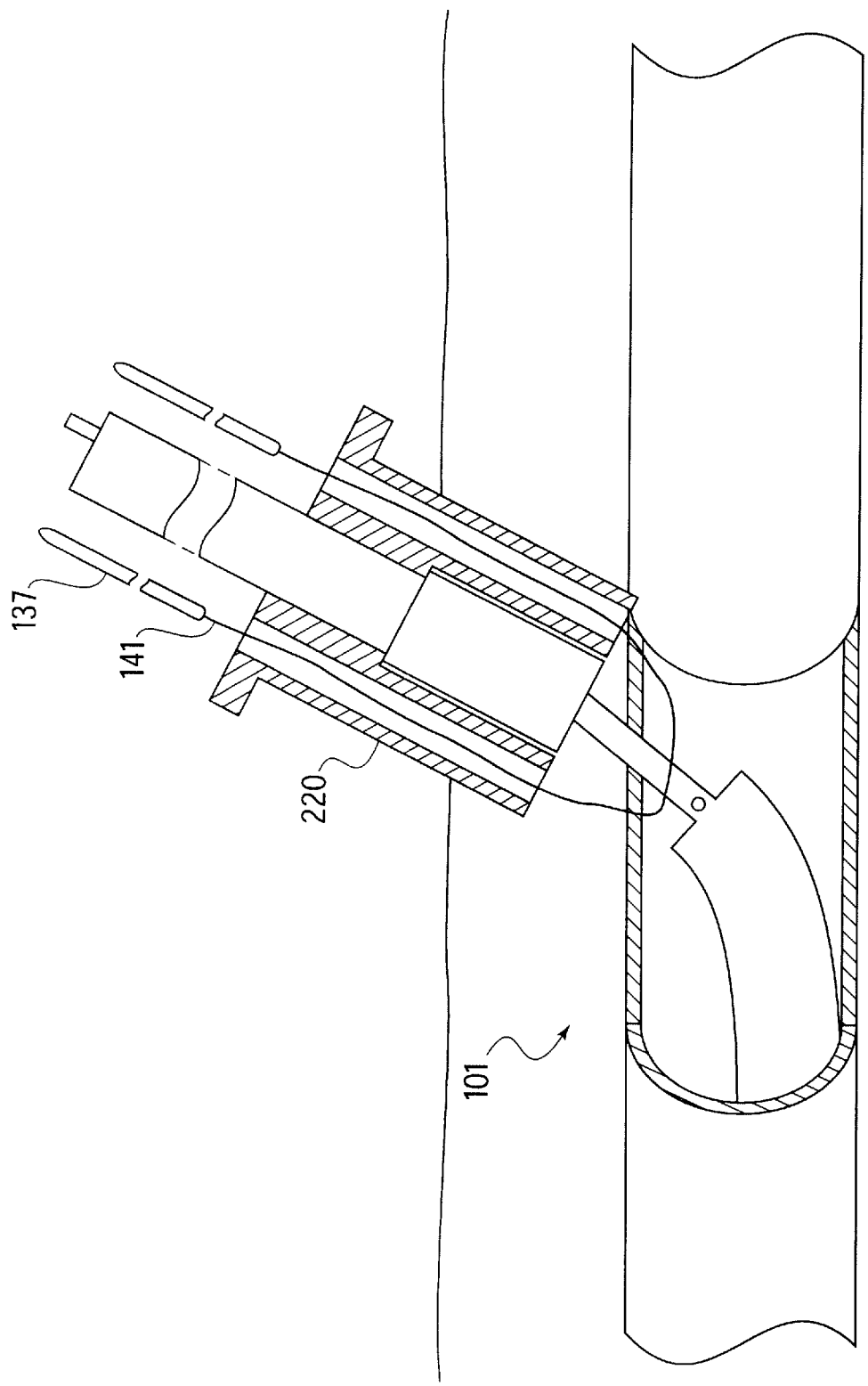
FIG. 50 shows a perspective view of the suture device of FIG. 49 with the pair of puncture needles fully deployed and a length of suture spanning the opening in the anatomical structure.
Figure 51:
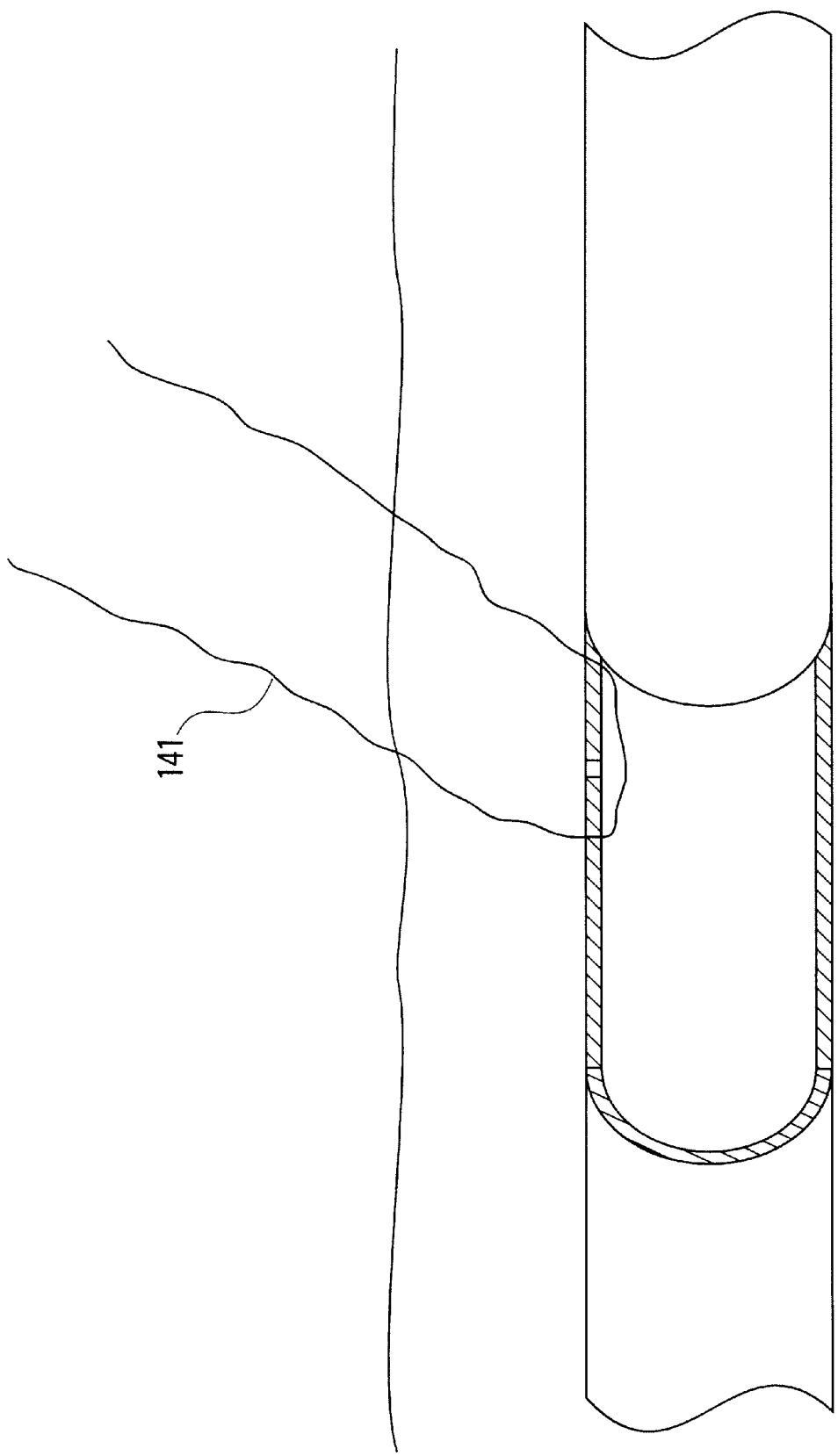
FIG. 51 shows a perspective view of a length of suture after being detached from a suture device according to the present invention.
Figure 52:
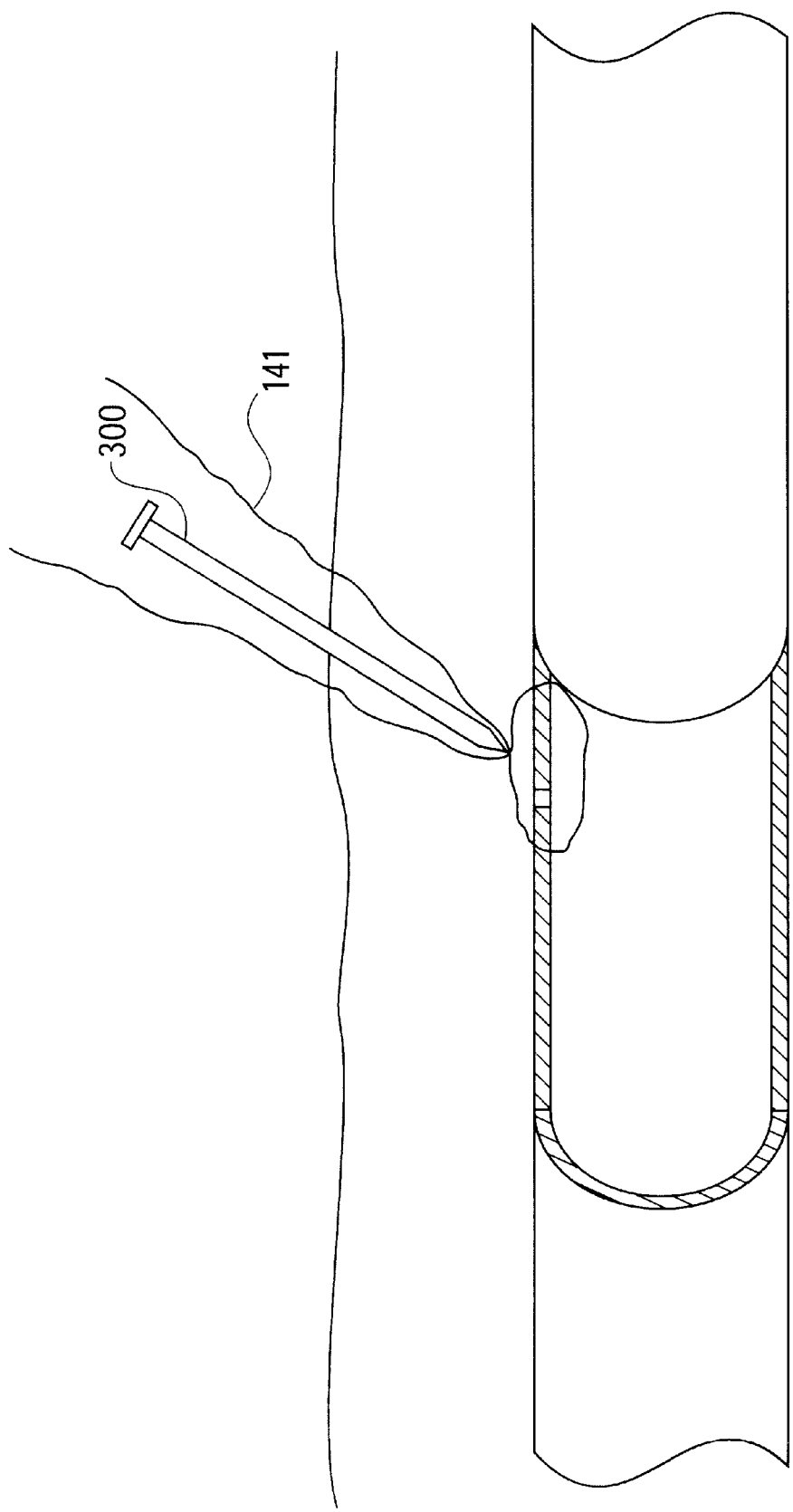
FIG. 52 shows a perspective view of a knot pusher according to the present invention pushing a knotted length of suture.

The operator may then grasp the needles 137 an pull them out of the blood vessel wall and/or needle receiving body 220, thereby pulling the loop 142 of the length of suture 141 back through the suture channel 130 and into the blood vessel, as shown in FIG. 50. The length of suture 141 may then be separated from the needles 137 and withdrawn from the needle receiving body. After the length of suture 141 is knotted, the knot pusher 300 may be used to tighten the knot and the length of suture 141 in general, thereby sealing the puncture. Of course, those skilled in the art will understand that, alternatively, a crimping device 500 as described above may be employed.

Figure 53:
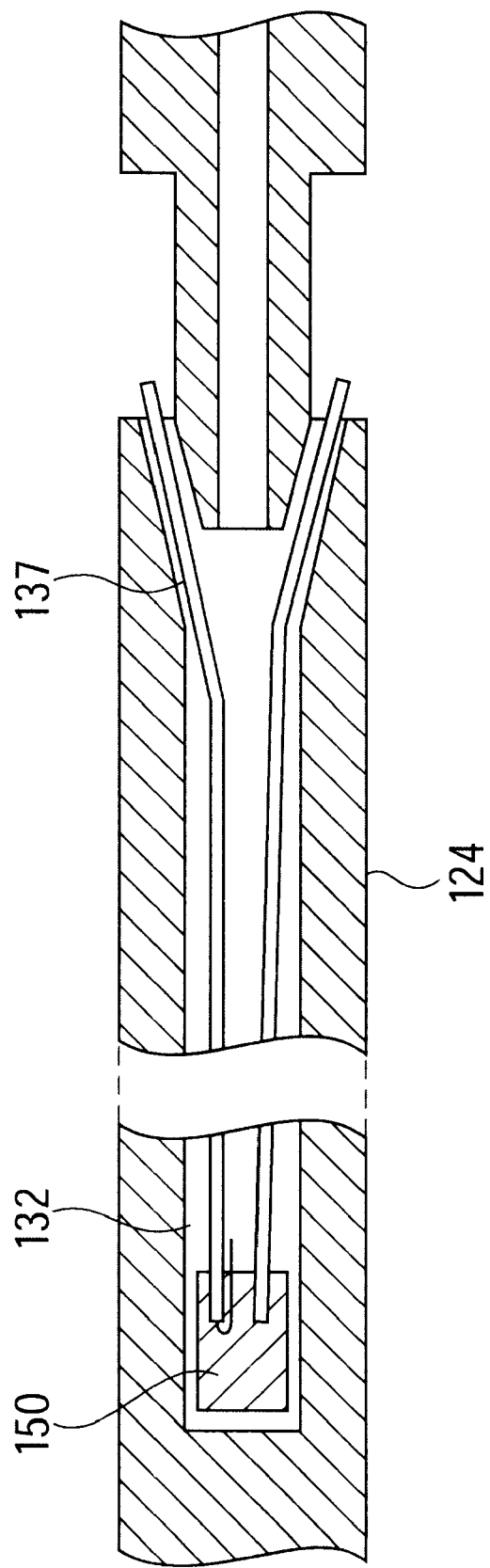
FIG. 53 shows a side view of another embodiment of the suture device according to the present invention.
Figure 54:
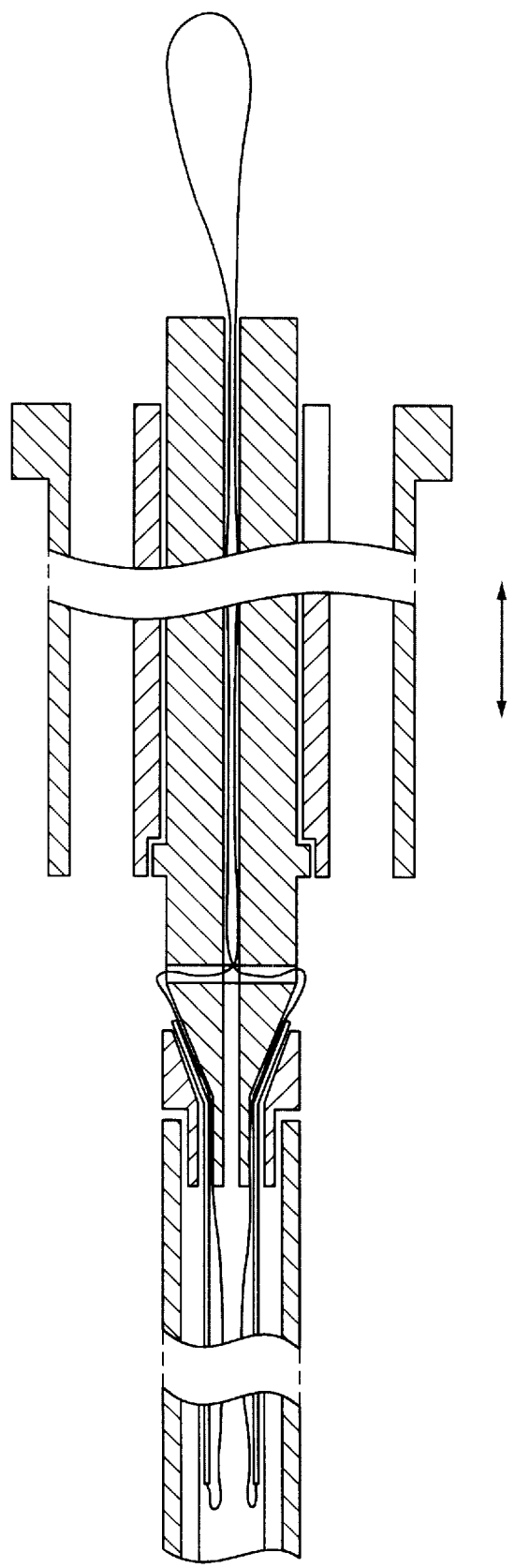
FIG. 54 shows a side view of a suture device according to the present invention including a needle receiving body according to the present invention.
Figure 57:
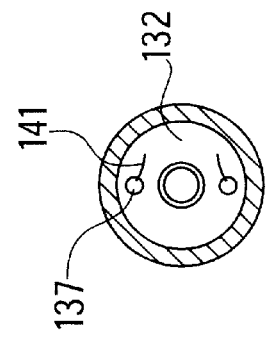
FIG. 57 shows a cross-sectional view of the suture device of FIG. 55 taken along ling 57—57 of FIG. 55.
Figure 56:
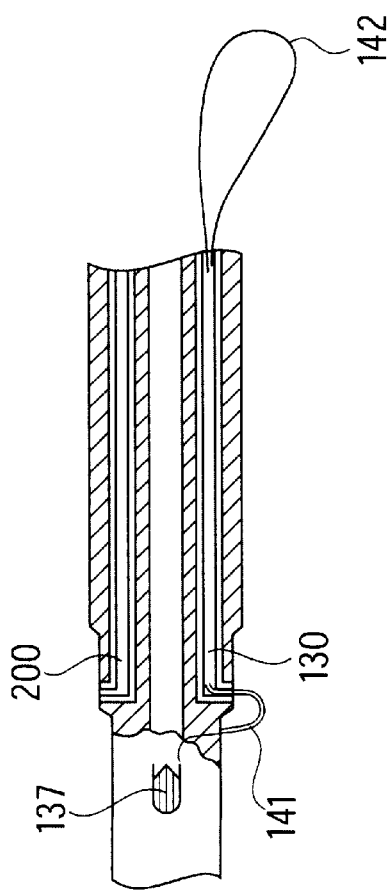
FIG. 56 shows a partial cross-sectional side view of the suture device of FIG. 55 taken along line 56—56 of FIG. 55.
Figure 59:
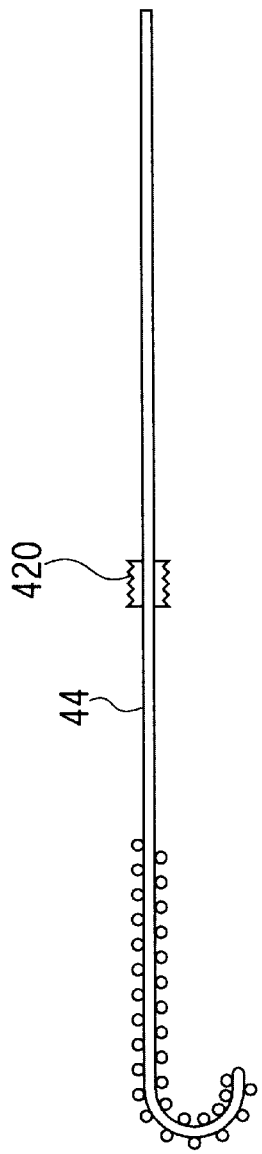
FIG. 59 shows a side view of an exemplary guide wire according to the present invention.

An additional feature of the device 101 according to the present invention is shown in FIG. 53. The needles 137 may be removably implanted in a platform 150 disposed within the needle chamber 132. The platform 150 allows the user to push the needles 137 back into the needle chamber 132 after they have been partially deployed by inserting a rod (not shown) into the suture lumen 130 and the needle chamber 132. The rod can be used to push the platform 150 distally, moving the needles 137 likewise distally, back to their initial position. This feature is useful if, for example, the length of suture 141 breaks prior to complete deployment or one of the needles 137 meets an obstruction.

Platform 150 is particularly useful in conjunction with a further embodiment of a suture device according to the present invention, in which the guide wire 44 is utilized to deploy needles 137. As illustrated in FIG. 55, a device 400 according to this embodiment includes a guide lumen 410 extending through the entire length of the device 400. Guide lumen 410 is constructed to receive guide wire 44, and is preferably disposed centrally within device 400, as illustrated in FIG. 58. Device 400 may include other lumens and chambers as described above.

Platform 150 of device 400 is preferably cylindrical in shape, meaning only that platform 150 preferably includes a bore therethrough. It should be understood that the term "cylindrical" therefore includes any configuration having a bore therethrough. Platform 150 may then be located so that the bore is aligned with guide lumen 410. In this manner, guide wire 44 may extend through platform 150.

Guide wire 44 of device 400 includes a fitting 420 coupled to wire 44, "coupled" including any arrangement in which fitting 420 and wire 44 are attached, including adhesive couplings, mechanical couplings, welding, or integral arrangements. Fitting 420 and platform 150 are constructed to selectively engage one another. Any type of engagement mechanism may be employed for this purpose. Preferred engagement mechanisms include internal and external threads or a lug and groove arrangement.

Figure 60:
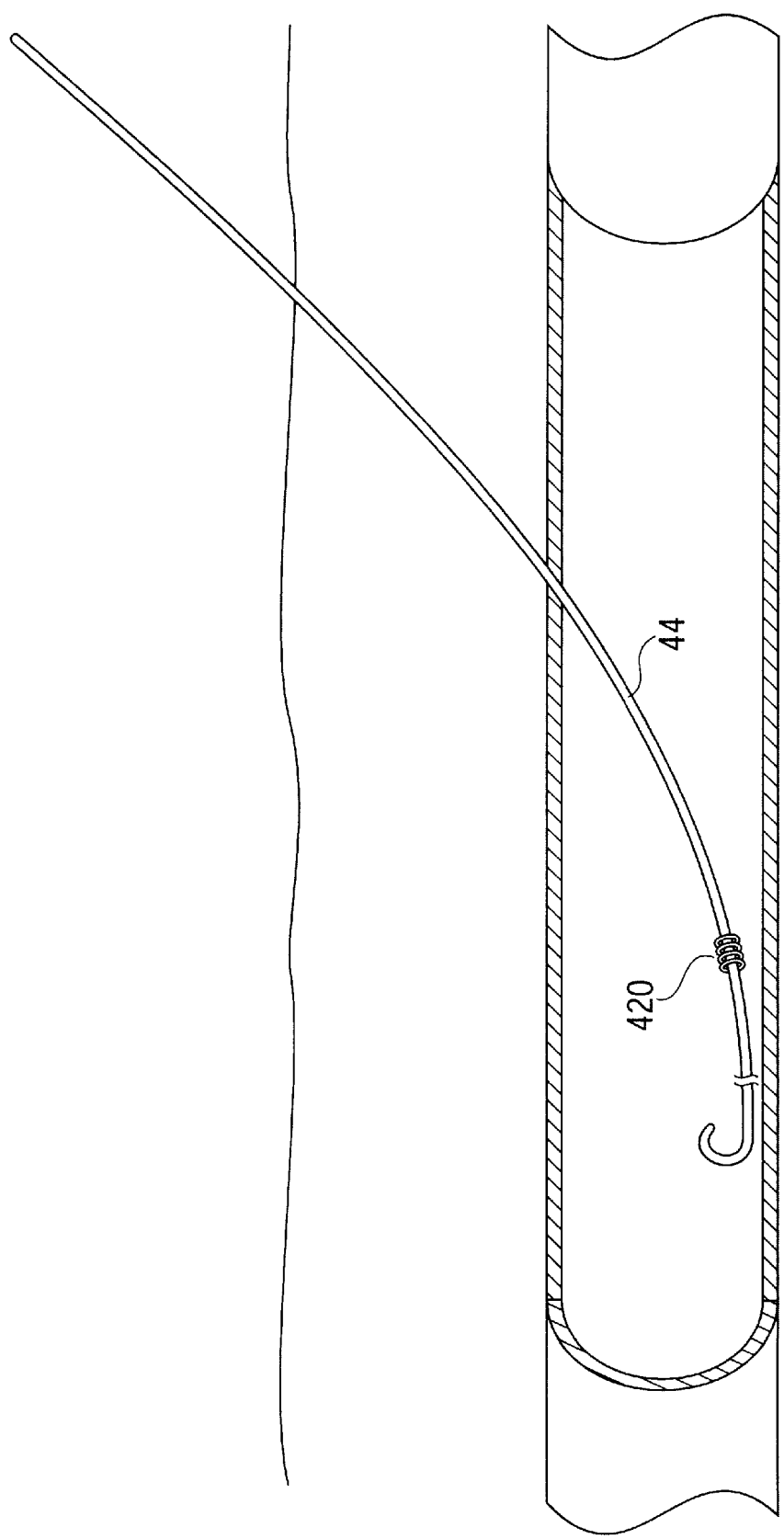
FIG. 60 shows a side view of the guide wire of FIG. 59 inserted into a lumen.
Figure 61:
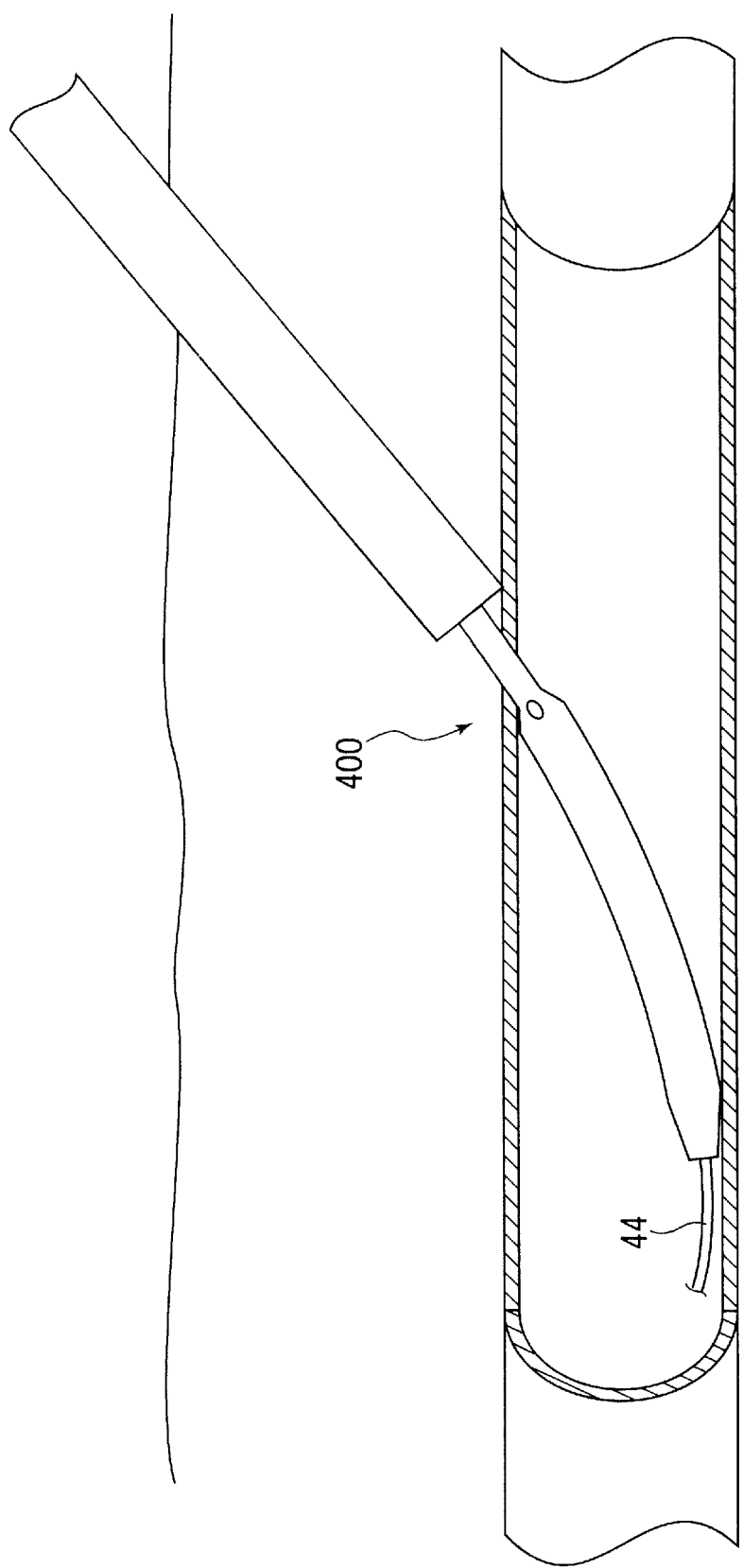
FIG. 61 shows a side view of the device of FIG. 55 inserted over the guide wire of FIG. 60.
Figure 62:
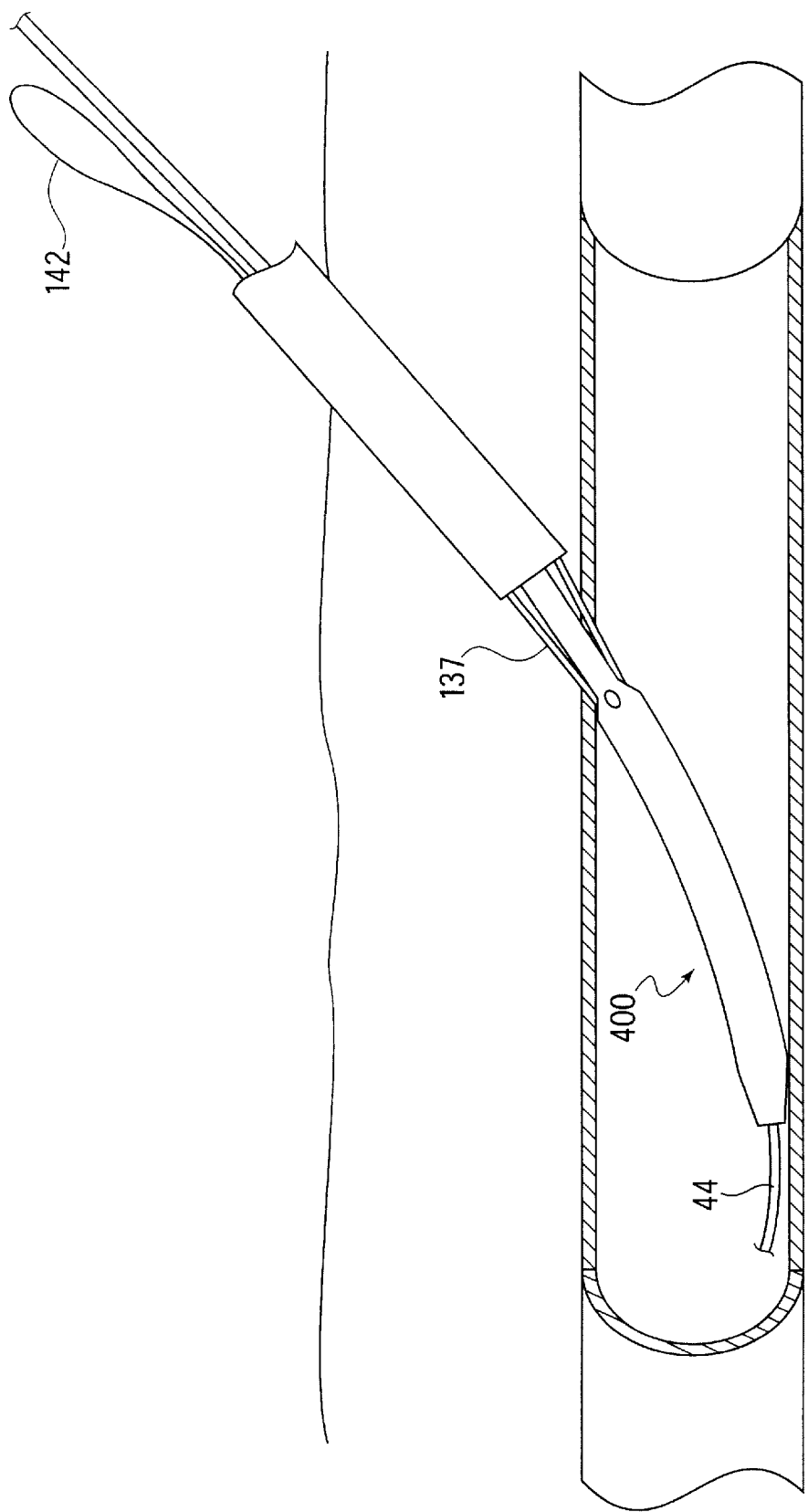
FIG. 62 shows the device of FIG. 61 with an exemplary pair of needles partially deployed.
Figure 63:
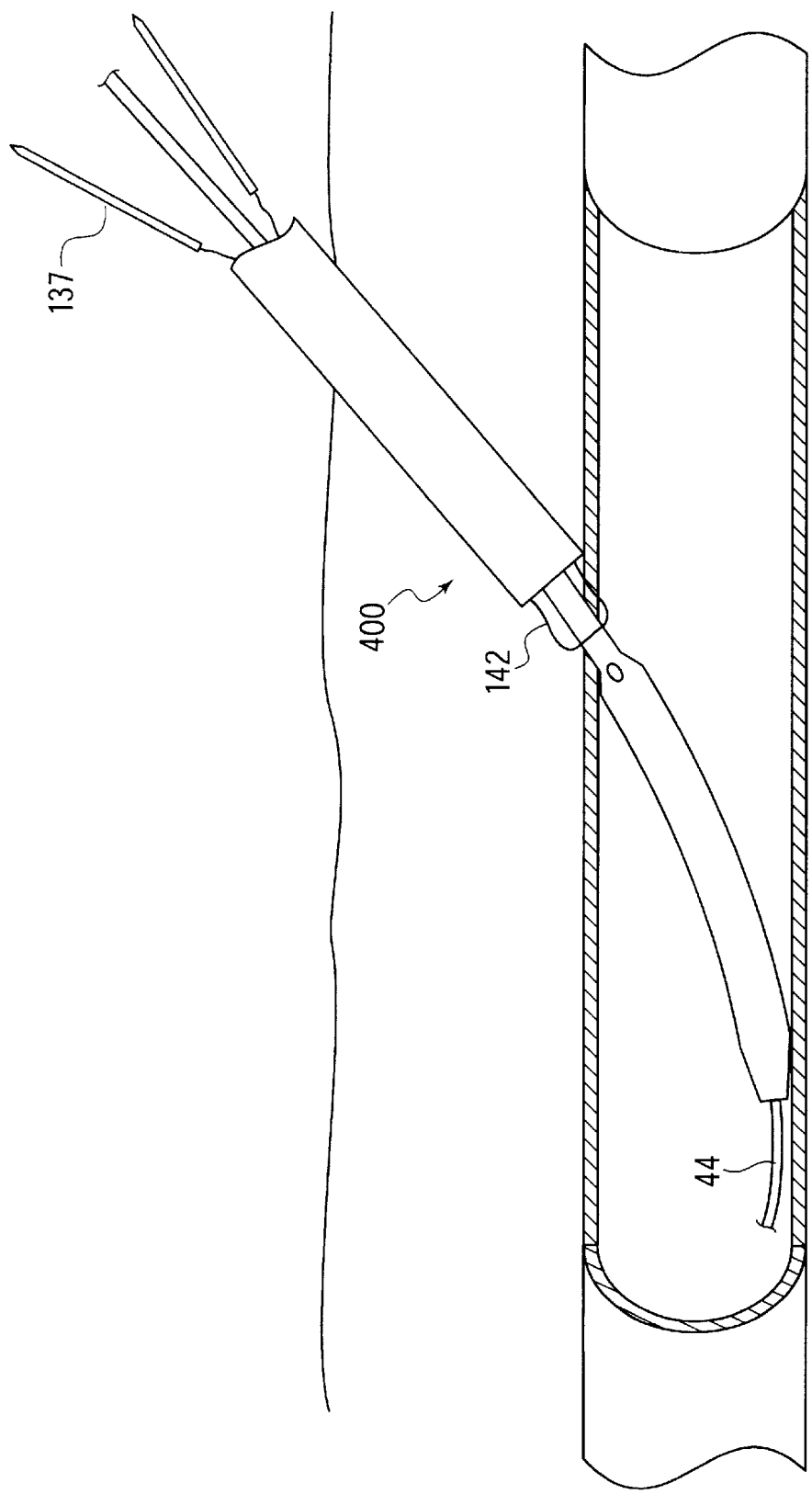
FIG. 63 shows the device of FIG. 61 with the exemplary pair of needles fully deployed.
Figure 64:
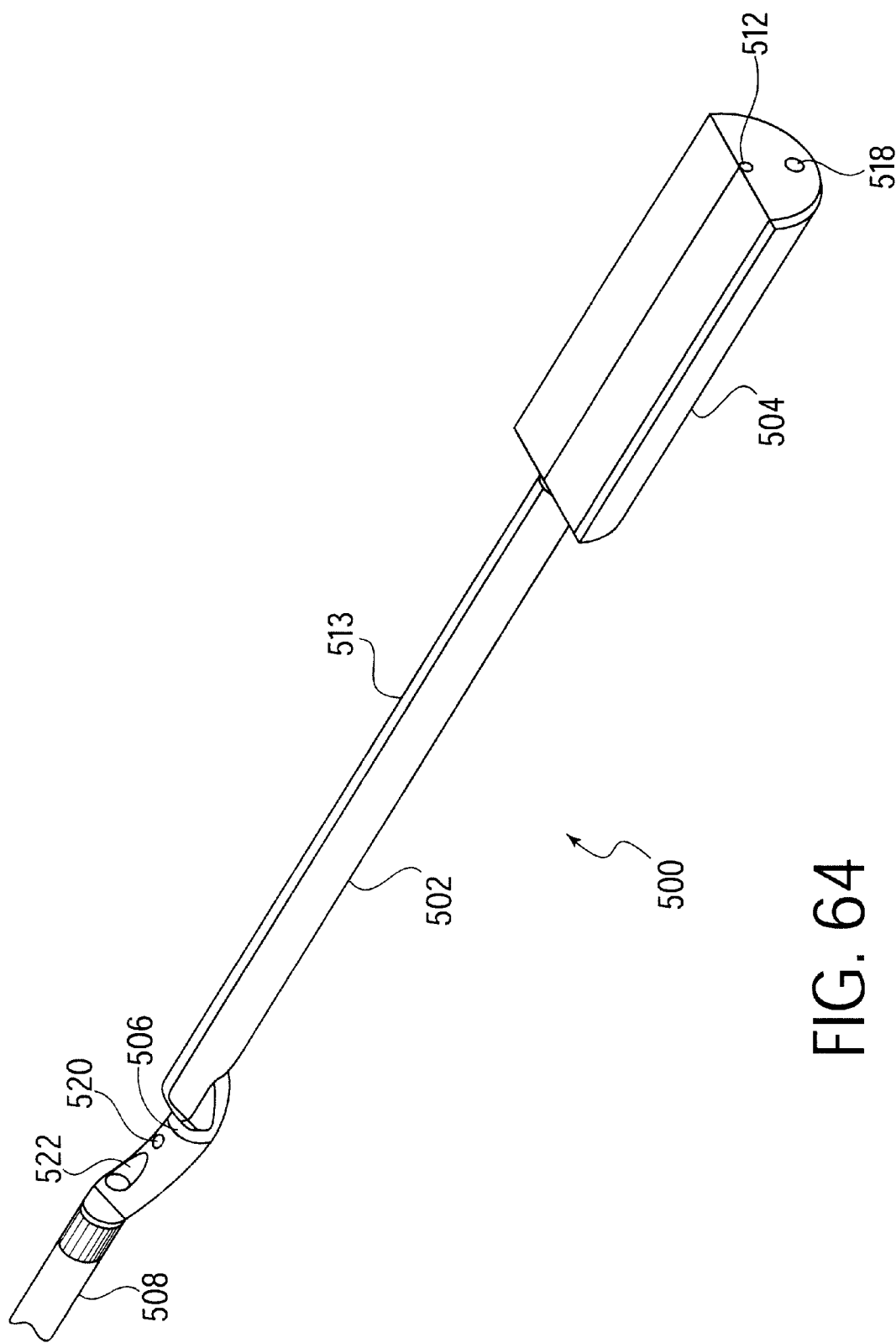
FIG. 64 shows a perspective view of a further exemplary embodiment of a suturing device according to the present invention.

In practice, guide wire 44 may be inserted into a blood vessel as illustrated in FIG. 60. Device 400 may then be inserted over guide wire 44. Once device 400 has been positioned according to any method, including those described above, guide wire 44 may be withdrawn until fitting 420 and platform 150 are in contact. Guide wire 44 or device 400 (or both) may then be manipulated, e.g. rotated, to engage fitting 420 and platform 150. Guide wire 44 then may be further withdrawn to deploy needles 137, as illustrated in FIGS. 61 to 63. Because this deployment does not require pulling on suture 141, the chance of severing suture 141 is minimized. It should be understood that while the illustrated embodiment includes a suture lumen 130, suture may be completely housed in device 400 if desired.

The embodiment of the device 101 according to the present invention has been described with respect to a single length of suture 141 and a single pair of needles 137. It can be understood, however, that simple modifications (e.g. the addition of more needle channels 123, etc.) allow the deployment of multiple needles simultaneously.

FIGS. 64–70 show a device 500 according to a further embodiment of the invention including a tube 502 having a substantially circular cross-section extending between a handle 504 and a central part 506 which is coupled to a distal end of the tube 502. The central part 506 curves away from an axis of the tube 502 along an arc by which the central part 506 returns toward the axis of the tube 502 to connect with a distal part 508. Thus, a distal end of the tube 502 faces a proximal end of the distal part 508 across a gap formed by the central part 506. A cross-sectional area of the central part 506 is substantially equal to that of the distal part 508 and the cross-sectional areas of both the central part 506 and the distal part 508 remain substantially constant along their entire lengths while a cross-sectional area of the tube 502 may preferably be equal or slightly greater than that of the distal part 508 and the central part 506. A guide wire lumen 507 extends through a distal portion of the distal part 508.

Figure 65:
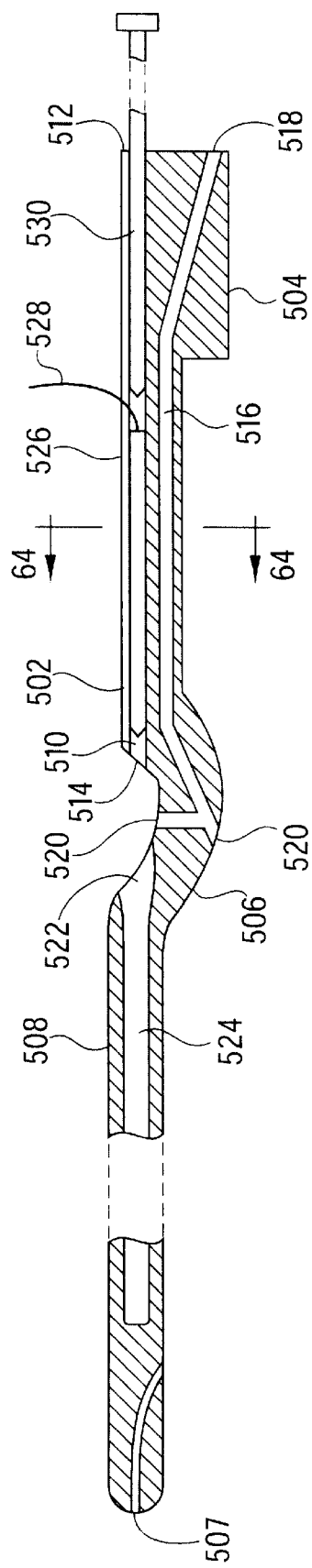
FIG. 65 shows a cross-sectional side view of the device of FIG. 64.
Figure 66:
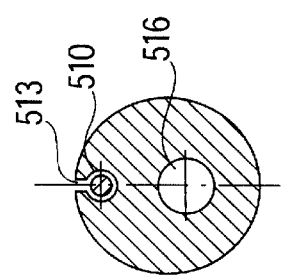
FIG. 66 shows a cross-sectional view of the device of FIG. 65 taken along line 64—64 of FIG. 65.

A needle insertion lumen 510 extends through the tube 502 and the handle 504 from an opening 512 formed in a proximal end of the handle 504 to an opening 514 formed at a distal end of the tube 502. A suture removal slot 513 extends through the surface of the handle 504 and the tube 502 to open an interior of the needle insertion lumen 510 to the outside of the device 500 along an entire length of the needle insertion lumen 510. A position indication lumen 516 extends from an opening 518 formed in the handle 504 through a portion of the central part 506 to openings 520 formed in the central part 506. A needle entry opening 522 formed in the proximal end of the distal part 508 extends into a needle receiving channel 524 which extends axially through the distal part 508. The needle receiving channel 524 extends for a length more than twice the length of needles 526 which are used with the device. In an initial configuration, no needles are received within the device 500. Alternatively, all or a portion of a first needle 526 may be received within the needle insertion lumen 510 so long as the pointed distal end of the first needle 526 remains within the needle insertion lumen 510. As will be described below, in use, the device is first inserted into a patient and then, when in a desired suturing position, the first needle 526 is inserted into the needle insertion lumen 510 via opening 512 as shown in FIG. 65 after which a needle pusher 530 is slid through the needle insertion lumen 510 behind the first needle 526. A loop of suture 528 is coupled between the proximal ends of a pair of needles 526 and the suture removal slot 513 is sized so that the first needle 526 is retained within the needle insertion lumen 510 while the suture 528 may be drawn out of the needle insertion lumen 510 through suture removal slot 513.

The device is preferably substantially rigid from the proximal end of the handle 504 to the needle entry opening 522 at the proximal end of the part 508 with a flexible tube extending distally from the proximal end of the distal part 508. This rigid structure ensures that the openings 514 and 522 remain properly aligned with one another during the procedure while the flexibility of the distal tube of the distal part 508 allows the distal part 508 to bend and follow the direction of the blood vessel without straining the blood vessel.

Figure 67:
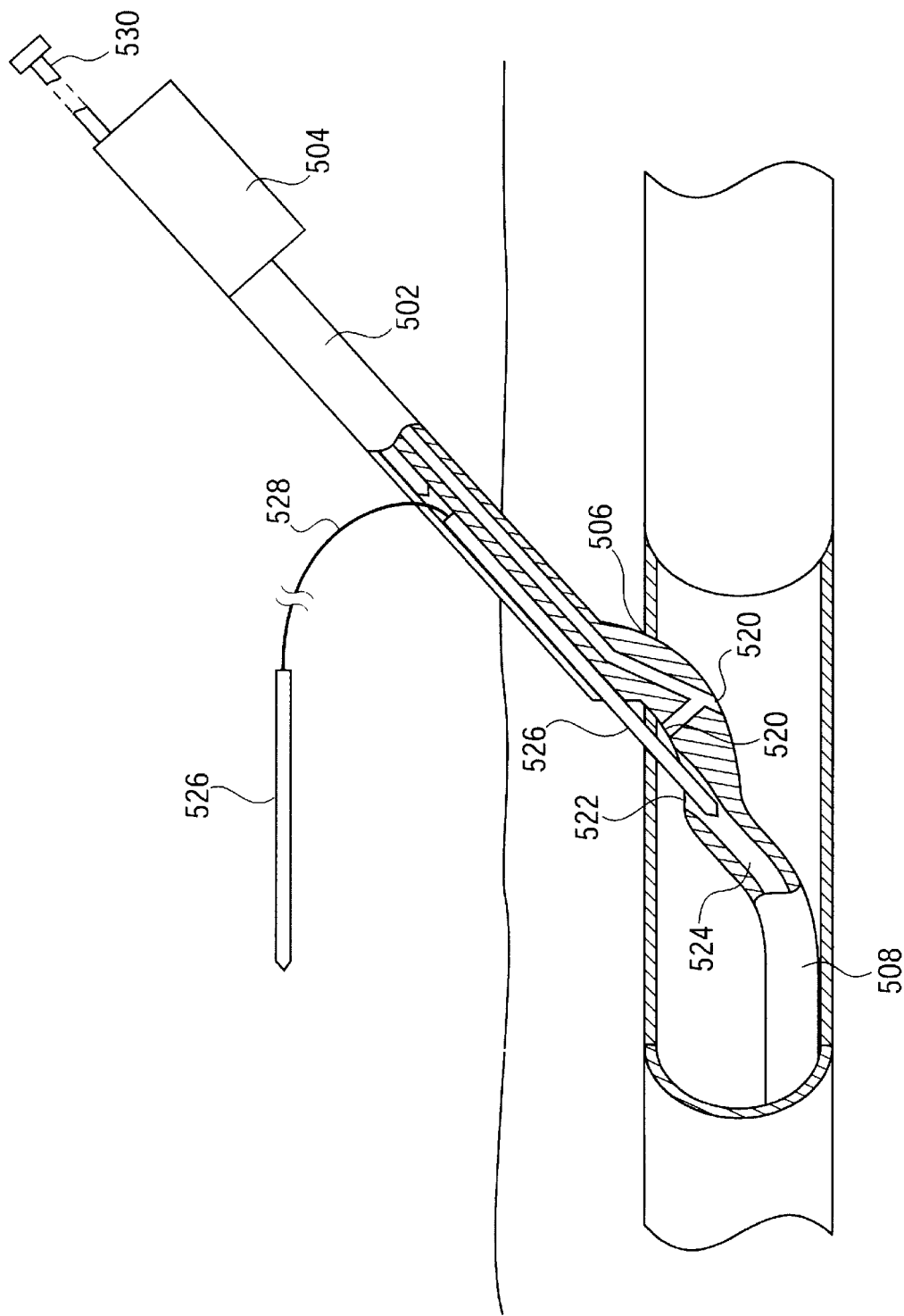
FIG. 67 shows a partially cross-sectional side view of the device of FIG. 64 in a first position within a blood vessel.

In operation as shown in FIG. 67, when an invasive procedure has been performed on a patient and a catheter previously inserted into a blood vessel (or other structure within the body) has been withdrawn, a guide wire may be left in place extending through the tissue tract, through the puncture into the blood vessel. The puncture must now be sealed. Thus, a proximal end of the guide wire may be inserted through the guide wire lumen 507 and the device 500 is inserted into the body and moved along the guide wire through the puncture until the central part 506 straddles a portion of the blood vessel wall adjacent to the puncture with the opening 514 located proximally of the blood vessel wall and the needle entry opening 522 within the blood vessel wall. The guide wire can now be withdrawn.

By observing the position indication lumen 516 and the needle insertion lumen 510, the doctor may determine when the device 500 is in the desired position. Specifically, when the device 500 is inserted far enough into the blood vessel, blood will be observed in the position indication lumen 516. However, if blood is observed in the needle insertion lumen 510, the doctor knows that the device 500 has been inserted too far into the blood vessel. When properly positioned within the blood vessel, the device 500 may be rotated to a specific orientation (if desired). As the device 500 is now properly positioned for the insertion of the first needle 526, the doctor inserts the first needle 526 and a first end of the loop of suture 528 attached thereto into the needle insertion lumen 510 through the opening 512 and pushes the needle 526 the suture 528 distally along the needle insertion lumen using the needle pusher 530. As the needle 526 is advanced distally, the sharpened distal end of the needle 526 exits the opening 514, penetrates the blood vessel wall and enters the needle receiving channel 524 via the needle entry opening 522. The doctor continues to advance the needle 526 distally until the proximal end of the needle 526 is completely received within the needle receiving channel 524 and then withdraws the needle pusher 530 from the device 500.

Figure 68:
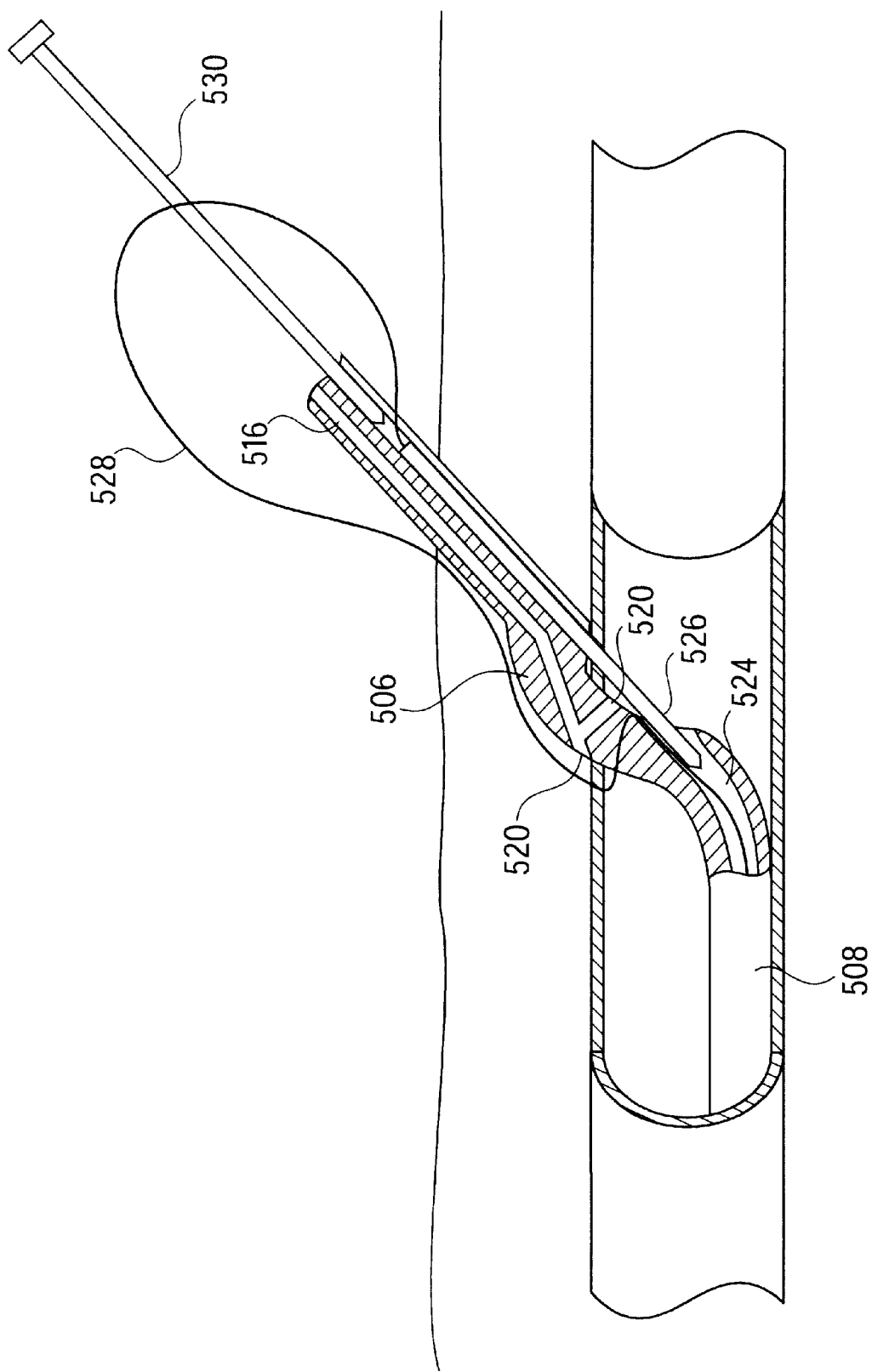
FIG. 68 shows a partially cross-sectional side view of the device of FIG. 64 in a second position within the blood vessel.

Thereafter, the doctor rotates the device 500 to a second orientation while observing the position indication lumen 516 and the needle insertion lumen 510 to ensure that the blood vessel wall is still received between the opening 514 and the needle entry opening 522 as shown in FIG. 68. The second portion of the blood vessel wall received between the opening 514 and the needle entry opening 522 will usually be separated from the point at which the first needle 526 penetrated the blood vessel wall by approximately 180°. Of course, those skilled in the art will understand that any angular separation may be achieved depending, for example, on the number of sutures the doctor wishes to use in sealing the blood vessel. When the device 500 is in the second orientation, the doctor inserts a second needle 526 and a second end of the loop of suture 528 coupled thereto into the needle insertion lumen 510 via the opening 512 and uses the needle pusher 530 to advance the second needle 526 distally through the needle insertion channel 510 and through the blood vessel wall until the proximal end of the second needle 526 is completely received within the needle receiving channel 524, as was done with the first needle 526.

Figure 69:
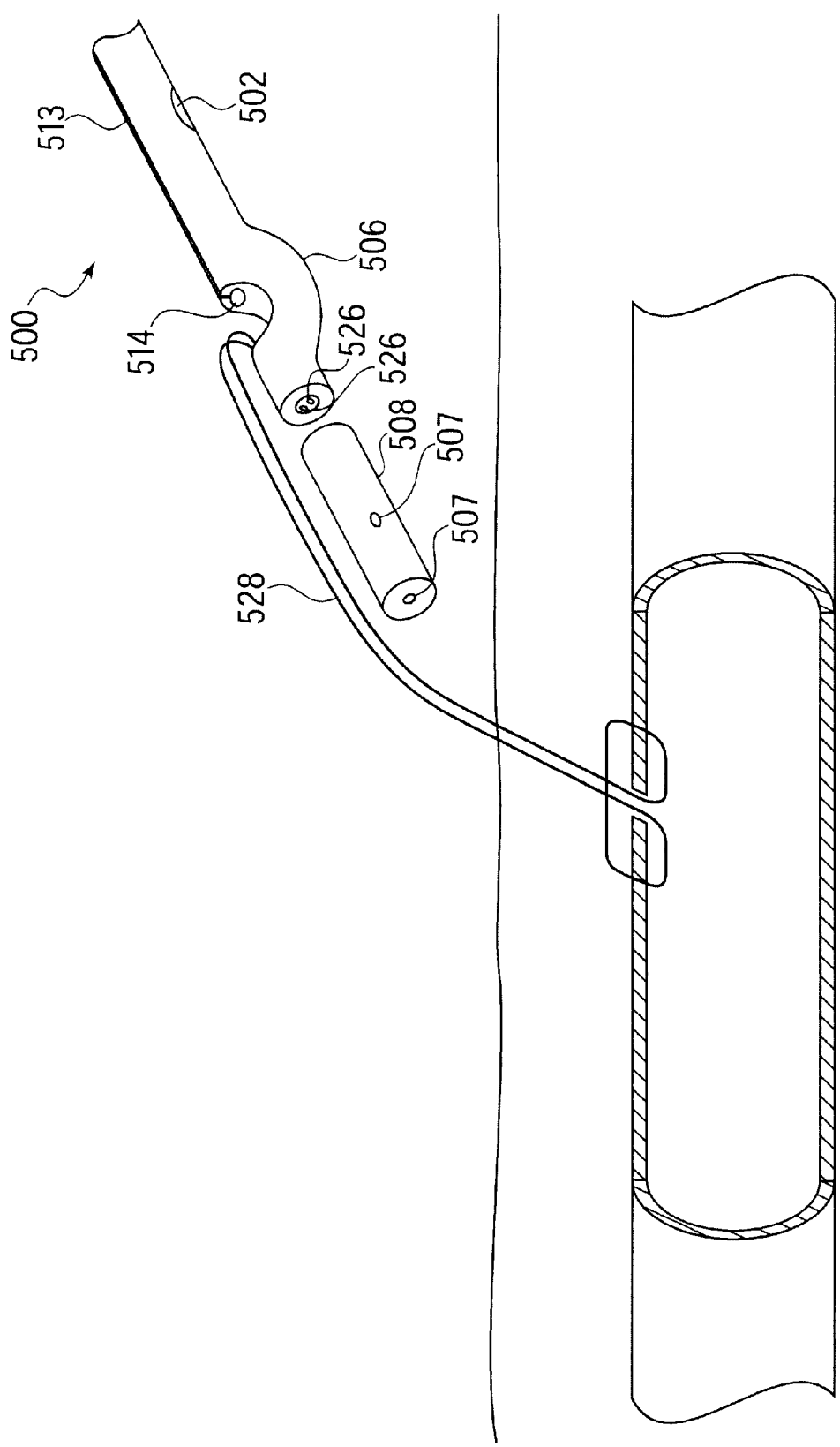
FIG. 69 shows a partially cross-sectional perspective view of the device of FIG. 64 after removal from the blood vessel.
Figure 70:
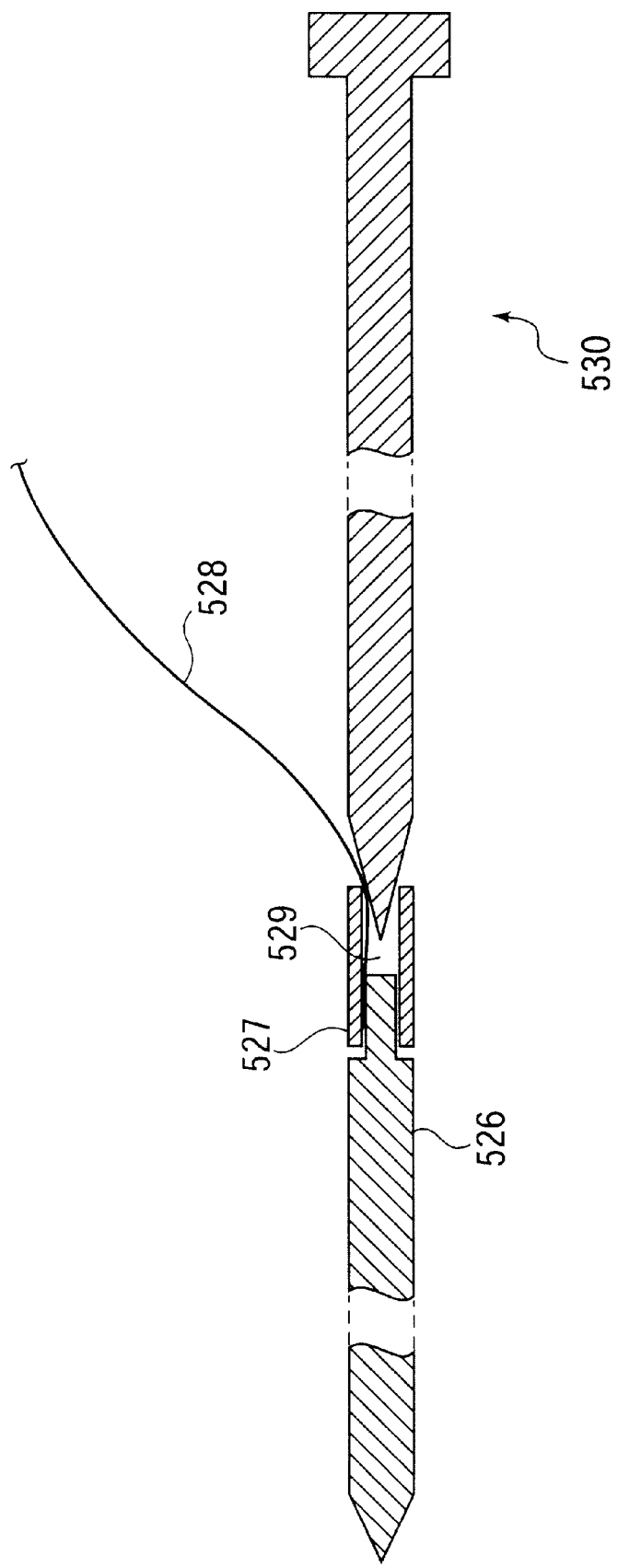
FIG. 70 shows a cross-sectional side view of a needle/pushing member for use in conjunction with the device of FIG. 64.
Figure 70A:
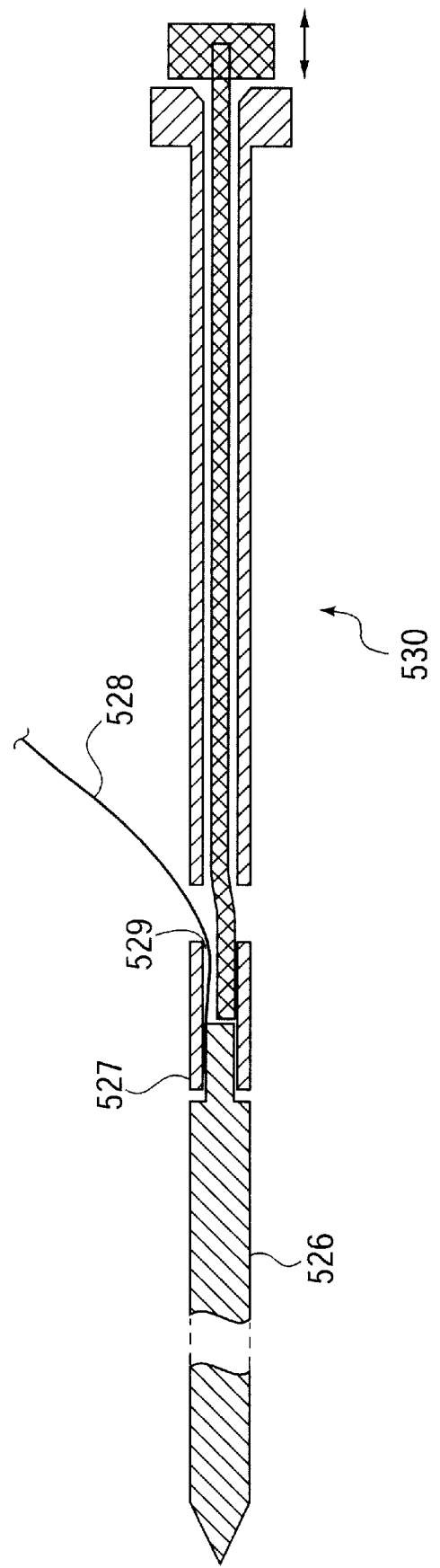
FIG. 70A shows a cross-sectional side view of an alternate needle pushing member for use in conjunction with the device of FIG. 64.

The doctor withdraws the needle pusher 530 from the device 500 and then withdraws the device 500 from the body, with the needles 526 received in the distal part 508. As shown in FIG. 69, the doctor then cuts the suture from the needles and tightens and knots the suture loop 528 to seal the puncture.

A device 600 according to a still further embodiment of the present invention is shown in FIGS. 71 and 72. Aside from the construction of the central portion 622, a new rotating element 602 and a flashback lumen 630 as described below, the construction and operation of the device 600 is substantially similar to that of the embodiment of FIGS. 64–70.

The central portion 622 includes a rotatable member 602 rotatably coupled between the proximal part 618 and the distal part 624. Specifically, the rotatable member 602 may rotate around the flashback lumen 630 by, for example, 1800. This creates a gap 605 between the proximal end of the distal part 624 and the distal end of the proximal part 618. The device 600 includes a rotating element 604 which is coupled to the rotatable member 602 so that, upon rotation by the user of the rotating element 604, the rotatable member 602 rotates by a corresponding angle. The rotating element 604 is connected to a proximal end 620 of the proximal part 618. The rotating element 604 may be coupled to the rotatable member 602 via a tube 608 slidably received in the proximal part 618 so that an inner diameter of the tube 608 forms a proximal part of the flashback lumen 630. Proximal and distal ends of this tube 608 are non-rotatably coupled to the rotating element 604 and the rotatable member 602, respectively. Of course, those skilled in the art will understand that the flashback lumen 630 may extend to any opening which, when the device is in an operative position within a blood vessel, is located within the blood vessel.

In operation, before the device 600 is inserted into the blood vessel of a patient, the rotatable member 602 is positioned by the physician (using the rotating element 604) so that an outer surface of the central portion 622 forms a substantially continuous surface with outer surfaces of the proximal part 618 and the distal part 624 (see FIG. 72). In this position, the device 600 preferably forms a substantially continuous cylinder. As with the prior embodiments, the device 600 is positioned so that the opening 633 is within the blood vessel while the needle exit opening 610 is outside the puncture on the proximal side of the blood vessel. The physician then rotates the rotating element 602 by, e.g., 180°, to rotate an upper surface 612 of the rotatable member 602 away from the corresponding portions of the proximal part 618 and the distal part 624, to create a gap 605 between the proximal part 618 and the distal part 624. The user then verifies the flow of blood through the flashback lumen 630 to ensure that the blood vessel wall is positioned between the openings 633 and 610. Thus, as described in regard to the previous embodiment, a needle 637 can be inserted distally through the needle insertion channel 626 to pierce the wall of the blood vessel and enter the needle receiving channel 632. The needle 637 is pushed distally until the entire needle is completely received within the needle receiving channel 632. The device is then rotated to a second position within the opening in the blood vessel wall and a second one of the needles 637 is inserted a second portion of the blood vessel wall into the needle receiving channel 632 until the second needle 637 is completely received in the needle receiving channel 632. The rotating element 602 is then rotated back into the position in which the device 600 forms a substantially continuous cylinder and the device 600 is withdrawn from the patient's body. The ends of a length of suture 641 coupled between the needles 637 are then coupled together to seal the opening. One of ordinary skill in the art will understand that the rotatable member 602 can be rotated to other positions beside the 180° rotation shown, so long as the gap 605 is sufficient to allow the needles 637 to pass between the openings 610 and 632.

Figure 73:
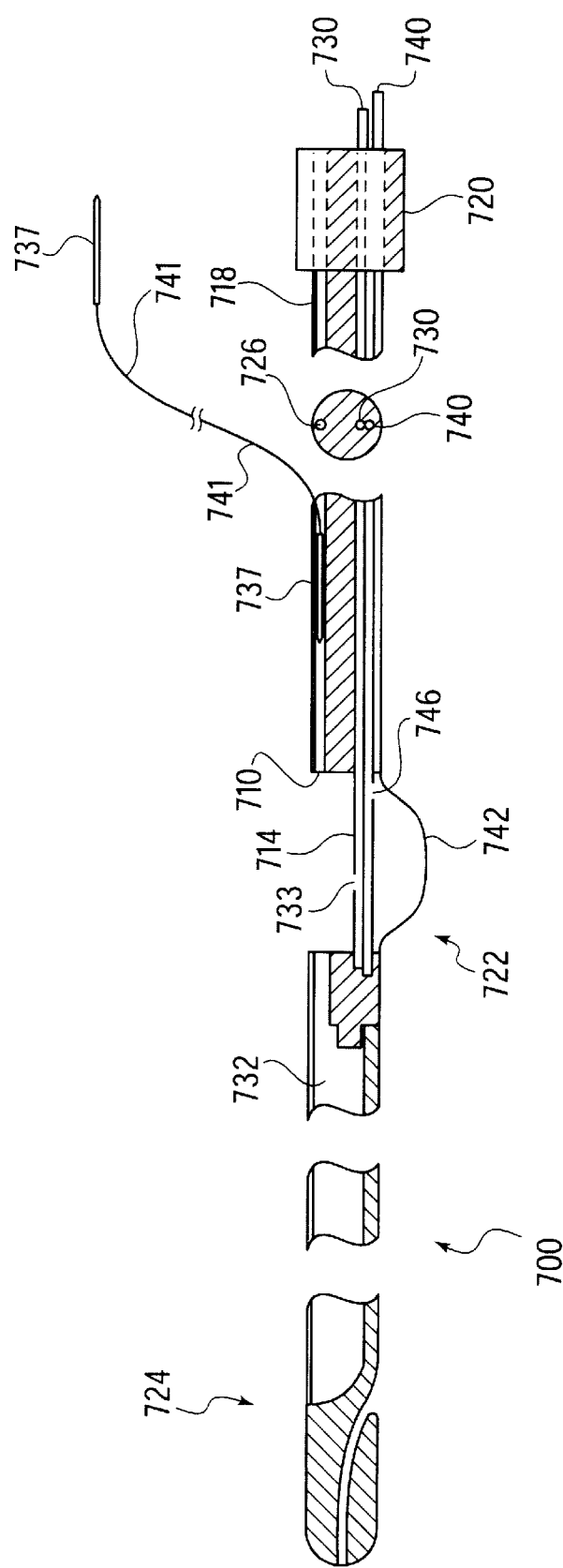
FIG. 73 shows a side view of a cross-section of a suturing device according to a further embodiment of the invention.
Figure 74:
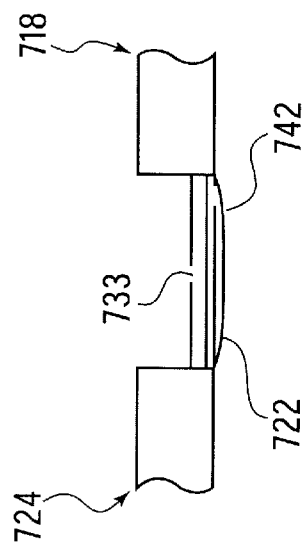
FIG. 74 shows the suturing device of FIG. 73 before entering the blood vessel.

FIGS. 73 and 74 illustrate a device 700 according to an additional embodiment of the present invention. The construction and operation of the device 700 is substantially similar to that of the device 600 of FIGS. 71 and 72, except for the construction of the central portion 722, the flashback lumen 730 and an additional inflation tube 740, as described below.

Specifically, the central portion 722 is located within a gap 714 situated between the proximal and distal parts 718 and 724. The central portion 722 includes an expandable member 742, preferably a balloon, which is adapted to be inflated via the inflation tube 740, which extends from the proximal end of the proximal part 718 to an inflation opening 746 formed at the distal end of the proximal portion 718. When air or other fluid is supplied to the expandable member 742 via inflation tube 740, the expandable member 742 expands away from a surface of the central portion 722 opposite the gap 714 to press against the wall of the blood vessel. This pushes the device 700 toward a portion of the blood vessel wall opposite the expandable member 742 so that this portion of the blood vessel wall is received at a predetermined location, preferably deep, within the gap 714.

In operation, when the device 700 is inserted into a blood vessel of a patient, the expandable member 742 is initially in a deflated state, extending along a surface of the device 700 adjacent to the flashback lumen 730 (see FIG. 73). When the device 700 is positioned so that the opening 733 is on a distal side of the puncture, and the opening 710 is positioned on the proximal side of the puncture, the physician provides a gas or a liquid through the inflation tube 740 to expand the expandable member 742. The expandable member 742 contacts a first portion of the blood vessel wall to aid in positioning the openings 733 and 710 of the device 700 at a first desired penetration location on the blood vessel wall. The expandable member 742 thus is used to prevent blood leakage during the sealing procedure by occluding the opening in the blood vessel wall. Thereafter, the user inserts a first needle 737 distally through the needle insertion lumen 726, as described above, to pierce the wall of the blood vessel at the first desired location, and enter the needle receiving channel 732 drawing a first end of a loop of suture 741 therethrough. The first needle 737 is pushed distally until the entire first needle 737 is completely received within the needle receiving channel 732.

The user then rotates the device 700 to a second position within the puncture. Thereafter, the user inserts a second needle 737, and a second end of the length of suture 741, through a second desired penetration location on the blood vessel wall until the entire second needle 737 is received within the needle receiving channel 732 and deflates the expandable member 742. The device 700 is then removed from the patient's body and the two ends of the loop of suture 741 are coupled together to seal the opening.

Those skilled in the art will understand that, as the needles of this device penetrate tissue on only one side of the puncture at a time, the diameter of the proximal part may be made as small as that of the distal and central parts and the puncture need not be further stretched as is required in larger diameter devices that deploy needles simultaneously to opposite sides of the puncture.

There are many other variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

What is claimed is:

1. A device for sealing a puncture in an anatomical structure comprising:
    a proximal portion having a first needle lumen extending therethrough to a first needle opening;
    a distal portion including a second needle opening facing the first needle opening across a tissue receiving gap and opening into a second needle lumen; and
    a connecting portion coupled between the proximal and distal portions and offset from the proximal and distal portions to create the tissue receiving gap whereby, when the connecting portion is received within a puncture in an anatomical structure, a portion of the anatomical structure received within the tissue receiving gap is located on one side of a plane including a central axis of the puncture.

2. The device according to claim 1, further comprising a flashback lumen extending through the proximal portion to a fluid entry opening formed distally of the distal end of the proximal portion.

3. The device according to claim 2, wherein the fluid entry opening is formed in the connecting member.

4. The device according to claim 1, further comprising a first needle, wherein the second needle lumen is sized so that, when the first needle is inserted distally thereinto, a proximal end of the first needle is inside the second needle lumen distal of the second needle opening.

5. The device according to claim 4, further comprising a second needle, wherein the second needle lumen is sized so that, when the first and second needles are inserted distally thereinto, the proximal end of the first needle and a proximal end of the second needle are inside the second needle lumen distal of the second needle opening.

6. The device according to claim 1, wherein a minimum cross-sectional area of the connecting member is at least as great as a maximum cross-sectional area of the distal portion.

7. The device according to claim 6, wherein the minimum cross-sectional area of the connecting member is substantially equal to the maximum cross-sectional area of the distal portion.

8. The device according to claim 6, wherein the connecting member and the distal portion are substantially tubular.

9. The device according to claim 6, wherein a minimum cross-sectional area of the proximal portion is at least as great as the minimum cross-sectional area of the connecting member.

10. The device according to claim 1, wherein a cross-sectional area of the first needle lumen is smaller than a cross-sectional area of the second needle lumen.

11. The device according to claim 1, wherein the first needle lumen and the first and second needle openings extend along a common axis.

12. The device according to claim 11, wherein the proximal portion and the connecting member are formed of a substantially rigid material.

13. The device according to claim 12, wherein the distal portion includes a rigid proximal end with a flexible tube extending distally therefrom.

14. The device according to claim 13, wherein the proximal portion, the connecting member and the proximal end of the distal portion are integrally formed.

15. The device according to claim 1, further comprising a needle pushing member which receives in a distal end thereof a proximal end of a needle.

16. A device for sealing a puncture in an anatomical structure comprising:
    a proximal portion having a first needle lumen extending therethrough to a first needle opening;
    a distal portion having a second needle opening opening into a second needle lumen; and
    a connecting member coupled between a distal end of the proximal portion and a proximal end of the distal portion, the connecting member having a minimum cross-sectional area at least as great as a maximum cross-sectional area of the distal portion, the connecting member being offset from the proximal and distal portions to form a tissue receiving gap therebetween.

17. A device for sealing a puncture in an anatomical structure comprising:
    a proximal portion having at least one first needle lumen extending therethrough to a first needle opening;
    a distal portion having at least one second needle opening, each second needle opening opening into a corresponding second needle lumen; and
    a connecting member coupled between a distal end of the proximal portion and a proximal end of the distal portion, the connecting member being offset from the proximal and distal portions to form a tissue receiving gap therebetween wherein, when the device is positioned with the connecting member extending through a puncture, every second needle opening is located on one side of a plane including a central axis of the puncture.

18. A device for sealing a puncture in an anatomical structure comprising:
    a proximal portion having at least one first needle lumen extending therethrough to a first needle opening;
    a distal portion having at least one second needle opening, each second needle opening opening into a corresponding second needle lumen; and
    a connecting member coupled between a distal end of the proximal portion and a proximal end of the distal portion, the connecting member being offset from the proximal and distal portions to form a tissue receiving gap therebetween so that the proximal portion and the connecting member are asymmetrical with respect to one another.

19. A device for sealing a puncture in an anatomical structure comprising:
    a proximal portion having at least one first needle lumen extending therethrough to a first needle opening;
    a distal portion having at least one second needle opening, each second needle opening opening into a corresponding second needle lumen; and
    a connecting member coupled between a distal end of the proximal portion and a proximal end of the distal portion, the connecting member being offset from the proximal and distal portions to form a tissue receiving gap therebetween, wherein, when the device is positioned with the connecting member extending through a puncture, the second needle opening is located on a first side of a plane including a central axis of the puncture and the distal portion includes no needle opening on a second side of the plane opposite the first side.

* * * * *

UNITED STATES PATENT AND TRADEMARK OFFICE
CERTIFICATE OF CORRECTION

PATENT NO.    : 6,436,109 B1
DATED         : August 20, 2002
INVENTOR(S)   : Kontos It is certified that error appears in the above-identified patent and that said Letters Patent is hereby corrected as shown below:

Column 4,
Line 44, delete "ling" and insert -- line --

Column 11,
Line 54, delete "900" and insert -- 90° --

Column 14,
Line 6, delete "cyonacrylate" and insert -- cyanoacrylate --

Column 16,
Line 16, delete "an" and insert -- and --

Signed and Sealed this

Twenty-second Day of April, 2003

JAMES E. ROGAN
*Director of the United States Patent and Trademark Office*